United States Patent
Degenhardt et al.

(10) Patent No.: US 7,476,680 B2
(45) Date of Patent: *Jan. 13, 2009

(54) SUBSTITUTED HETEROCYCLIC COMPOUNDS FOR TREATING MULTIDRUG RESISTANCE

(75) Inventors: Charles Raymond Degenhardt, Cincinnati, OH (US); David Joseph Eickhoff, Edgewood, KY (US)

(73) Assignee: H. Lee Moffitt Cancer Center & Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/425,874

(22) Filed: Jun. 22, 2006

(65) Prior Publication Data

US 2006/0223853 A1    Oct. 5, 2006

Related U.S. Application Data

(60) Continuation of application No. 09/996,657, filed on Nov. 29, 2001, now Pat. No. 7,135,483, which is a division of application No. 09/740,643, filed on Dec. 19, 2000, now Pat. No. 6,376,514.

(60) Provisional application No. 60/241,127, filed on Oct. 17, 2000.

(51) Int. Cl.
*C07D 215/38* (2006.01)
*A61K 31/48* (2006.01)

(52) U.S. Cl. ............... 514/314; 514/313; 514/311; 546/159; 546/196; 546/198

(58) Field of Classification Search ............ 514/314, 514/313, 311; 546/159, 196, 198
See application file for complete search history.

(56) References Cited

U.S. PATENT DOCUMENTS

| | | |
|---|---|---|
| 4,029,801 A | 6/1977 | Cavalla et al. |
| 4,181,722 A | 1/1980 | Beranger et al. |
| 4,237,139 A | 12/1980 | Champseix et al. |
| 4,299,835 A | 11/1981 | Champseix et al. |
| 4,402,961 A | 9/1983 | Dubroeucq et al. |
| 4,433,150 A | 2/1984 | Champseix et al. |
| 4,442,106 A | 4/1984 | Trijzelaar et al. |
| 4,442,107 A | 4/1984 | Trijzelaar et al. |
| 4,443,453 A | 4/1984 | Trijzelaar et al. |
| 4,472,403 A | 9/1984 | Trijzelaar et al. |
| 4,505,916 A | 3/1985 | Champseix et al. |
| 4,584,303 A | 4/1986 | Huang et al. |
| 4,613,607 A | 9/1986 | Gueremy et al. |
| 4,791,120 A | 12/1988 | Lin et al. |
| 4,911,923 A | 3/1990 | Wallach |
| 4,916,142 A | 4/1990 | Bagley et al. |
| 4,923,871 A | 5/1990 | Inaba et al. |
| 4,935,432 A | 6/1990 | Matsuo et al. |
| 4,962,115 A | 10/1990 | Van Daele |
| 4,963,553 A | 10/1990 | Tseng et al. |
| 4,980,351 A | 12/1990 | Barth et al. |
| 4,985,438 A | 1/1991 | Archibald et al. |
| 4,985,558 A | 1/1991 | Suzuki et al. |
| 4,996,321 A | 2/1991 | Baldwin et al. |

(Continued)

FOREIGN PATENT DOCUMENTS

| | | |
|---|---|---|
| BE | 563610 | 6/1958 |
| CA | 2198645 | 2/1997 |
| CA | 2337941 | 2/2000 |
| DE | 3524955 | 1/1986 |
| DE | 195 48 797 | 7/1997 |

(Continued)

OTHER PUBLICATIONS

Abderrabi, M. et al., "Comparative in vitro evaluation of dithiane analogs of tiapamil, Ro 11-2933, Ro 44-5911 and Ro 44-5912 as multidrug resistance modulators" Anti-Cancer Drugs, 7, p. 430-436 (1996).

(Continued)

*Primary Examiner*—D. Margaret Seaman
(74) *Attorney, Agent, or Firm*—Michael Best & Friedrich LLP

(57) ABSTRACT

Compounds suitable for treating multidrug resistance and methods for their preparation and use are disclosed. The compounds are represented by the following formula:

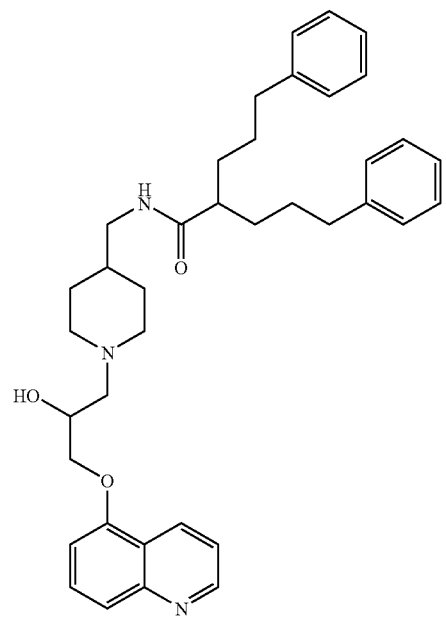

or an optical isomer, diastereomer, enantiomer or pharmaceutically acceptable salt thereof.

9 Claims, No Drawings

U.S. PATENT DOCUMENTS

| | | | |
|---|---|---|---|
| 5,013,742 A | 5/1991 | Kudzma et al. | |
| 5,091,187 A | 2/1992 | Haynes | |
| 5,098,915 A | 3/1992 | Dedsai et al. | |
| 5,112,817 A | 5/1992 | Fukazawa et al. | |
| 5,114,919 A | 5/1992 | Baldwin et al. | |
| 5,124,339 A | 6/1992 | King | |
| 5,130,303 A | 7/1992 | Akiyama et al. | |
| 5,160,727 A | 11/1992 | Klohs et al. | |
| 5,173,486 A | 12/1992 | Monkovic et al. | |
| 5,177,077 A | 1/1993 | Hohlweg et al. | |
| 5,182,293 A | 1/1993 | Sunkara et al. | |
| 5,189,036 A | 2/1993 | Chou et al. | |
| 5,190,946 A | 3/1993 | Ramu et al. | |
| 5,190,957 A | 3/1993 | Sunkara et al. | |
| 5,204,348 A | 4/1993 | Fukazawa et al. | |
| 5,216,172 A | 6/1993 | Toyota et al. | |
| 5,225,405 A | 7/1993 | Paramelle et al. | |
| 5,238,936 A | 8/1993 | Regnier et al. | |
| 5,272,159 A | 12/1993 | Baldwin et al. | |
| 5,292,726 A | 3/1994 | Ashton et al. | |
| 5,292,757 A | 3/1994 | Ohsumi et al. | |
| 5,302,727 A | 4/1994 | Eliason et al. | |
| 5,336,685 A | 8/1994 | Prochaska et al. | |
| 5,362,729 A | 11/1994 | Cozzi et al. | |
| 5,371,081 A | 12/1994 | Houghton et al. | |
| 5,389,644 A | 2/1995 | Peglion et al. | |
| 5,409,690 A | 4/1995 | Howell et al. | |
| 5,416,091 A | 5/1995 | King | |
| 5,436,243 A | 7/1995 | Sachs et al. | |
| 5,506,239 A | 4/1996 | Sato et al. | |
| 5,508,403 A | 4/1996 | Akiyama et al. | |
| 5,514,664 A | 5/1996 | Ulrich | |
| 5,516,775 A | 5/1996 | Zimmermann et al. | |
| 5,521,184 A | 5/1996 | Zimmermann | |
| 5,523,304 A | 6/1996 | Sunkara | |
| 5,525,606 A | 6/1996 | Moschel et al. | |
| 5,536,722 A | 7/1996 | Coe et al. | |
| 5,541,232 A | 7/1996 | Howell et al. | |
| 5,543,423 A | 8/1996 | Zelle et al. | |
| 5,543,428 A | 8/1996 | Sawyer et al. | |
| 5,550,149 A | 8/1996 | Powell et al. | |
| 5,569,471 A | 10/1996 | Oguro | |
| 5,571,687 A | 11/1996 | Casey et al. | |
| 5,583,137 A | 12/1996 | Coe et al. | |
| 5,605,896 A | 2/1997 | Leonardi et al. | |
| 5,610,165 A | 3/1997 | MacCoss et al. | |
| 5,620,971 A | 4/1997 | Armistead et al. | |
| 5,622,953 A | 4/1997 | Janssen et al. | |
| 5,643,869 A | 7/1997 | Dreyfuss et al. | |
| 5,654,304 A | 8/1997 | Pfister et al. | |
| 5,663,179 A | 9/1997 | Dumaitre et al. | |
| 5,665,719 A | 9/1997 | Bock et al. | |
| 5,670,508 A | 9/1997 | Wang et al. | |
| 5,670,521 A | 9/1997 | Freedman et al. | |
| 5,693,767 A | 12/1997 | Klemke et al. | |
| 5,698,553 A | 12/1997 | Purcher et al. | |
| 5,700,826 A | 12/1997 | Mjalli et al. | |
| 5,723,459 A | 3/1998 | Armistead et al. | |
| 5,726,184 A | 3/1998 | Zelle et al. | |
| 5,733,911 A | 3/1998 | Eilon et al. | |
| 5,736,539 A | 4/1998 | Graham et al. | |
| 5,744,485 A | 4/1998 | Zelle et al. | |
| 5,756,422 A | 5/1998 | Holdgrun et al. | |
| 5,756,475 A | 5/1998 | Inomata et al. | |
| 5,756,527 A | 5/1998 | Mjalli et al. | |
| 5,763,443 A | 6/1998 | Medlen et al. | |
| 5,776,939 A | 7/1998 | Kroin et al. | |
| 5,789,402 A | 8/1998 | Audia et al. | |
| 5,811,434 A | 9/1998 | Zelle et al. | |
| 5,814,644 A | 9/1998 | Kulagowski et al. | |
| 5,827,846 A | 10/1998 | Regenass et al. | |
| 5,830,915 A | 11/1998 | Pikul et al. | |
| 5,834,014 A | 11/1998 | Weiner et al. | |
| 5,840,319 A | 11/1998 | Alakhov et al. | |
| 5,840,721 A | 11/1998 | Mjalli et al. | |
| 5,851,789 A | 12/1998 | Simon et al. | |
| 5,852,018 A | 12/1998 | Bryans et al. | |
| 5,885,786 A | 3/1999 | Cabot | |
| 5,928,637 A | 7/1999 | Gottesman et al. | |
| 5,935,954 A | 8/1999 | Armistead et al. | |
| 5,968,956 A | 10/1999 | Okada et al. | |
| 6,174,900 B1 | 1/2001 | Okada et al. | |
| 6,200,990 B1 | 3/2001 | Namil et al. | |
| 6,211,186 B1 | 4/2001 | McIver et al. | |
| 6,221,872 B1 | 4/2001 | Gangee | |
| 6,258,526 B1 | 7/2001 | Stein et al. | |
| 6,329,872 B1 | 12/2001 | Chatterjee | |
| 6,376,514 B1 * | 4/2002 | Degenhardt et al. | ......... 514/314 |
| 6,403,610 B1 | 6/2002 | Malleron et al. | |
| 6,413,984 B1 | 7/2002 | Philippo et al. | |
| 6,448,243 B1 | 9/2002 | Kitazawa et al. | |
| 6,476,041 B1 | 11/2002 | Thompson et al. | |
| 6,498,170 B2 | 12/2002 | Sum et al. | |
| 6,559,146 B1 | 5/2003 | Annoura et al. | |
| 6,602,884 B2 | 8/2003 | Bacque et al. | |
| 6,693,099 B2 | 2/2004 | Degenhardt et al. | |
| 6,803,362 B2 | 10/2004 | Carruthers et al. | |
| 6,806,455 B2 | 10/2004 | Zarate et al. | |
| 6,809,093 B2 | 10/2004 | Degenhardt et al. | |
| 6,815,458 B2 | 11/2004 | Andersson et al. | |
| 6,815,465 B1 | 11/2004 | Makk et al. | |
| 2002/0082262 A1 | 6/2002 | Degenhardt et al. | |
| 2002/0091120 A1 | 7/2002 | Degenhardt et al. | |
| 2002/0115659 A1 | 8/2002 | Degenhardt et al. | |
| 2002/0119979 A1 | 8/2002 | Degenhardt et al. | |
| 2002/0128269 A1 | 9/2002 | Degenhardt et al. | |
| 2004/0132722 A1 | 7/2004 | Degenhardt et al. | |

FOREIGN PATENT DOCUMENTS

| | | |
|---|---|---|
| EP | 0363212 | 11/1990 |
| EP | 0529 395 | 3/1993 |
| EP | 0781 552 | 7/1997 |
| EP | 0812 830 | 12/1997 |
| EP | 0428 104 | 5/1999 |
| EP | 0428 107 | 5/1999 |
| FR | 2267104 | 11/1975 |
| FR | 2567885 | 1/1986 |
| GB | 2163150 | 2/1986 |
| GB | 2317 030 | 11/1998 |
| JP | 03-101662 | 4/1991 |
| JP | 04-283561 | 10/1992 |
| JP | 43-56466 | 12/1992 |
| JP | 05-148204 | 6/1993 |
| JP | 5-509303 | 12/1993 |
| JP | 06-506450 | 7/1994 |
| JP | 06-211664 | 8/1994 |
| JP | 06-510017 | 11/1994 |
| JP | 08-501573 | 2/1996 |
| JP | 09 12577 | 1/1997 |
| WO | WO 91/09846 | 7/1991 |
| WO | WO 92/01232 | 7/1992 |
| WO | WO 92/18478 | 10/1992 |
| WO | 93/05014 | 3/1993 |
| WO | WO 93/04042 | 3/1993 |
| WO | WO 94/04513 | 3/1994 |
| WO | WO 94/06771 | 3/1994 |
| WO | WO 94/07856 | 4/1994 |
| WO | WO 94/07858 | 4/1994 |
| WO | WO 94/11382 | 5/1994 |
| WO | WO 94/14809 | 7/1994 |
| WO | WO 94/17040 | 8/1994 |
| WO | WO 94/22846 | 10/1994 |
| WO | WO 95/05824 | 3/1995 |

| | | |
|---|---|---|
| WO | WO 95/26337 | 10/1995 |
| WO | WO 95/32975 | 12/1995 |
| WO | WO 95/32976 | 12/1995 |
| WO | WO 96/11677 | 4/1996 |
| WO | WO 96/15101 | 5/1996 |
| WO | WO 92/20190 | 7/1996 |
| WO | WO 96/20179 | 7/1996 |
| WO | WO 96/20180 | 7/1996 |
| WO | WO 96/36630 | 11/1996 |
| WO | WO 97/17069 | 5/1997 |
| WO | WO 97/26240 | 7/1997 |
| WO | WO 97/28166 | 8/1997 |
| WO | WO 97/34897 | 9/1997 |
| WO | WO 97/36869 | 10/1997 |
| WO | WO 97/45120 | 12/1997 |
| WO | WO 97/48689 | 12/1997 |
| WO | WO 97/48708 | 12/1997 |
| WO | WO 98/08822 | 3/1998 |
| WO | WO 98/22112 | 5/1998 |
| WO | WO 98/52923 | 5/1998 |
| WO | WO 98/30553 | 7/1998 |
| WO | 99/00387 | 1/1999 |
| WO | WO 99/10340 | 3/1999 |
| WO | WO 99/13871 | 3/1999 |
| WO | WO 99/24401 | 5/1999 |
| WO | WO 99/26921 | 6/1999 |
| WO | WO 99/43323 | 9/1999 |
| WO | WO 99/64001 | 12/1999 |
| WO | WO 99/65867 | 12/1999 |
| WO | WO 00/01714 | 1/2000 |
| WO | 00/18735 | 4/2000 |
| WO | WO 00/18733 | 4/2000 |
| WO | WO 00/32588 | 6/2000 |
| WO | WO 00/37458 | 6/2000 |
| WO | WO 00/50418 | 8/2000 |
| WO | WO 01/58891 | 8/2001 |
| WO | WO 01/74769 | 10/2001 |

OTHER PUBLICATIONS

Ambudkar, S. et al., "Biochemical Cellular, and Pharmacological Aspects of the multidrug transporter" Annu. Rev. Pharmacol. Toxicol., 39, p. 361-398, (1999).
Andrus, M. et al., "Total Synthesis of Stipiamide and designed Polyenes as new Agents for the Reversal of Multidrug Resistance", J. American Chemical Society, 119 p. 12159-12169 (1997).
Aszalos, A., "Modulation of Multidrug Resistance in Cancer by Immunosuppressive Agents" Pathology Oncology Research (1995) 1(1):64-70.
Atadja, P. et al., "PSC-833, a frontier in modulation of P-glycoprotein mediated multidrug resistance", Cancer and Metastasis Reviews, 17, p. 163-168, (1998).
Balaspiri, L. et al., "Preparation of some DI- and tripeptides containing optically active pipecolic acid as fragments of pipecolic acid-brandykinin analogues," Acta Physica et Chemica (1974) 20(1-2):105-110.
Barnes, K. et al., "Steroid Transport, accumulation, and antogonism of P-Glycoprotein in Multidrug resistant cells" Biochemistry, 35, p. 4820-4827, (1996).
Bates, S. et al., "New ABC Transporters in Multi-Drug Resistance," Emerging Therapeutic Targets, (2000) 4:5:561-580.
Bates, S. et al., "A Phase I/II Study of Infusional Vinblastine with the P-Glycoprotein Antagonist Valspodar (PSC 833) in Renal Cell Carcinoma," Clinical Cancer Res., (2004) 10:4724-4733.
Berger, D. et al., "Novel Multidrug Resistance Reversal Agents", Journal of Medicinal Chemistry, 42, p. 2145-2161, (1999).
Bhat, U. et al., "A structure-Function Relationship among Reserpine nd Yohimbine Analogues in Their Ability to Increase expression of mdrl and P-Glycoprotein in a human colon carcinoma cell line" Molecular Pharmacology, 48, p. 682-689 (1995).

Boer, R. et al., "Modulation to P-glycoprotein Mediated Drug Accumulation in Multidrug Resistant CCRF VRC-1000 Cells by Chemosensitisers" European Journal of Cancer, 32A, p. 857-861 (1996).
Bois, F. et al., "Halogenated Chalcones with High-Affinity Binding to P-Glycoprotein: Potential Modulators of Multidrug Resistance", Journal of Medicinal Chemistry, 41, p. 4161-4164 (1998).
Borrel, M. et al., "The effect of crown ethers, tetraalkylammonium slats, and polyoxyethylene amphiphiles on pirarubicin incorporation in K562 resistant cells" Biochemical Pharmacology, 50, p. 2069-2076 (1995).
Borst, P., "Multidrug resistance: A solvable problem?" Annals of Oncology (1999) 10(4):S162-S164.
Budworth, J. et al., "Comparison of Staurosporine and four analogues: their effects on growth, rhodamine 123 retention and binding to P-glycoprotein in multidrug resistant MCF-7/Adr cells" British Journal of Cancer, 73, p. 1063-1068 (1996).
Capolongo, L. et al., "Reversal of multidrug resistance by new dihydropyridines with low calcium antagonist activity" Acta Oncologia 33, p. 787-791 (1994).
Caponigro, F., "Protein kinase C: as worthwhile target for anticancer drugs?" Anti-Cancer Drugs (1997) 8:26-33.
Chaundhary, P. et al., "Induction of Multidrug Resistance in Human Cells by Transient Exposure to different Chemotherapeutic Drugs", Journal of the National Cancer Institute, 85, p. 632-639 (1993).
Chemical Abstracts, vol. 126, No. 13, Mar. 25, 1997, Columbus, OH US abstracts No. 171425s, MIWA, Tetsuo et al. "Prepration of carbapenems as antibacterials" abstract & JP 00 912557 (Takeda Chemical Industires Ltd.) Jan. 14, 1997 & Database CA Online Chemical Abstracts Service, Columbus OH, US, Database Accessession No. 126:171425, compound with RN 187265-36-7 and -37-8.
Chiba, P. et al., "Inhibitors of ABC-type Drug Efflux Pumps: an Overview of the Current Patent Situation," Expert Opin. Ther. Patents, (2004) 14:4:499-508.
Chiba, P. et al., "Structural Requirements for Activity of Propafenone-type Modulators in P-Glycoprotein-Mediated Multidrug Resistance." Molecular Pharmacology, 49, p. 1122-1130, (1996).
Chiba, P. et al., "Studies on Propafenone-type Modulators of Multidrug Resistance III: Variations on the Nitrogen", Quant. Struct.-Act. Relat. 16, p. 361-366 (1997).
Chiba, P. et al., "Studies on propafenone-type modulators of multidrug-resistance VI. Synthesis and pharmacological activity of compounds with varied spacer length between the central aromatic ring and the nitrogen atom" II Farmaco, 53, p. 357-364 (1998).
Chiba, P. et al., "Studies on Propafenone-type Modulators of Multidrug-resistance IV: Synthesis and Pharmacological Activity of 5-Hydroxy and 5-Benzyloxy", Arch. Pharm. Pharm. Med. Chem., 330, p. 343-347 (1997).
Chiba, P. et al., "Substituted 4-Acylpyrazoles and 4-Acylpyrazolones Synthesis and Multidrug Resistance-Modulating Activity" J. Med. Chem., 41, p. 4001-4011 (1998).
Chiba, P. et al., "Synthesis and Pharmacologcal activity of the stereoisomers of GP-88, a Propafenone-type modulator of Multidrug Resistance", Bioorganic & Medicinal Chemistry Lett, 8, pp. 829-832, (1998).
Chiba, P. et al., "Synthesis, Pharmacologic Activity, and Structure—Activity Relationships of a Series of Propafenone-related modulators of Multidrug Resistance", J. Med. Chemistry, 38, p. 2789-2793, (1995).
Choi, S. et al., "The bisbenzylisoquinoline alkaloids, tetrandien and fangchinoline, enhance the cytotoxicity of multidrug resistance-related drugs via modulation of P-glycoprotein." Anti-Cancer Drugs, 9, p. 255-261 (1998).
Chou, T. et al., "Reversal of anticancer multidrug resistance by the ardeemins" Proc. Natl. Acad. Sci., 95, p. 8369-8374, (1998).
Christensen, J. et al., "Reversal of multidrug resistance by derivatives of acrivastine: a study of structure-activity relationships of P-glycoprotein inhibitors in vitro and in vivo" Oncology Reports, 4, p. 1353-1360 (1997).
Christensen, J. et al., "Reversal of multidrug resistance in vivo by dietary administration of the phytochemical Indole-3-Carbinol", Cancer Research, 56, p. 574-581, (1996).

Conseil, G. et al., "Flavonoids: A class of modulators with bifunctional interactions at vicinal ATP- and steroid-binding sites on mouse P-glycoprotein", PNAS, 95, p. 9831-9836, (1998).

Dale, I et al., "Reversal of P-glycoprotein-mediated multidrug resistance by XR9051, a novel diketopiperazine derivative" British Journal of Cancer, 78, p. 885-892 (1998).

Dantzig, A. et al., "Reversal of P-Glycoprotein-mediated Multidrug Resistance by a Potent Cyclopropyldibenzosuberance Mudulator, LY335979" Cancer Research, 56, p. 4171-4179, (1996).

Dantzig, A. et al., "Selectivity of the multidrug resistance modulator, LY335979 for P-glycoprotein and effect on cytochrome P-450 Activities," J Pharm. Exp Therapeutics (1999) 290(2):854-862.

"DCTD Tumor Repository, a cataloge of in vitro cell lies and transplantable animal and human tumors," (2003).

De Jong, G. et al., "Modulation of Doxorubicin Resistance in P388/ADR Cells by Ro44-5912, a Tiapamil Derivative" Anticancer Research, 15, p. 911-916 (1995).

De Milito, A. et al., "Proton Pump Inhibitors May Reduce Tumour Resistance," Expert Opin. Pharmacother., (2005) 6:7:1049-1054.

Dellinger, M. et al., "Structural Requirements of Simple Organic Cations for Recognition by Multidrug-resistant cells", Cancer Research, 52, p. 6385-6389, (1992).

Demeule, M. et al., "Molecular Interactions of Cyclosporin A with P-glycoprotein" The Journal of Biological Chemistry, 272, p. 6647-6652 (1997).

Demeule, M. et al., "Inhibition of P-glycoprotein by cyclosporin A analogues and metabolites," Biochem. Cell Biol. (1999) 77:47-58.

Desrayaud, S. et al., "Effect of the Mdr1a P-Glycoprotein Gene disruption on the tissue distribution of SDZ PSC 833, a multidrug Resistance-Reversing Agent, In Mice." The Journal of Pharmacology and Experimental Therapeutics, 285, p. 438-443 (1998).

Dey, S. et al., "A single amino acid residue contributes to distinct mechanisms of inhibition of the human multidrug transporter by steroisomers of the dopamine receptor antogonist flupentixol." Biochemistry, 38, p. 6630-6639 (1999).

Dey, S. et al., "Evidence for two nonidentical drug-interaction sites in the human P-glycoprotein", Proc. Natl. Acad. Sci., 94, p. 10594-10599 (1997).

Dhainaut, A. et al., "New Purines and Purine Analogs as Modulators of Multidrug Resistance", J. Med. Chem., 39, p. 4099-4108, (1996).

Dhainaut, A. et al., "New Triazine derivatives as Potent Modulators of Multidrug Resistance", Journal of Medicinal Chemistry, 35, p. 2481-2496, (1992).

Di Pietro, A. et al., "P-glycoprotein-mediated resistance to chemotherapy in cancer cells: using recombinant cytosolic domains to establish structure-function relationships" Brazilian J. Med. Biol. Research, 32, p. 925-939 (1999).

Dinh, T. et al., "Design, Synthesis, and Evaluation of the Multidrug Resistance-Reversing activity of D-Glucose Mimetics of Hapalosin", J. Med. Chem., 41, p. 981-987 (1998).

Dinh, T. et al., "Synthesis, Conformational Analysis, and Evaluation of the Multidrug Resistance-Reversing Activity of the Triamide and Proline Analogs of Hapalosin", J. of Organic Chemistry, 62, p. 6773-6783, (1997).

Drewe, J. et al., "HIV Protease Inhibitor Ritonavir: A more potent inhibitor of P-glycoprotein than the cyclosporine analog SDZ PSC 833," Biochem. Pharm. (1999) 57:1147-1152.

Ecker, G. et al., "Structure—Activity Relationship Studies on Benzofuran Analogs of Propafenone-type Modulators of Tumor Cell Multidrug Resistance", Journal of Medicinal Chemistry, 39, p. 4767-4774 (1996).

Ecker, G. et al., "The importance of a nitrogen atom in modulators of multidrug resistance," Molecular Pharmacology (1999) 56:791-796.

Eliason, J. et al., "Novel Dithiane analogues of tiapamil with high activity to overcome multidrug resistance in vitro", Biochemical Pharmacology, 50, p. 187-196, (1995).

Emmer, G. et al., "Derivatives of a Novel Cyclopeptolide. 2. Synthesis, Activity against Multidrug Resistance in CHO and KB cells in Vitro, and Structure-Activity Relationships", Journal of Medicinal Chemistry, 37, p. 1918-1928 (1994).

Etievant, C. et al., "Requirements for P-glycoprotein recognition based on structure-activity relationships in the podophyllotoxin series" Anti-Cancer Drug Design 13, p. 317-336 (1998).

Fan, D. et al., "Reversal of multidrug resistance in murine fibrosarcoma cells by thioxanthene flupentixol" Investigational New Drugs, 12, p. 185-195, (1994).

Ferté, J. et al., "Flavonoid-Related Modulators of Multidrug Resistance: Synthesis, Pharmacological Activity, and Structure—Activity Relationships", J. Med. Chemistry, 42, p. 478-489 (1999).

Fields, A. et al., "PSC833: initial clinical results in refractory ovarian cancer patients" Current Opinion in Oncology, 10, p. S21 (1998).

Ford, J. et al., "Cellular and Biochemical Characterization of Thioxanthesnes for Reversal of Multidrug resistance in Human and Murine Cell Lines", Cancer Research, 50, p. 1748-1756, (1990).

Ford, J. et al., "Structural Features Determining Activity of Phenothiazines and Related Drugs for Inhibition of Cell Growth and Reversal of Multidrug resistance", Molecular Pharmacology, 35, p. 105-115 (1989).

Ford, J. et al., "Pharmacologic circumvention of multidrug resistance," Cytotechnology (1993) 12:171-212.

Frappier, F. et al., "Bisbenzylisoquinolines as Modulators of Chloroquine Resistance in Pasmodium falciparum and multidrug resistance in Tumor cells" Antimicrobial Agents and Chemotherapy, June, p. 1476-1481, (1996).

Fukushima, T et al., "Effect of PSC 833 on the cytotoxicity of idarubicin and idarubicinol in the multidrug-resistant K562 cells", Leukemia Research, 23, p. 37-42, (1999).

Garrigos, M. et al., "Competitive and non-competitive inhibition of the multidrug-resistance-associated P-glycoprotein ATPase further experimental evidence for a multisite model" Euro J. Biochem. 244, p. 664-673 (1997).

Gekeler, V. et al., "Effects of the selective bisindolymalkeimide protein kinase C inhibitor GF109203X on P-glycoprotein-mediated multidrug resistance" British Journal of Cancer, 74, p. 897-905 (1996).

Gekeler, V. et al., "The specific bisindolymaleimide PKC-inhibitor GF 109203x efficiently modulates MRP-Associated Muliple drug resistance", Biochemical and Biophysical research communications, 206, p. 119-126, (1995).

Germann, U. et al., "Cellular and biochemical characterization of VX-710 as a chemosensitizer: reversal of P-glycoprotein-mediated multidrug resistance in vitro" Anti-cancer drugs, 8, p. 125-140 (1997).

Germann, U. et al., "Chemosensitization and drug accumulation effects of VX-710, verapamil, cyclosporin A, MS-209 and GF120918 in multidrug resistant HL60/ADR cells expressing the multidrug resistance-associated protein MRP" Anti-Cancer Drugs, 8, p. 141-1.

Greenberger, L. et al., "A-(3,4-Dimethyoxyphenyl)-3,4-dihydro-6,7-dimethoxy-a-[(4-methylpheynl)thiol]-2(1H)-iso-quinolineheptanenitrile (CL329,753): A Novel Chemosensitizing Agent for P-Glycoprotein-Mediated Resistance with Improved Biological Properties Compared with Verapamiladn Cyclosporin A" Oncology Research, 8 207-218 (1996).

Greene et al., Protecting Groups in Organic Synthesis, 2nd Ed. Wiley & Sons, Inc. (1991) p. 5, lines 23-27.

Grey, M. et al., "Effect on cell kill of addition of multidrug resistance modifiers cyclosporin A and PSC 833 to cytotoxic agents in chronic lymphocytic leukaemia" Leukemia Research, 23, p. 29-35 (1999).

Hait, W. et al., "Rational design and pre-clinical pharmacology of drugs for reversing multidrug resistance" Biochemical Pharmacology, 43, p. 103-107, (1992).

He, H. et al., "Fumitremorgin C Analogs that reverse mitoxantrone resistance in human colon carcinoma cells," Med. Chem. Res. (1999) 9:424-437.

Hegewisch-Becker, S. "MDR1 Reversal: Criteria for clinical trials designed to overcome the multidrug resistance phentype," Leukemia (1996) 10(3):S32-S38.

Hegewisch-Becker, S. "The MDR phenotype in menatologic malignancies" prognostic relevance and future perspectives, Ann. Hematol. (1996) 72:105-117.

Hemenway, C. et al., "immunosuppressant Target Protein FKBP12 Is Required for P-Glycoprotein Function in Yeast", The Journal of Biological Chemistry, 271, pp. 18527-18534 (1996).

Hidaka, H. et al., "Isoquinolinesulfonamides, Novel and Potent Inhibitors of Cyclic Nucleotide dependent Protein Kinase and Protein Kinase C", Biochemistry, 23, p. 5036-5041, (1984).

Hill, B. et al., "Evaluation of S9788 as a Potential Modulator of Drug Resistance against Human Tumour Sublines Expressing Differing Resistance Mechanisms in vitro" Int. J. Cancer, 55, p. 330-337 (1993).

Hofmann, J. et al., "Mechanism of action of dexniguldipine-HC1 (B8509-035), a new potent modulator of multidrug resistance" Biochemical Pharmacology, 49, p. 603-609 (1995).

Hooijberg, J. et al., "Potent interaction of flavopiridol with MRP1," British Journal of Cancer (1998) 81(2):269-276.

Hooijberg, J., et al., "Modulation by (iso)flavonoids of teh ATPase activity of the multidrug resistance protein" FEBS Letters, 413, 344-348, (1997).

Horton, J. et al., "Pharmacological Characterization of N-Substituted Phenoxazines Directed toward reversing vinca alkaloid resistance in multidrug-resistant cancer cells", Molecular Pharmacology, 44, p. 552-559, (1993).

Hosoyama, H. et al., "Modulation of Multidrug Resistance in Tumor Cells by Taxinine derivatives" Bioorganic & Medicinal Chemistry Letters, 9, p. 389-394, (1999).

Hurwitz, L. et al., "Can prenylcysteines be exploited as ligands for mammulian multidrug-resistance transorters?" Chemistry & Biology, 4, p. 711-715 (1997).

Jachaz, B. et al., "SDZ 280-125: a cyclopeptolide endowed with an In vitro cyclosporin A-like profile of activity for the reversion fo the P-glycoprotein-mediated multidrug resistance of tumor cells", Anti-Cancer Drugs, 5, p. 313-320 (1994).

Jachez, B. et al., "Reversion of the P-glycoprotein-mediated multidrug resistance of cancer cells by FK-506 derivatives", Anticancer Drugs, 4, p. 223-229 (1993).

Kadam, S. et al., "Reversal of Multidrug Resistance by Two Novel Indole Derivatives", Cancer Research, 52, p. 4735-4740, (1992).

Kam, T. et al., "Reversal of Multidrug resistance (MDR) by aspidofractinine-type indole alkaloids", Bioorganic & Medicinal Chemistry Letters, 8, p. 2769-2772, (1998).

Kavallaris, M., "The role of multidrug resistance-associated protein (MRP) expression in multidrug resistance," Anti-Cancer Drugs (1997) 8:17-25.

Kim, A. et al., "Saquinavir, an HIV Protease Inhibitor, Is Transported by P-Glycoprotein" The Journal of Pharmacology and Experimental Therapeutics, 286, p. 1439-1445 (1998).

Kim, E. et al., "A New Sesquiterpene Ester from Celastrus orbiculatus Multidrug Resistance in cancer Cells" J. Nat. Prod., 61, p. 108-111 (1998).

Kim, S. et al., "Circumvention of drug resistance in cancer cells by a new fluoropyridmidine analogue" Experimental and molecular Medicine, 28, p. 119-123, (1996).

Kim, S. et al., "Sesquiterpene Esters from Calastrus orbiculatus and their structure-activity relationship on the modulation of multidrug resistance" J. Nat. Prod., 62, p. 697-700, (1999).

Kirk, J. et al., "Reversal of P-glycoprotein-mediated multidrug resistance by pure anti-oestrogens and novel tamoxifen derivatives," Biochemical Pharmacology, 48, p. 277-285, (1994).

Kiue, A. et al., "Activities of Newly Synthesized Dihydropyridines in Overcoming of Vincristine Resistance, Calcium Antagonism, and Inhibition of Photoaffinity labeling of P-Glycoprotein in Rodents" Cancer Research, 50, p. 310-317, (1990).

Klopman, G. et al., "Quantitative Structure-Activity Relationship of Multidrug-Resistance Reversal Agents" Molecular Pharmacology, 52, p. 323-334 (1997).

Klopman, G. et al., "Structure-Activity study and Design of Multidrug-resistant Reversal Compounds by a Computer Automated Structure Evaluation Methodology" Cancer Research, 52, p. 4121-4129 (1992).

Kobayashi, J. et al., "Effects of Taxoids from taxus cuspidata on microtuble depolymerization and vincristine accumulation in MDR cells", Bioorganic & Medicinal Chemistry Letters 7, p. 393-398 (1997).

Kobayashi, J. et al., "Modulation of the Multidrug Resistance by a Taxuspine C and Other Taxoids from Japanese Yew", Bioorganic & Medicinal Chemistry Letters 8, p. 1555-1558, (1998).

Kovacs, G. et al., "Antiamnesic effects of D-pipecolic acid and analogues of Pro-Leu-Gly-NH2 in rats", Pharm. Biochem. Behavior (1989) 31:833-837.

Kraus-Berthier, L. et al., "InVivo reversal of multidrug resistance by two new dihydropyridine derivatives, S16317 and S16324." Acta Oncologia, 33, p. 631-637, (1994).

Kwon, Y et al., "Inhibitors of P-Glycoprotein-mediated Daunomycin Transport in Rat Liver Canalicular Membrane Vesicles" Journal of Pharmaceutical Sciences, 85, p. 935-939, (1996).

Lee, I. et al. "Protease Inhibitors and the MDR1 Multidrug Transporter" The Journal of Clinical Investigation, 101, p. 287-288 (1998).

Legrand, O. et al., "Neoplasia: Simultaneous Activity of MRP1 and Pgp is Correlated with in vitro resistance to Daunorubicin and with in vivo resistance in Adult Acute Myeloids Leukemia" Blood, 94, p. 1046-1056 (1999).

Lehne, G. et al., "Growth inhibition, cytokinesis failure and apoptosis of multidrug-resistant leukemia cells after treatment with P-glycoprotein inhibitory agents," Leukemia (1999) 13:768-778.

Lehnert, M. et al., "Phase II trial of dexverapamil and epirubicin in patients with non-responsive metastitic breast cancer" British Journal of Cancer 77, p. 1155-1163 (1998).

Leith, C. et al., "Neoplasia: Frequency and Clinical Significance of the Expression of the Multidrug resistance proteins MDR1/P-Gloycoprotein, MRP1, and LRP in Acute Myeloid Leukemia. A Southwest Oncology Group Study," Blood, 94, pp. 1086-1099 (1999).

Li, X. et al., "Role of Efflux Pump(s) in Intrinsic Resistance of Pseudomonas aeruginosa: Active Efflux as a contributing Factor a B-Lactam Resistance" Antimicrobial Agents and Chemotherapy, 38, p. 1742-1752 (1994).

Litman, T. et al., "Structure-activity relationships of P-glycoprotein interacting drugs: kinetic characterization of their effects on ATPase activity" Biochimica et Biophysica Acta, 1361, p. 159-168, (1997).

Liu, Z. et al., "BIBW22 BS, Potent Multidrug resistance-Reversing Agent, Binds directly to P-Glycoprotein and Accumulates in Drug-Resistant Cells", Molecular Pharmacology, 50, p. 482-492, (1996).

Loe, D.W. et al., "Structure Activity Studies of Verapamil Analog that Modulate Transport of Leukotriene C4 and Reduced Glutathione by Multidrug Resistance Protein MRP1," Biochem. Biophys. Res. Commun., 275, 2000, 795-803.

Loo, T. et al., "The transmembrane domains of the human multidrug resistance P-glycoprotein are sufficient to mediate drug binding and trafficking to the cell surface." The Journal of Biological Chemistry, 274, p. 24759-24765, (1999).

Loor, F., "Cyclosporins and Related Fungal Products in the Reversal of P-Glycoprotein-mediated Multidrug resistance" Multidrug Resistance in Cancer Cells, Ch. 26, 385-412 (1996) (Book—Not Included).

Loor, F., "Valspodar: Current status and Perspectives," Expert Opin. Invest Drugs (1999) 8(6):807-835.

Lum, B. et al., "Molecular Targets in Oncology: Implications of the Multidrug Resistance Gene," Pharmacotherapy (1993) 13(2):88-109.

Mackie et al., Guidebook to Organic Synthesis, 2nd Ed. Wiley & Sons, Inc. (1991) (Book —Not Provided).

Martin, J., "Enantioselective protonation of amide enolates derived from piperidine-2-carboxylic acid," Tetrahedron Lett. (1997) 38(41):7181-7182.

Matsuzaki, J. et al., "Contribution of P-glycoprotein to Bunitrolol Efflux across Blood-Brain Barrier" Biopharmaceutics and Drug Disposition, 20, p. 85-90(1999).

Mátyus, P. et al., "Novel pyridazino[4,5-b][1,5]oxazepines and -thiazepines as 5-HT1A receptor ligands," Bioorg. Med. Chem. Lett., 7(22), 2857-2862 (English) 1997.

Mealey, K. et al., "Immunosuppressant inhibition of P-glycoprotein function is independent of drug-induce suppression of Peptide-prolyl isomerase and calcineurin activity" Cancer Chemother Pharmacol, 44, p. 152-158, (1999).

Mendez-Vidal, C., et al., "Reversal of P-glycoprotein-mediated multidrug resistance in vitro by AV200, a new ardeemin derivative" Cancer Letters, 132, 45-50 (1998).

Merck Index, 12.sup.th Ed., Baduvari, Susan, Ed., 1996, Whitehouse Station, NJ, entry #10303.

Merritt, J. et al., "The bisindolylmaleimide protein kinase C inhibitor, Ro 32-2241, reverses multidrug resistance in KB tumor cells", Cancer Chemother Pharmacol, 43, p. 371-378, (1999).

Molnár, J. et al., "Inhibition of the Transport Function of Membrane Proteins by Some Substituted Phenothiazines in *E. coli* and Multidrug Resistant Tumor Cells" Anticancer Research, 17, p. 481-486 (1997).

Morihira, K. et al., "Synthesis and Evaluation of Artifical Taxoids with Antitumor and Multi-Drug resistance Reversing Activities", Bioorganic & Medicinal Chemistry Letters, 8, p. 2977-2982 (1998).

Morihira, K. et al., "Synthesis of C-Ring Aromatic Taxoids and Evaluation of Their Multi-Drug Resistance reversing activity", Bioorganic & Medicinal Chemistry Letters 8, p. 2973-2976, (1998).

Motohashi, N. et al., "Drug Resistance Reversal, Anti-mutagenicity and Antiretroviral Effect of Phthalimido-and Chloroethyl-Phenothiazines" Anticancer Research, 17, p. 3537-3544 (1997).

Naito, M. et al., "New Multidrug-resistance-reversing drugs, MS 209 and SDZ PSC 833," Cancer Chemother Pharmacol (1997) 40:S20-S24.

Naito, S. et al., "Development of Novel Reversal Agents, Imidazothiazole Derivatives, targeting MDR1- and MRP-Mediated Multidrug Resistance." Oncology Research, 10, p. 123-132 (1998).

Nakamura, S. et al., "Effects of Isoquinolinesulphonamide Compounds on Multidrug-resistant P388 cells" J. Pharm. Pharmacol 45, p. 268-273 (1993).

Nakamura, S. et al., "Inhibition of P-Glycoprotein-Dependent Multidrug Resistance by an Isoquinolinesulfonamide Compound H-87 in Rat Ascites Hepatoma AH66 Cells" Biol. Pharm. Bull., 19, p. 886-889, (1996).

Nakanishi, O. et al., "Potentiation of the Antitumor Activity by a Novel Quinoline Compound, MS-209, in Multidrug-Resistant Solid Tumor Cell Lines", Oncology Research, 9, p. 61-69 (1997).

Narasaki, F. et al., "A novel quinoline derivative, MS-209, overcomes drug resistance of human lung cancer cells expressing the multidrug resistance-associated protein (MRP) gene" Cancer Chemother Pharmacol, 40, p. 425-432 (1997).

Newman, R. et al., "MDL 201307: a novel benzothiazepine modulator of multiple dru resistance" Journal of Experimental Therapeutics & Oncology, 1, p. 109-118 (1996).

Nogae, I. et al., "Analysis of structural features of dihydropyridine analogs needed to reverse multidrug resistance and to inhibit photoaffinity labeling of P-glycoprotein", Biochemical Pharmacology, 38, p. 519-527, (1989).

Norman, B. "Inhibitors of MRP1-mediated multidrug resistance" Drugs of the Future, 23, p. 1001-1013 (1998).

Norman, B. et al., "Reversal of Resistance in multidrug resistance protein (MRP1)-overexpressing cells by LY329146," Bio. Med. Chem. Let., (1999) 9:3381-3386.

Oberlies, N. et al., "Structure—Activity Relationships of Diverse Annonaceous Acetogenins against Multidrug Resistant Human mammary Adenocarcinoma (MCF-7/Adr) Cells", Journal of Medicinal Chemistry, 40, p. 2102-2106, (1997).

O'Connell, C. et al., "Synthesis and Evaluation of Hapalosin and analogs as MDR-Reversing agents" Bioorganic & Medicinal Chemistry Letters, 9, p. 1541-1546 (1999).

Ogino, J. et al., "Dendroamides, New Cyclic Hexapeptides from a Blue-Green Alga. Multidrug-Resistance Reversing activity of dendroamide A." J. Nat. Prod., 59, p. 581-586 (1996).

Ojima, I. et al., "Designing taxanes to treat multidrug-resistant tumors," Modern Drug Discovery (1999) 45-52.

Okuno, T. et al., "Chemical Study on Hepalosin, a Cyclic Depsipeptide Possessing Multidrug Resistance Reversing activities: Synthesis, Structure and Biological Activity" Tetrahedron, 52, p. 14723-14734 (1996).

Pajeva, I. et al., "A Comparative Molecular Field Analysis of Propafenone-type Modulators of Cancer Multidrug Risistance", Quant. Struct.—Act. Relat., 17, p. 301-312, (1998).

Pajeva, I. et al., "Molecular Modeling of Phenothiazines and Related Drugs as multidrug resistance modifiers: A Comparative molecular field analysis study" Journal of Medicinal Chemistry, 41, p. 1815-1826 (1998).

Pajeva, I. et al., "QSAR and Molecular Modelling of Catamphiphilic Drugs Able to Modulate Multidrug resistance in Tumors" Quant. Struct.—Act. Relat., 16, p. 1-10 (1997).

Patel, N. and Rothenberg, M., "Multidrug resistance in cancer chemotherapy," Investigational New Drugs (1994) 12:1-13.

Payen, L. et al., "Reversal of MRP-Mediated Multidrug Resistance in Human lung Cancer Cells by the Antiprogestatin Drug RU486" Biochemical and Biophysical Research Communications, 258, p. 513-518, (1999).

Pearce, H. et al., "Essential features of the P-glycoprotein pharmacophore as defined by a series of reserpine analogs that modulate multidrug resistance", Proc. Natl. Acad. Sci., 86, p. 5128-5132 (1989).

Pearce, H. et al., "Structural characteristics of compounds that modulate P-Glycoprotein-associated multidrug resistance" Advances in Enzyme Regulations, 30, p. 357-373, (1990).

Pereira, E. et al., "Reversal of Multidrug Resistance by Verapamil analogues", Biochemical Pharmacology, vol. 50,No. 4, p. 451-457, (1995).

Pfister, J. et al., "Methanodibenzosuberylpiperazines as Potent Multidrug Resistance Reversal Agents" Bioorganic & Medicinal Chemistry Letters, 5, p. 2473-2476 (1995).

Pommerenke, E. et al., "Activity of various amphiphilic agents in reversing multidrug resistance of L1210 cells", Cancer Letters, 55, p. 17-23, (1990).

Pourtier-Manzanedo, A. et al., "SDZ PSC 833 and SDZ 280-446 are the most active of various resistance-modifying agents in restoring rhodamine-123 retention within multidrug resistant P388 cells" Anti-Cancer Drugs, 3, p. 419-425 (1992).

Prost, S., "Mechanisms of Resistance to Topoisomerases Poisons," Gen. Pharmac. (1995) 26(8):1773-1784.

Pusztai, L. et al., "Phase II Study of Tariquidar, a Selective P-Glycoprotein Inhibitor, in Patients with Chemotherapy-Resistant, Advanced Breast Carcinoma," Cancer, (2005) 104:4:682-691.

Ramu, A. et al., "Reversal of multidrug resistance by bis(phenylalkyl)amines and structurally related compounds," Cancer Chemother Pharmacol (1994) 34:423-430.

Ramu, A. et al., "Reversal of multidrug resistance by phenothiazines and structurally related compounds," Cancer Chemother Pharmacol (1992) 30:165-173.

Ramu, N. et al., "Circumvention of Adriamycin Resistance Dipyridamole Analogues: a structure-activity relationship study" Int. J. Cancer, 43, p. 487-491, (1989).

Rao, U. et al., "Direct Demonstration of High affinity Interactions of Immunosuppressant Drugs with the Drug Binding Site of the Human P-Glycoprotein" Molecular Pharmacology, 45, p. 773-776, (1994).

Regina, A. et al., "Dexamethasone regulation of P-glycoprotein activity in an immortalized rat brain endothelial cell line, GPNT," J Neurochem (1999) 73(5):1954-1963.

Renau, T. et al., "Chapter 12. Antimicrobial Potentiation Approaches: Targets and Inhibitors" Annual Reports in Medicinal Chemistry, 33, p. 121-129 (1998).

Robert, J., "Multidrug resistance in oncology: diagnostic and therapeutic approaches," Eur. J. Clin. Invest. (1999) 29:536-545.

Robert, J. "Multidrug resistance reversal agents" Drugs of the Future, 22, p. 149-158 (1997).

Robert, J. "Proposals for Concomitant Use of several modulators of Multidrug Resistance in Clinics" Anticancer Research, 14, p. 2371-2374 (1994).

Roe, M. et al., "Reversal of P-Glycoprotein Mediated Multidrug Resistance by Novel Anthranilamide Derivatives", Bioorganic & Medicinal Chemistry Letter, 9, pp. 595-600, (1999).

Saeki, T. et al., "Human P-glycoprotein transports Cyclosporin A and FK506" The Journal of Biological Chemistry 268 p. 6077-6080 (1993).

Safa, A. "Photoaffinity Labels for Characterizing Drug Interaction Sites of P-Glycoprotein" Methods in Enzymology, 292, p. 289-307 (1998).

Sanglard, D. et al., "Mechanisms of Resistance to azole Antifungal Agents in Candida albicans Isolates from AIDS Patients Involved Specific Multidrug Transporters" Antimicrobial Agents and Chemotherapy, 39, p. 2378-2386 (1995).

Sarkadi, B. et al., "Interaction of bioactive hydrophobic peptides with the human multidrug transporter", The FASEB Journal, 8, p. 766-770, (1994).

Sarkadi, B. et al., "Search for specific inhibitors of multidrug resistance" Seminars in Cancer biology, 8, 1997, 171-182.

Sarkadi, B. et al., "Expression of the Human Multidrug Resistance cDNA in Insect Cells Generates High Activity Drug-stimulated Membrane ATPase," J. Biological Chemistry (1992) 267(7):4854-4858.

Sato, S. et al., "Potentiation of vincristine and antinomycin D by a new synthetic imidazole anti-tumor agent YM534 active against human cancer cells and multidrug-resistant cells" Anti-Cancer Drug Design, 4, p. 125-135, (1989).

Sato, W. et al., "Reversal of multidrug resistance by a novel quinoline derivative, MS-209", Cancer Chemother Pharmacol, 35, p. 271-277 (1995).

Sato, Y. et al., "Studies on new β-adrenergic blocking agents. I. Synthesis and pharmacology of coumarin derivatives," Chem. Pharm. Bull., 20(5), 905-17 (English) 1972.

Sawanishi, H. et al., "Novel inhibitors for Multidrug Resistance: 1,3,5-Triazacycloheptanes", J. Med. Chem. 38, p. 5066-5070, (1995).

Sawanishi, H. et al., "Structure-activity Relationships of Diamines, Dicarboxamides, and Disulfonamides on Vinblastine accumulation in P388/ADR Cells", Chem. Pharm. Bull. 7, p. 1459-1462, (1994).

Scala, S. et al., "P-Glycoprotein Substrates and Antagonists Cluster into Two Distinct Groups" Molecular Pharmacology, 51, p. 1024-1033 (1997).

Seelig, A. "A general pattern for substrate recognition by P-Glycoprotein" Eur. Journal Biochem., 251, p. 252-261 (1998).

Seprödi, J. et al., "Peptide derivatives Against Multidrug Resistance" Peptides, Proceedings of the 24.sup.th European Peptide Symposium, p. 801-802, (1996).

Shah, A. et al., "6,12-Dihydro-1-benzopyrano [3,4-b][1,4] benzothiazin-6-ones: Synthesis and mdr Reversal in Tumor Cells" Anticancer Research, 18, p. 3001-3004 (1998).

Sharom, F. et al., "Linear and cyclic peptides as substrates and modulators of P-glycoprotein: peptide binding and effects on drug transport and accumulation" Biochem. Journal, 333, pp. 621-630 (1998).

Sharom, F. et al., "Spectroscopic and biophysical approaches for studying the structure and function of the P-glycoprotein multidrug transporter" Biochem. Cell Biol., 76, p. 695-708 (1998).

Sharom, F. et al., "Synthetic hydrophobic peptides are substrates for P-Glycoprotein and stimulate drug transport" Biochem. J. 320, p. 421-428 (1996).

Shrivastava, P. et al., "Circumvention of multidrug resistance by a quinoline derivative, MS-209, in multidrug-resistant human small-cell lung cancer cells and its synergistic interaction with cyclosporin A or verapamil" Cancer Chemother Pharmacol 42, 483-490 (1996).

Simon, S. et al., "Cell biological mechanisms of multidrug resistance in tumors," Proc. Natl. Acad. Sci. USA (1994) 91:3497-3504.

Sinha, B., "Topoisomerase Inhibitors, A review of their therapeutic potential in cancer," Drugs (1995) 49(1):11-19.

Smith, A. et al., "Availability of PSC833, a Substrate and Inhibitor of P-Glycoproteins, in Various Concentrations of Serum" Journal of the National Cancer Institute, 90, p. 1161-1166, (1998).

Smith, C. et al., "Welwitindolinone Analogues that reverse P-Glycoprotein-Mediated Multiple drug Resistance", Molecular Pharmacology, 47, p. 241-247, (1995).

Sonneveld, P., "Drug resistance in Multiple Myeloma," Pathologie et Biologie (1999) 47(2):182-187.

Sonneveld, P. and Wiemer, E., "Inhibitors of multidrug resistance," Current Opinion in Oncology (1997) 9:543-548.

Sparreboom, A., et al., "Clinical pharmacokinetics of doxorubican in combination with GF120918, a potent inhibitor of MDR1 P-glycoprotein," Anti-Cancer Drugs (1999) 10:719-728.

Stark, H. et al., "Enzyme-catalyzed prodrug approaches for the histamine H3-receptor agonist (R)-α-methylhistamine," Bio. Med. Chem. (2001) 9:191-198.

Starling, J. et al., "Pharmacological Characterization of LY335979: A Potent Cyclopropyldibenzosuberane Modulator of P-Glycoprotein" Advan. Enzyme Regul., 37, p. 335-347, (1997).

Suzuki, T. et al., "Structure-Activity Relationship of Newly Synthesized Quinoline derivatives for Reversal of Multidrug Resistance in Cancer" J. Med. Chem., 40, p. 2047-2052 (1997).

Suzuki, T. et al., "Synthesis of Glucuronides of multidrug resistance Reversing Drug MS-209" Bioorganic & Medicinal Chemistry Letters, 9, pp. 659-662 (1999).

Takeshita, H. et al., "Avoidance of Doxorubicin Resistance in Osteosarcoma Cells Using a New Quinoline Derivative, MS-209" Anticancer Research, 18, p. 739-742 (1998).

Tanabe, H. et al., "Newly Synthesized Dihydropyridine Derivatives as Modulators of P-Glycoprotein-mediated Multidrug Resistance", Bioorganic & Medicinal Chemistry Letters, 6, p. 2219-2227 (1998).

Tanaka, K. et al., "Effect of Cyclosporin Analogues and FK506 on Transcellular Transport of Daunorubicin and Vinblastine via P-glycoprotein" Pharmaceutical Research, 13, p. 1073-1077 (1996).

Tasaka, S et al., "Synthesis of 2-Phenylimidazo [2,1-b]benzothiazole Derivatives as Modulators of Multidrug Resistance for Tumor Cells", J. Heterocyclic Chem., 34, p. 1763-1767 (1997).

Teodori, E. et al., "Design, Synthesis, and in Vitro Activity of Catamphiphilic reverters of Multidrug Resistance: Discovery of a Selective, Highly Efficiaious Chemosensitizer with Potency in the Nanomolar Range" J. Med. Chem., 42, p. 1687-1697, (1999).

Thimmaiah, K et al., "Characterization of 2-Chloro-N.sup.10 -Substituted Phenoxazines for Reversing Multidrug Resistance in Cancer cells" Oncology Research, 10, p. 29-41, (1998).

Thimmaiah, K. et al., "Structural Determinants of Phenoxazine Type Compounds Required to Modulate the Accumulation of Vinblastine and Vincristine in Multidrug-resistant cell lines" Cancer Communications, 2, p. 249-259, (1990).

Thimmaiah, K. et al., "Synthesis and Chemical Characterization of N-Substituted Phenoxazines Directed toward Reserving Vinca Alkaloid Resistance in Multidrug-Resistance Cancer Cells", Journal of Medicinal Chemistry, 35, p. 3358-3364, (1992).

Thomas, H. et al., "Overcoming Multidrug Resistance in Cancer: An Update on the Clinical Strategy of Inhibiting P-Glycoprotein," Cancer Control, (2003) 10:2:159-165.

Tiberghien, F. et al., "Ranking of P-glycoprotein substrates and inhibitors by a calcein-AM fluorometry screening assay" Anti-Cancer Drugs, 7, p. 568-578 (1996).

Tmej, C. et al., "A Combined Hansch/Free-Wilson Approach as Predictive Tool in QSAR Studies on Propafenone-Type Modulators of Multidrug Resistance" Arch. Pharm. Med. Chem., 331, p. 233-240 (1998).

Toffoli, G. et al., "Reversal activity of Cyclosporin A and its metabolites M1, M17 and M21 in Multidrug-resistant cells" Int. J. Cancer, 71, p. 900-906 (1997).

Toffoli, G. et al., "Structure-Activity relationship of verapamil analogs and reversal of multidrug resistance" Biochemical Pharmacology, 50, p. 1245-1255, (1995).

Tsuruo, T. and Tomida, A., "Multidrug Resistance" Anti-Cancer Drugs (1995) 6:213-218.

Tunggal, J. et al., "Influence of cell concentration in limiting the therapeutic benefit of P-glycoprotein reversal agents" Int. J. Cancer, 81, p. 741-747 (1999).

Twentyman, P. et al., "Effects of cyclosporin A and a non-immunosuppresive analogue, O-acetyl cyclosporin A, upon a growth of parent and multidrug resistant human lung cancer cells in vitro", Br. J. Cancer, 65, p. 335-340 (1992).

Twentyman, Peter R., "Cyclosporins as drug resistance modifiers", Biochemical Pharmacology, 43, p. 109-117, (1992).

Ueda, K., et al., "Recent progress in P-Glycoprotein research," Anti-Cancer Drug Design (1999) 14:115-121.

USP Dictionary of USAN and International Drug Names, U.S. Pharmacopeia, Rockville, MD, 2001, 2001 Ed., p. 749.

Van Asperen, J. et al., "The Pharmacological Role of P-Glycoprotein in the Intestinal Epithelium", The Italian Pharmacological Society, (1998).

Van Rensburg, C. et al., "Novel tetramethylpiperidine-substituted phenazines are potent inhibitors of P-glycoprotein activity in a multidrug resistant activity in a multidrug resistant cancer cell line" Anti-Cancer Drugs, 8, p. 708-713 (1997).

van Veen, H. et al., "The ABC family of multidrug transporters in microorganisms" Biochim Biophys Acta 31-36 (1998).

Vanhoefer, U. et al., "PAK-104P, a Pyridine analogue, Reverses Paclitaxel and Doxorubicin Resistance in cell Lines and Nude Mice Bearing Xenografts that overexpresses the multidrug resistance protein" Clinical Cancer Research, 2, p. 369-377 (1996).

Vicar, J. et al., "Amino acids and peptides. CIX. Synthesis and infrared spectroscopy of 2,5-piperazinediones derived from proline and pipecolic acid," Collect. Czech. Chem. Commun. (1972) 37:4060-4071.

Volm, M., "Multidrug Resistance and its Reversal," Anticancer Research (1998) 18:2905-2918.

Wacher, V. et al., "Role of P-Glycoprotein and Cytochrome P450 3A in Limiting Oral Absorption of Peptides and Peptidomimetics" Journal of Pharmaceutical Sciences 87, p. 1322-1330, (1998).

Wakusawa, S. et al., "Overcoming of Vinblastine Resistance by Isoquinolinesulfonamide compounds in Adriamycin-Resistant Leukemia Cells" Molecular Pharmacology, 41, 1034-1038 (1992).

Watanabe, T. et al., "Effect of SDZ PSC 833 ([3'-keto-Bmt]-[Val]-cyclosporin) on serum protein binding and distribution to blood cells of doxorubicin, vincristine and etoposide in vitro" Anti-Cancer Drugs, 8, p. 400-404 (1997).

Wiese, M. et al., Molecular modeling study of the multidrug resistance modifiers cis- and trans-fllupentixol. Pharmazie, 52, p. 679-685 (1997).

Yang, J. et al., "Inhibitory Effect of Alkylating Modulators on the Function of P-Glycoprotein" Oncology Research, 9, p. 477-484, (1997).

Zablocki, J.A. et al., "A Novel Series of Orally Active Antiplatelet Agents," Bio. Med. Chem. (1995) 3(5):539-551.

Zhang, L. et al., "Characterization of Prenylcysteines that interact with P-glycoprotein and inhibit drug transport in tumor cells", The Journal of Biological Chemistry, 270, p. 22859-22865 (1995).

Zheleznova, E. et al., A structure-based mechanism for drug binding by multidrug transporters, Trends Biochem Sci., p. 39-43, (2000).

Zhu, B. T. "A Novel Hypothesis for the Mechanism of Action of P-Glycoprotein as a Multidrug Transporter" Molecular Carcinogenesis, 25, p. 1-13 (1999).

Abou-Ouf, A.A. et al., "Synthesis and local anesthetic activity of certain piperazine and ephedrine derivatives," J. Med. Chem. (1971) 14(5):443-445.

Harfenist, M., "Unsymmetrically-substituted piperazines," J. Am. Chem. Soc. (1954) 76:4991-4993.

Braun, P. et al., "Effects of glycosylation on fragments of tumour associated human epithelial mucin MUC1," Bioorg. Med. Chem. (1998) 6:1531-1545.

Hall, I.H. et al., "Substituted 4-hydroxyproline di- and tri-peptides as cytotoxic agents," Amino Acids (1999) 16:79-89.

Kast, W.M. et al., "Eradication of adenovirus E1-induced tumors by E1A-specific cytotoxic T lymphocytes," Cell (1989) 59:603-614.

Mallams, A.K. et al., "Inhibitors of Farnesyl protein transferase. 4-Amido, 4-Carbamoyl, and 4-Carboxamido derivatives of 1-(8-chloro-6, 11-dihydro-5H-benzo[5,6]-cyclohepta[1,2-b]pyridin-11-yl)piperazine and 1-(3-bromo-8-chloro-6, 11 -dihydro-5H-benzo[5,6]cyclohepta[1,2-b]pyridin-11-yl)piperazine," J. Med. Chem. (1998) 41:877-893.

Shioiri, T. et al., "Stereoselective synthesis of dolastatin 10 and its cogeners," Tetrahedron (1993) 49(9):1913-1924.

* cited by examiner

SUBSTITUTED HETEROCYCLIC COMPOUNDS FOR TREATING MULTIDRUG RESISTANCE

CROSS REFERENCE TO PRIORITY APPLICATIONS

This is a continuation application of U.S. application Ser. No. 09/996,657, filed Nov. 29, 2001, which is a divisional of U.S. application Ser. No. 09/740,643, filed Dec. 19, 2000, which claims priority to U.S. Provisional Application No. 60/241,127, filed Oct. 17, 2000, which all are incorporated by reference herein.

FIELD OF THE INVENTION

This invention relates to compounds for treating multidrug resistance and methods for their preparation and use. More particularly, this invention relates to substituted heterocyclic compounds that regulate the cellular transport proteins P-glycoprotein and MRP1, which are the proteins believed to be largely responsible for causing multidrug resistance in cancer patients.

BACKGROUND OF THE INVENTION

"Drug resistance" means a circumstance when a disease (e.g., cancer) does not respond to a therapeutic agent. Drug resistance can be intrinsic, which means that the disease has never been responsive to the therapeutic agent, or acquired, which means that the disease ceases responding to the agent or agents to which the disease had previously been responsive. "Multidrug resistance" is a type of drug resistance wherein a disease is resistant to a variety of drugs that can be functionally unrelated, structurally unrelated, or both. Multidrug resistance is a problem associated with cancer and other conditions, such as bacterial, viral, protozoal, and fungal diseases.

One cause of multidrug resistance in cancer patients is that many cancer cells express high levels of the transmembrane transport proteins, such as Pleiotropic-glycoprotein (also known as Pgp, P-glycoprotein, gp-170, or MDR1) and MRP1 (see Borst, P., "Multidrug resistance: A solvable problem?" *Annals of Oncology*, 10, suppl. 4, pp. S162-S164 (1999)). In adenosine-triphosphate driven processes, these transport proteins export hydrophobic compounds (such as vinblastine, daunorubicin, doxorubicin, etoposide, vincristine, and TAXOL®, which are cytotoxic drugs useful for treating cancer) from the cell in an effort to protect the cell from harm. The transport proteins remove the compounds from the cell prior to their having a lethal effect on the cell (see Legrand, et. al, "Simultaneous Activity of MRP1 and Pgp Is Correlated With In Vitro Resistance to Daunorubicin and With In Vivo Resistance in Adult Acute Myeloid Leukemia", *Blood*, Vol. 94, No. 3, pp. 1046-1056 (1999); and Zhu, B. T.; "A Novel Hypothesis for the Mechanism of Action of P-glycoprotein as a Multidrug Transporter," *Molecular Carcinogenesis* 25, pp. 1-14 (1999)). Although it is not currently known which of these two classes of proteins is more important for multidrug resistance, and indeed it may be that the class (or classes) of protein which is important depends on the type of cancer and the particular drug or drugs used to treat the cancer, Pgp is known to be highly expressed in approximately 50% of human cancers which require drug therapy. Consequently, Pgp is believed to be a major cause of multidrug resistance. Other types of multidrug resistance, such as antibacterial, antiviral, and antifungal multidrug resistance may also be caused by the action of transport proteins that are similar to Pgp, and others (see "Annual Reports on Medicinal Chemistry—33; Section III Cancer and Infectious Diseases" ed. Plattner, J., Academic Press, Ch. 12, pp. 121-130 (1998)).

Furthermore, Pgp is also expressed at high levels in the gastrointestinal tract, liver, kidneys, and brain, and therefore Pgp represents a major pharmacological barrier to the bioavailability of many drugs (see Amudkar, et. al in "Biochemical, Cellular, and Pharmacological Aspects of the Multidrug Transporter," *Annu. Rev. Pharmacol. Toxicol.*, 39, pp. 361-398 (1999)). For example, the oral bioavailability of many nutrients and drugs is negatively affected by the action of Pgp present in the gastrointestinal tract. "Oral bioavailability" means the ability of a drug or nutrient that is administered orally to be transported across the gastrointestinal tract and enter into the bloodstream. In addition, penetration of many drugs through the blood-brain barrier is adversely affected by Pgp.

SUMMARY OF THE INVENTION

This invention relates to novel compounds useful in treating or preventing multidrug resistance ("MDR"). More specifically, these compounds are useful in treating or preventing P-glycoprotein-mediated MDR and MRP1-mediated MDR. This invention further relates to compositions comprising these compounds. This invention further relates to methods for the preparation and use of the compounds and compositions. The compounds and compositions of this invention are well suited for treatment of multidrug resistant cells, for prevention of the development of multidrug resistance, and for use in multidrug resistant chemotherapies.

DETAILED DESCRIPTION OF THE INVENTION

Publications and patents are referred to throughout this disclosure. All U.S. Patents cited herein are hereby incorporated by reference.

All percentages, ratios, and proportions used herein are by weight unless otherwise specified.

Definitions and Usage of Terms

The following is a list of definitions, as used herein.

"Aromatic group" means a group having a monocyclic or polycyclic ring structure. Monocyclic aromatic groups contain 4 to 10 carbon atoms, preferably 4 to 7 carbon atoms, and more preferably 4 to 6 carbon atoms in the ring. Preferred polycyclic ring structures have two or three rings. Polycyclic structures having two rings typically have 8 to 12 carbon atoms, preferably 8 to 10 carbon atoms in the rings. Polycyclic aromatic groups include groups wherein at least one, but not all, of the rings are aromatic.

"Carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the rings.

"Carrier" means one or more substances that are suitable for administration to a subject (i.e., mammal) and that can be combined with the active compound according to this invention. Carrier includes solid and liquid diluents, hydrotropes, surface-active agents, and encapsulating substances.

"Chemosensitizing agent" means a noncytotoxic compound that sensitizes drug resistant cells to the action of cytotoxic drugs. As used in this application, the term "chemosensitizing agent", excludes the active compounds of this invention.

"Halogen atom" means F, Cl, Br, or I.

"Heteroaromatic group" means an aromatic group containing carbon and 1 to 4 heteroatoms in the ring. Monocyclic heteroaromatic groups contain 4 to 10 member atoms, preferably 4 to 7 member atoms, and more preferably 4 to 6 member atoms in the ring. Preferred polycyclic ring structures have two or three rings. Polycyclic structures having two rings typically have 8 to 12 member atoms, preferably 8 to 10 member atoms in the rings. Polycyclic heteroaromatic groups include groups wherein at least one, but not all, of the rings are heteroaromatic.

"Heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), preferably 4 to 7, and more preferably 5 to 6 in the ring. Bicyclic heterocyclic groups contain 8 to 18 member atoms, preferably 9 or 10 in the rings.

"Heterogeneous group" means a saturated or unsaturated chain of non-hydrogen member atoms comprising carbon atoms and at least one heteroatom. Heterogeneous groups typically have 1 to 25 member atoms. Preferably, the chain contains 1 to 12 member atoms, more preferably 1 to 10, and most preferably 1 to 6. The chain may be linear or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond.

"Hydrocarbon group" means a chain of 1 to 25 carbon atoms, preferably 1 to 12 carbon atoms, more preferably 1 to 10 carbon atoms, and most preferably 1 to 8 carbon atoms. Hydrocarbon groups may have a linear or branched chain structure. Preferred hydrocarbon groups have one or two branches, preferably 1 branch. Preferred hydrocarbon groups are saturated. Unsaturated hydrocarbon groups have one or more double bonds, one or more triple bonds, or combinations thereof. Preferred unsaturated hydrocarbon groups have one or two double bonds or one triple bond; more preferred unsaturated hydrocarbon groups have one double bond.

"$IC_{50}$" means concentration of drug required to produce a 50% inhibition of growth of cancer cells or 50% inhibition of activity.

"MDR" means multidrug resistance.

"Parenteral" as used herein includes subcutaneous, intravenous, intramuscular, intraarticular, intrasynovial, intrasternal, intrathecal, intrahepatic, intralesional and intracranial injection or infusion techniques.

"Pgp" means P-glycoprotein.

"Pharmaceutically acceptable" means suitable for use in a human or other mammal.

"Protecting group" is a group that replaces the active hydrogen of a —OH, —COOH, or —NH$_2$ moiety thus preventing undesired side reaction at the moiety. Use of protecting groups in organic synthesis is well known in the art. Examples of protecting groups are found in *Protecting Groups in Organic Synthesis* by Greene, T. W. and Wuts, P. G. M., 2nd ed., Wiley & Sons, Inc., 1991. Preferred protecting groups for hydroxyl moieties include silyl ethers, alkoxymethyl ethers, tetrahydropyranyl, tetrahydrofuranyl, esters, and substituted or unsubstituted benzyl ethers. Other preferred protecting groups include carbamates.

"Subject" means a living vertebrate animal such as a mammal (preferably human).

"Substituted aromatic group" means an aromatic group wherein 1 or more of the hydrogen atoms bonded to carbon atoms in the ring have been replaced with other substituents. Preferred substituents include hydrocarbon groups such as methyl groups and heterogeneous groups including alkoxy groups such as methoxy groups. The substituents may be substituted at the ortho, meta, or para position on the ring, or any combination thereof.

"Substituted carbocyclic group" means a carbocyclic group wherein 1 or more hydrogen atoms bonded to carbon atoms in the ring have been replaced with other substituents. Preferred substituents include hydrocarbon groups such as alkyl groups (e.g, methyl groups) and heterogeneous groups such as alkoxy groups (e.g., methoxy groups).

"Substituted heteroaromatic group" means a heteroaromatic group wherein 1 or more hydrogen atoms bonded to carbon atoms in the ring have been replaced with other substituents. Preferred substituents include monovalent hydrocarbon groups including alkyl groups such as methyl groups and monovalent heterogeneous groups including alkoxy groups such as methoxy groups.

"Substituted heterocyclic group" means a heterocyclic group wherein 1 or more hydrogen atoms bonded to carbon atoms in the ring have been replaced with other substituents. Preferred substituents include monovalent hydrocarbon groups including alkyl groups such as methyl groups and monovalent heterogeneous groups including alkoxy groups such as methoxy groups. Substituted heterocyclic groups are not aromatic.

"Substituted heterogeneous group" means a heterogeneous group, wherein 1 or more of the hydrogen atoms bonded to carbon atoms in the chain have been replaced with other substituents. Preferred substituents include monovalent hydrocarbon groups including alkyl groups such as methyl groups and monovalent heterogeneous groups including alkoxy groups such as methoxy groups.

"Substituted hydrocarbon group" means a hydrocarbon group wherein 1 or more of the hydrogen atoms bonded to carbon atoms in the chain have been replaced with other substituents. Preferred substituents include monovalent aromatic groups, monovalent substituted aromatic groups, monovalent hydrocarbon groups including alkyl groups such as methyl groups, monovalent substituted hydrocarbon groups such as benzyl, and monovalent heterogeneous groups including alkoxy groups such as methoxy groups.

"Substrate potential" means the likelihood that a compound for use in treating multidrug resistance will be transported out of a cell by cellular transport proteins before effectively preventing or reversing multidrug resistance.

"Transport protein" means a protein that acts to remove cytotoxic substances from cells through the cell membrane. Transport protein includes P-glycoprotein, MRP1, and others.

"Treating multidrug resistance" means preventing multidrug resistance from developing in nonresistant cells, increasing or restoring sensitivity of multidrug resistant cells to therapeutic or prophylactic agents, or both.

"Treating" means 1) preventing a disease (i.e., causing the clinical symptoms of the disease not to develop), 2) inhibiting the disease (i.e., arresting the development of clinical symptoms of the disease), 3) relieving the disease (i.e., causing regression of the clinical symptoms), and combinations thereof.

"Wax" means a lower-melting organic mixture or compound of high molecular weight, solid at room temperature and generally similar in formulation to fats and oils except that they contain no glycerides.

Active Compounds Used in this Invention

The active compounds of this invention are heterocyclic compounds. The active compounds have the general structure:

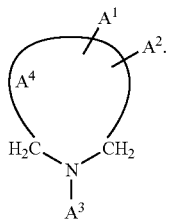

Groups $A^1$ and $A^2$ are each independently selected from the group consisting of a hydrogen atom and a group of the formula

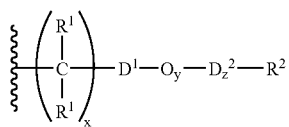

with the proviso that $A^1$ and $A^2$ are not both hydrogen atoms and ⁓ denotes a point of attachment.

Each $R^1$ is independently selected from the group consisting of a hydrogen atom, a hydroxyl group, a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. $R^1$ is preferably a hydrogen atom or a hydroxyl group. In group $A^1$, $R^1$ is preferably a hydrogen atom.

The subscript x is 0 to about 10, preferably 0 to about 1.

$R^2$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. $R^2$ is preferably selected from the group consisting of a hydrocarbon group, a substituted hydrocarbon group, a heterogeneous group, a substituted heterogeneous group, an aromatic group, a substituted aromatic group, a heteroaromatic group, and a substituted heteroaromatic group. More preferably, $R^2$ is a substituted hydrocarbon group or a substituted heterogeneous group, wherein said group is substituted with a group selected from the group consisting of an aromatic group, a substituted aromatic group, a heteroaromatic group, and a substituted heteroaromatic group.

In a preferred embodiment of the invention, $R^2$ is selected from the group consisting of:

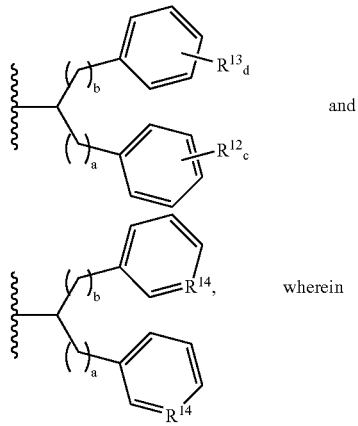

wherein a is at least about 2, b is at least about 2, c is about 1 to about 3, and d is about 1 to about 3. Preferably, a and b are each about 3 to about 10. More preferably, a and b are each about 3.

$R^{12}$ and $R^{13}$ are each independently selected from the group consisting of hydrocarbon groups and substituted hydrocarbon groups. Preferably, $R^{12}$ and $R^{13}$ are substituted hydrocarbon groups such as alkoxy groups. Preferred alkoxy groups include methoxy, ethoxy, propoxy, and butoxy.

Each $R^{14}$ is independently selected from the group consisting of CH and a heteroatom. Preferably, the heteroatom is nitrogen. More preferably, each $R^{14}$ is CH.

Groups $D^1$ and $D^2$ are each independently selected from the group consisting of —C(O)— and —NR$^3$—,
  wherein $R^3$ is selected from the group consisting of a hydrogen atom and $R^2$, and with the proviso that optionally, $R^2$ and $R^3$ may be bonded together to form a ring structure selected from the group consisting of heterocyclic groups and substituted heterocyclic groups when $D^2$ is —NR$^3$—;
  y is 0 or 1 and z is 0 or 1,
  with the provisos that when y is 0, z is 1 and when y is 1, z is 0,
  when y is 0 and $D^1$ is —NR$^3$—, then $D^2$ is —C(O)—, and when y is 0 and $D^2$ is —NR$^3$—, then $D^1$ is —C(O)—.
  Preferably, y is 0 and z is 1.

In one embodiment of the invention, $R^2$ and $R^3$ are bonded together and the ring structure has 5 to 6 members. Preferably, the ring structure formed by $R^2$ and $R^3$ is a substituted heterocyclic group, wherein the substituted heterocyclic group is substituted with a group selected from the group consisting of an aromatic group; a substituted aromatic group; a heteroaromatic group; a substituted heteroaromatic group; a substituted hydrocarbon group, wherein the substituted hydrocarbon group is substituted with a group selected from the group consisting of an aromatic group, a substituted aromatic group, a heteroaromatic group, and a substituted heteroaromatic group; and a substituted heterogeneous group, wherein the substituted heterogeneous group is substituted with a group selected from the group consisting of an aromatic group, a substituted aromatic group, a heteroaromatic group, and a substituted heteroaromatic group.

In a preferred embodiment of the invention, $D^1$ is —C(O)— and $D^2$ is —NR$^3$—. In this embodiment, preferably $R^3$ is selected from the group consisting of a hydrogen atom and a hydrocarbon group.

In an alternative embodiment of the invention, $D^1$ is —C(O)—, y is 1, and z is 0.

In an alternative embodiment of the invention, $D^1$ is —NR$^3$— and $D^2$ is —C(O)—. In this embodiment, preferably $R^3$ is selected from the group consisting of a hydrogen atom and a hydrocarbon group.

$A^3$ has the formula

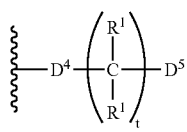

wherein t is 0 to about 6, preferably 0 to about 2.

Group $D^4$ is selected from the group consisting of —C(O)— and —CH(R$^1$)—. $D^4$ is preferably —CH(R$^1$)—.

Group $D^5$ is selected from the group consisting of —NR$^6$(R$^7$), —O$_r$R$^6$, and —C(O)R$^6$, wherein r is 0 or 1, preferably 1;

$R^6$ is selected from the group consisting of a hydrocarbon group, a substituted hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group; and $R^7$ is selected from the group consisting of a hydrogen atom and R$^6$. $R^7$ is preferably a hydrogen atom.

$D^5$ is preferably —O$_r$R$^6$, and R$^6$ is preferably selected from the group consisting of an aromatic group, a substituted aromatic group, a heteroaromatic group, and a substituted heteroaromatic group. $R^6$ is more preferably selected from the group consisting of a heteroaromatic group and a substituted heteroaromatic group. $R^6$ is most preferably a heteroaromatic group. Preferred heteroaromatic groups for $R^6$ have the formula:

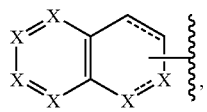

wherein each X is independently selected from the group consisting of CH and a heteroatom, with the proviso that at least one X is a heteroatom. The heteroatom is preferably nitrogen. Preferably, one X is a heteroatom. Examples of heteroaromatic groups for X include quinolyl and isoquinolyl groups. Preferred quinolyl groups for X include 4-quinolyl, 5-quinolyl, 6-quinolyl, 7-quinolyl, and 8-quinolyl. More preferably, X is 5-quinolyl.

In a preferred embodiment of the invention, $D^4$ is —C(O)—, t is 0, and $D^5$ is —C(O)R$^6$.

In an alternative preferred embodiment of the invention, $D^4$ is —C(O)— and $D^5$ is —O$_r$R$^6$.

In an alternative preferred embodiment of the invention, $D^4$ is —CH(R$^1$)— and $D^5$ is —O$_r$R$^6$.

In an alternative preferred embodiment of the invention, $D^4$ is —CH(R$^1$)— and $D^5$ is —NR$^6$(R).

In an alternative preferred embodiment of the invention, $D^4$ is —C(O)— and $D^5$ is —NR$^6$(R$^7$).

Group $A^4$ is a heterocyclic group having 4 to 9 member atoms. Preferably, $A^4$ has 4 to 6 member atoms, most preferably 5 or 6 member atoms.

Alternatively, the compound may be an optical isomer, a diastereomer, an enantiomer, a pharmaceutically-acceptable salt, a biohydrolyzable amide, a biohydrolyzable ester, and a biohydrolyzable imide of the structure, or combinations thereof.

Examples of compounds having the structure above are shown in Table 1.

TABLE 1

Example Compounds

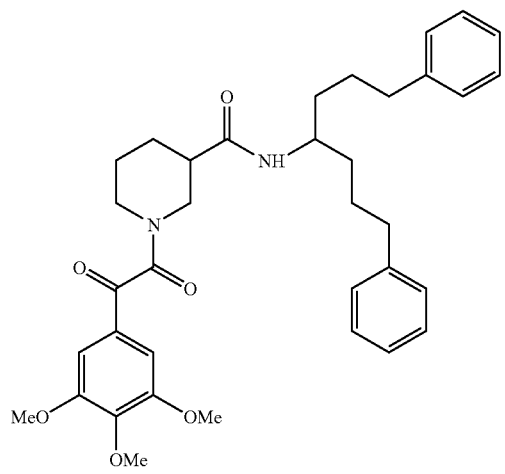

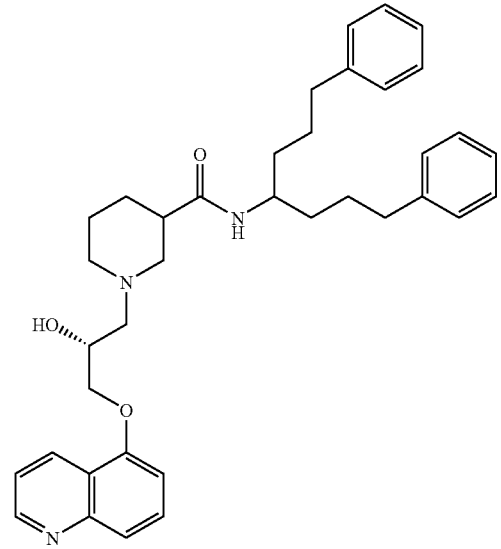

TABLE 1-continued
Example Compounds
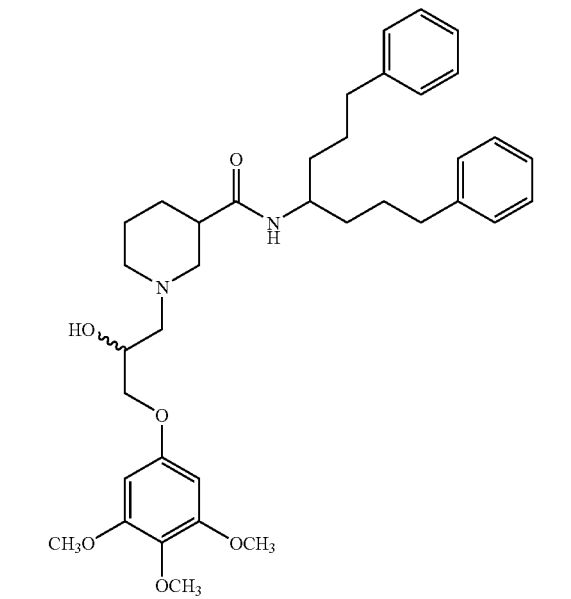
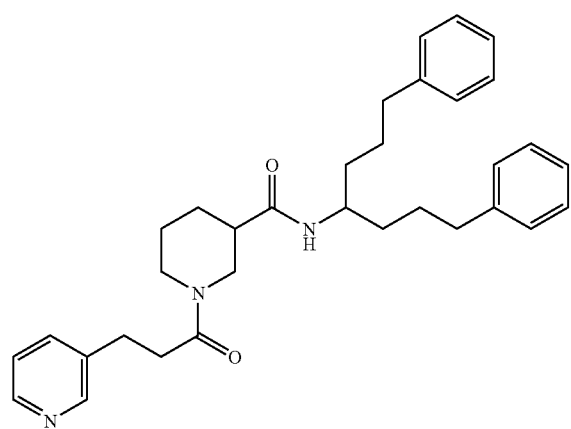
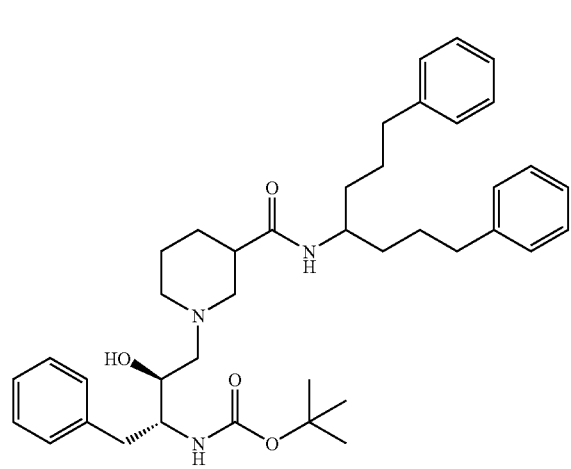
TABLE 1-continued
Example Compounds
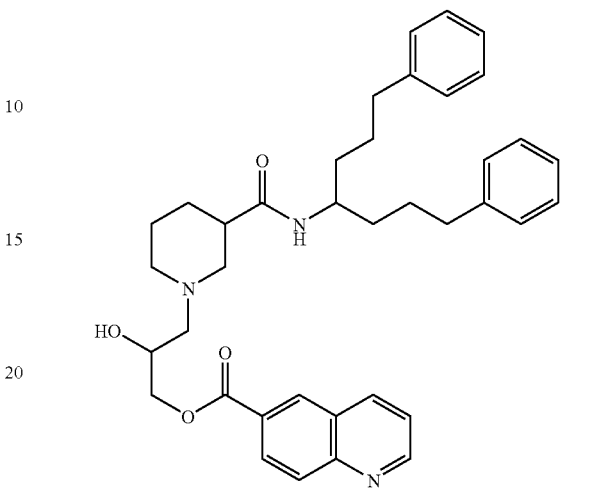
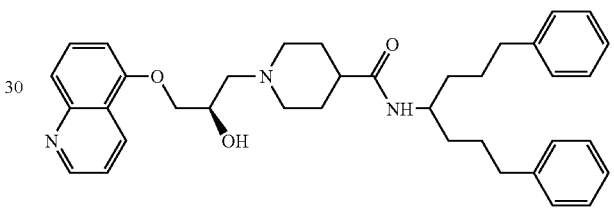
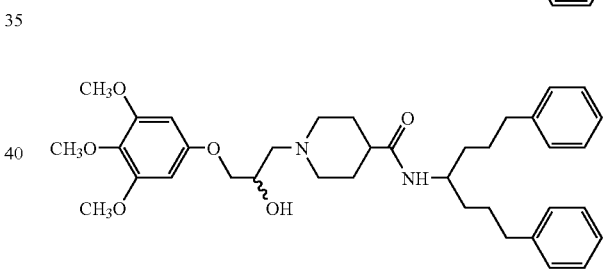
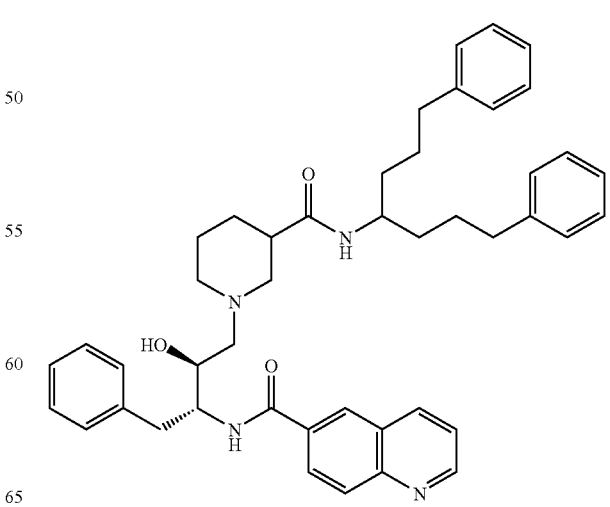

TABLE 1-continued
Example Compounds
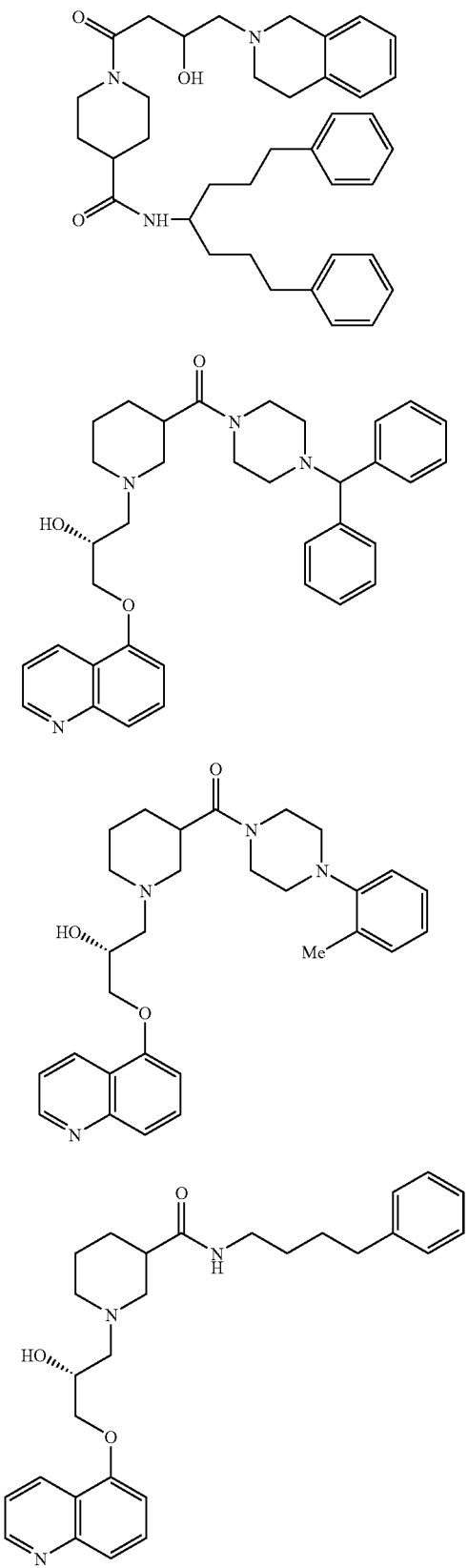
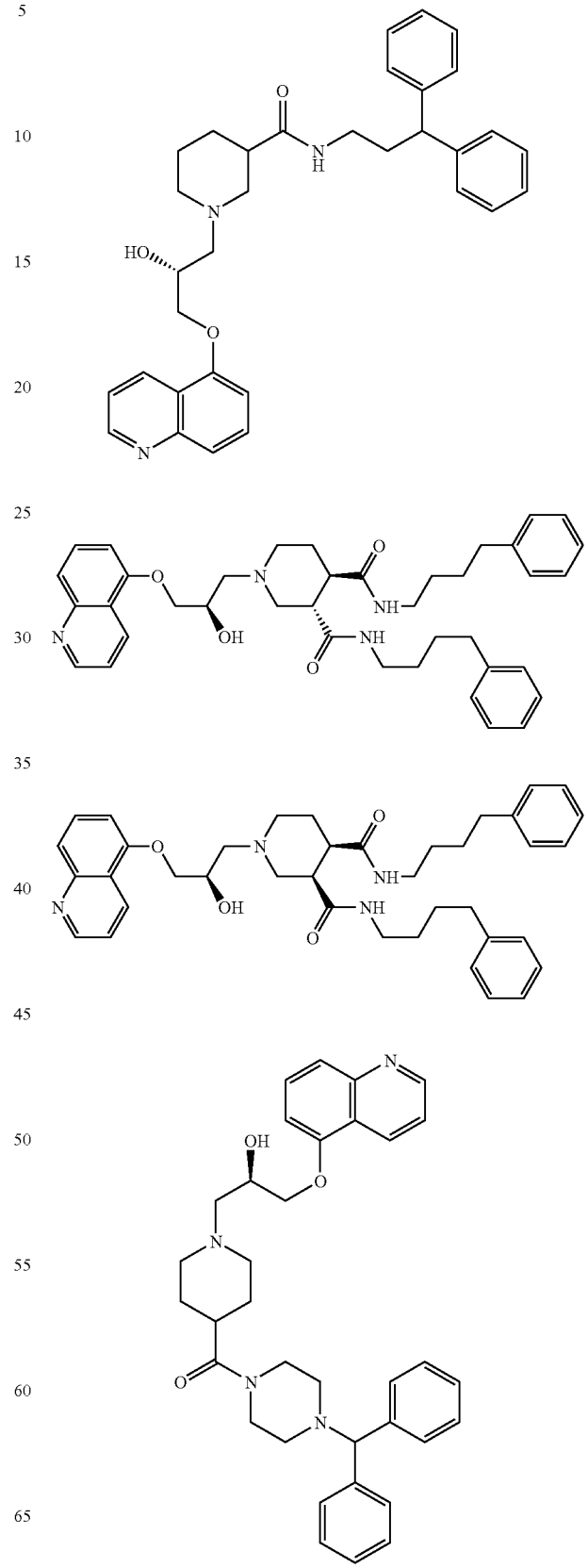

TABLE 1-continued
Example Compounds
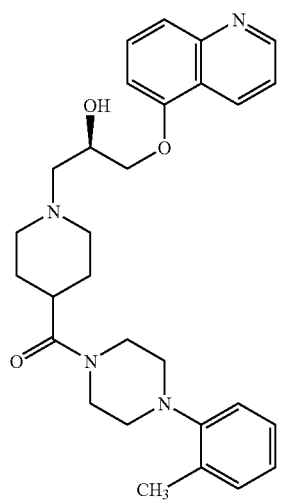
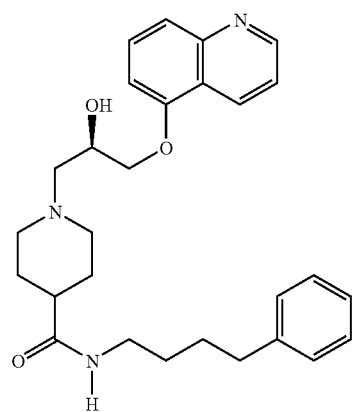
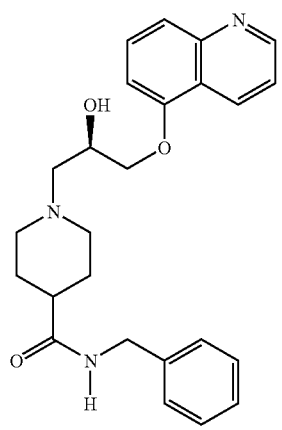
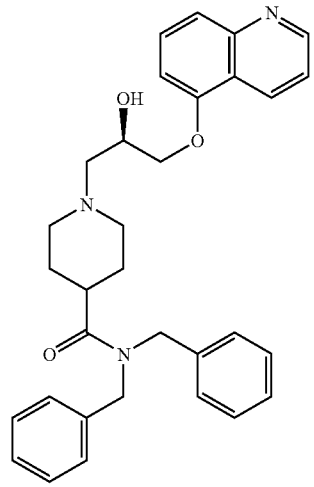
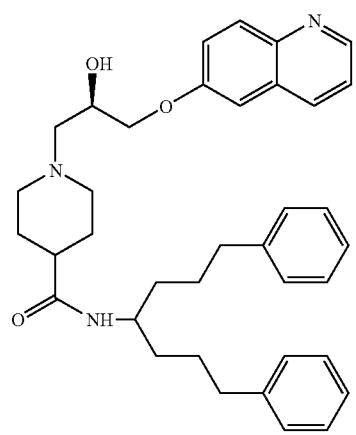
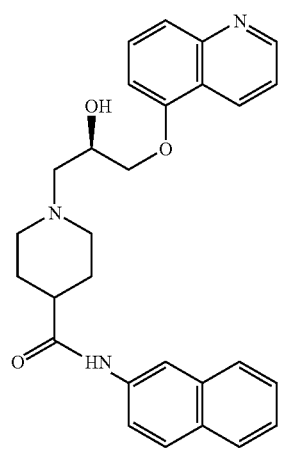

TABLE 1-continued
Example Compounds
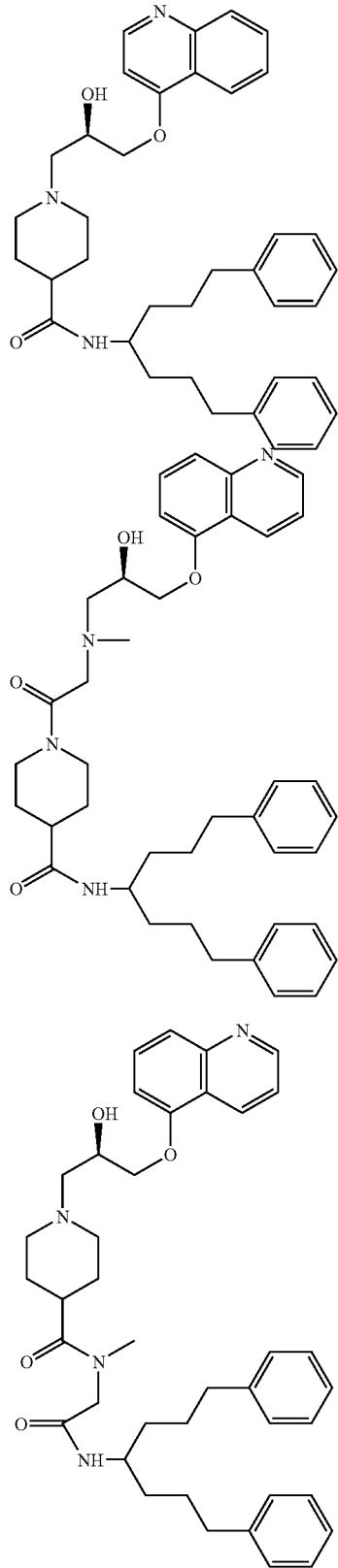
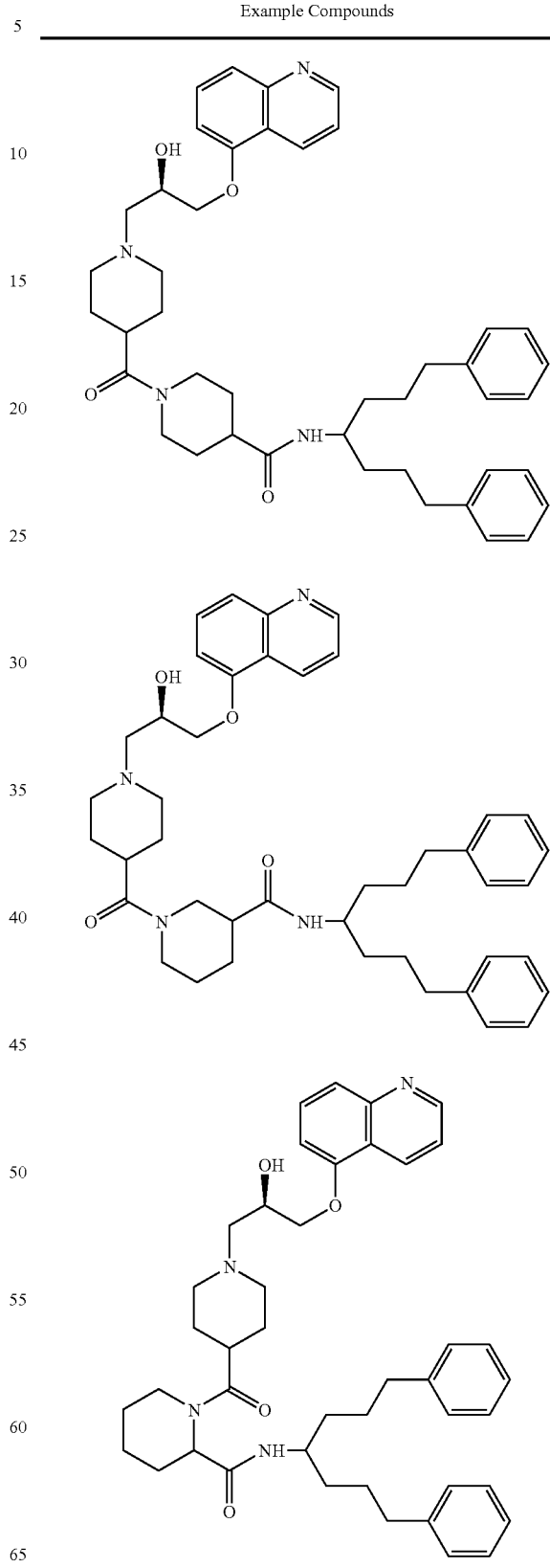

TABLE 1-continued
Example Compounds
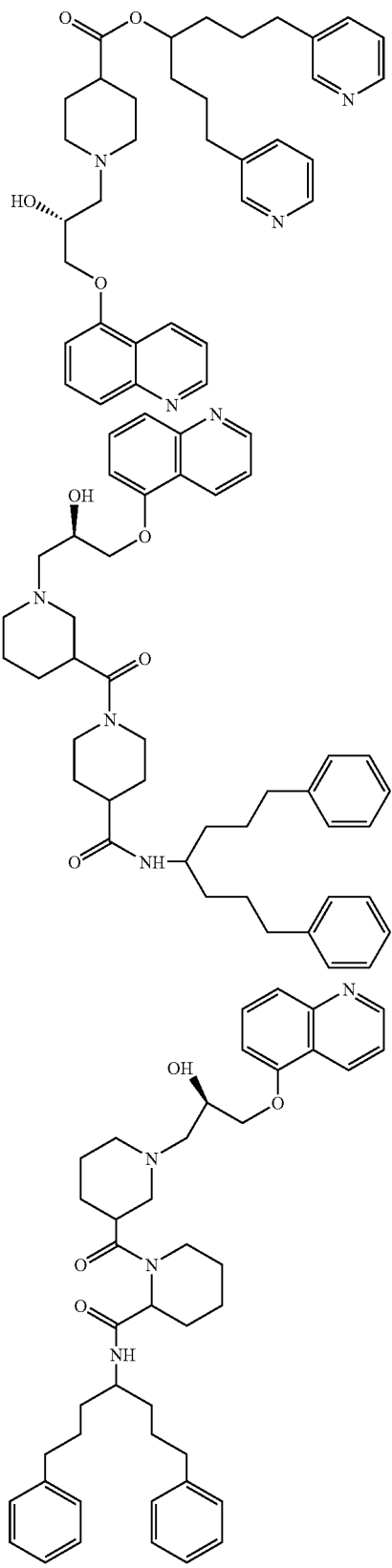
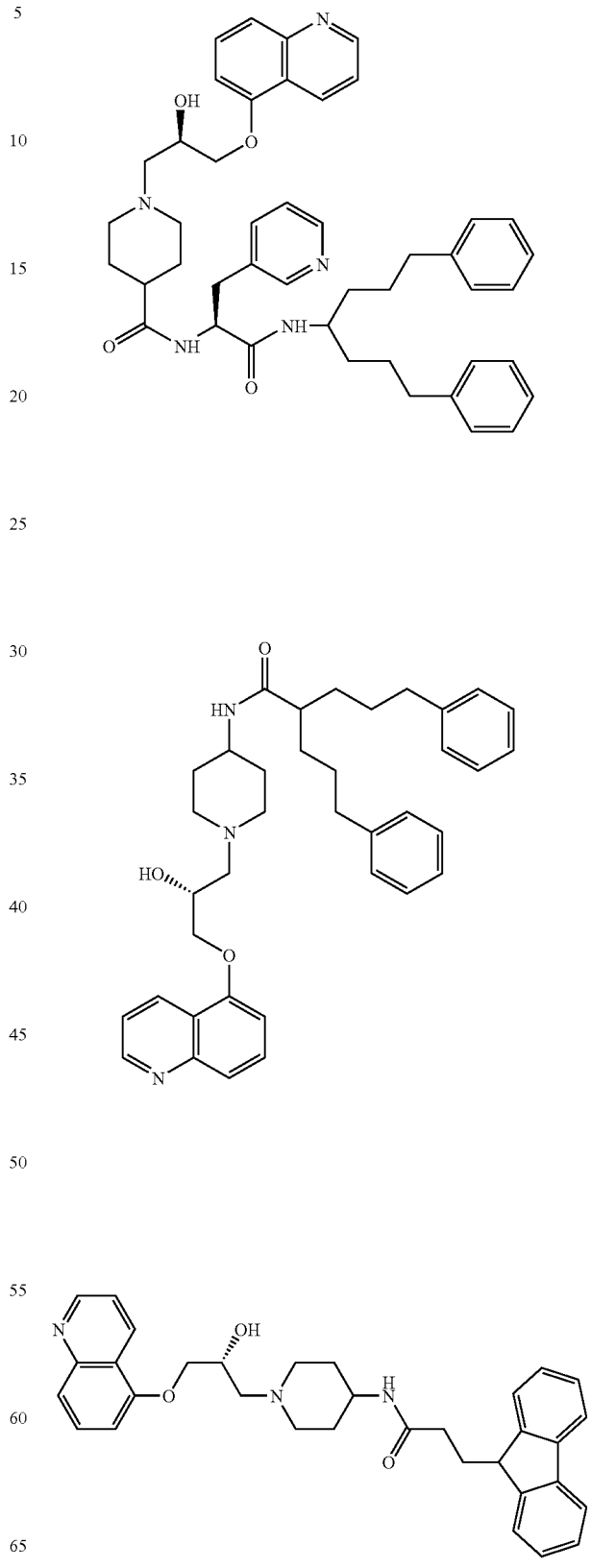

TABLE 1-continued
Example Compounds
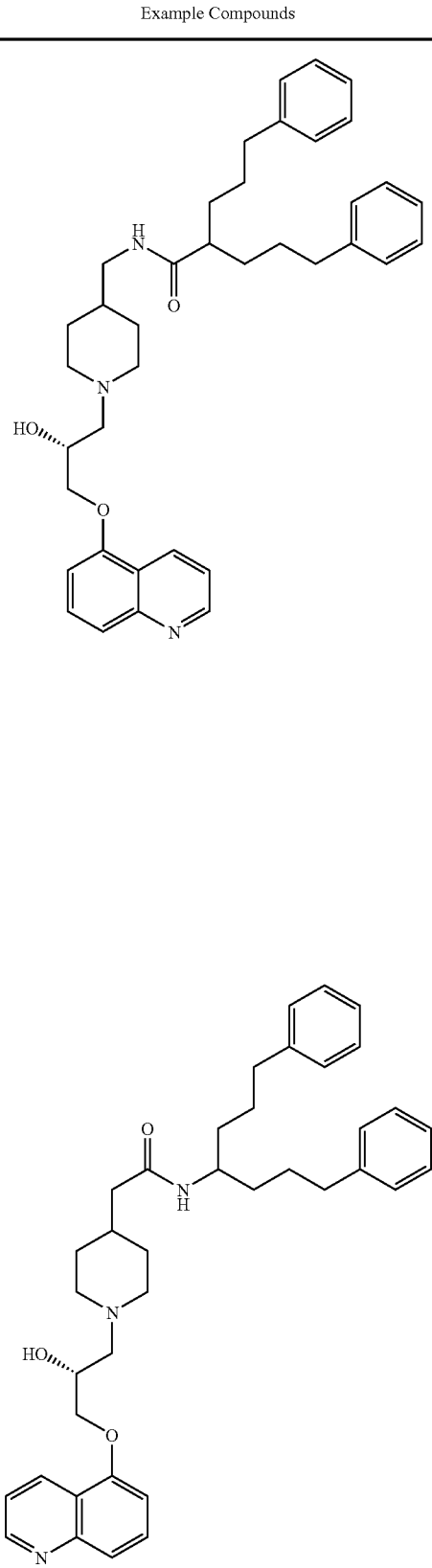
TABLE 1-continued
Example Compounds
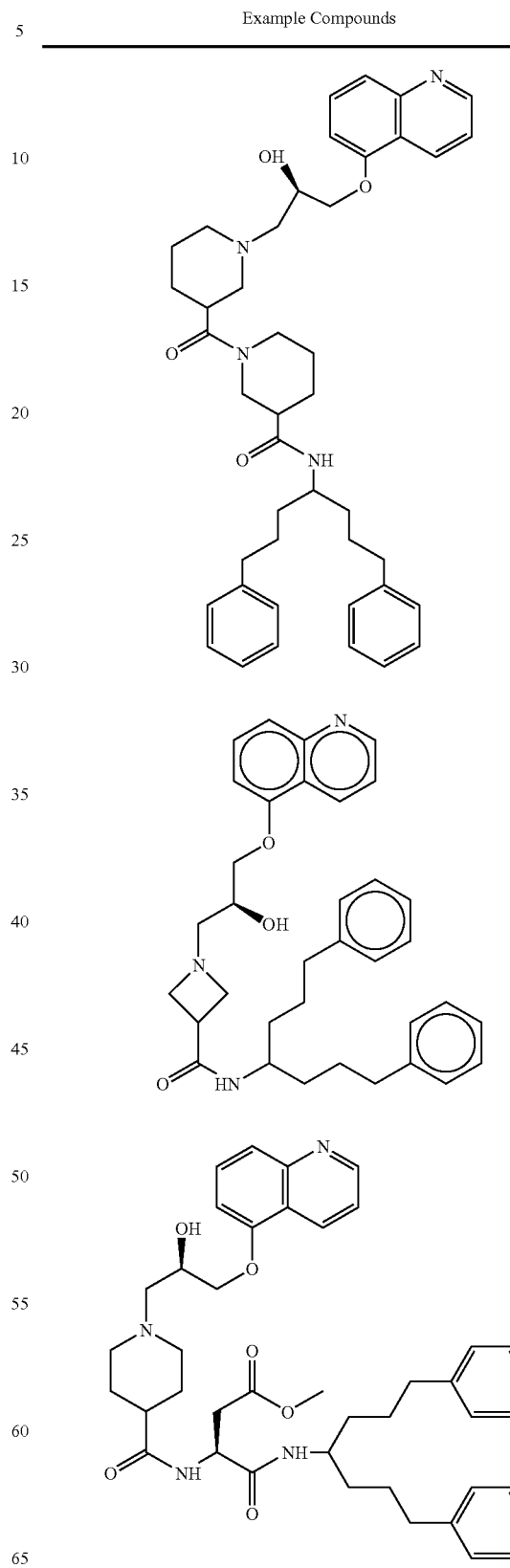

TABLE 1-continued

Example Compounds

[Chemical structure]

[Chemical structure]

[Chemical structure]

In Table 1 "Me" represents a methyl group.

The active compound of this invention inhibits at least one transport protein. The active compound preferably inhibits Pgp or MRP1. More preferably, the active compound inhibits both Pgp and MRP1. In a preferred embodiment of this invention, the active compound inhibits Pgp and has low substrate potential for Pgp. In an alternative preferred embodiment, the active compound inhibits MRP1 and has low substrate potential for MRP1. In the most preferred embodiment of this invention, the active compound inhibits both Pgp and MRP1 and the active compound has low substrate potential for both Pgp and MRP1.

The degree to which a compound inhibits a transport protein can be measured by quantitating the effectiveness of the compound toward restoring drug sensitivity to multidrug resistant cells. Methods for quantitating the effectiveness of the active compounds toward restoring drug sensitivity are readily available to one skilled in the art without undue experimentation (see U.S. Pat. Nos. 5,935,954 and 5,272,159, which are hereby incorporated by reference for the purpose of disclosing these methods). Any assay known to measure the restoration of the anti-proliferative activity of a drug may be employed to test the compounds of this invention. These assays use cell lines resistant to particular drugs, and characterized by the presence of one or both of Pgp and MRP1. These cell lines include L1210, HL60, P388, CHO, and MCF7. Alternatively, resistant cell lines can be developed by methods readily available to one of ordinary skill in the art without undue experimentation (see Chaudhary, et al., "Induction of Multidrug Resistance in Human Cells by Transient Exposure to Different Chemotherapeutic Agents," *Journal of the National Cancer Institute*, Vol. 85, No. 8, pp. 632-639 (1993)). The cell line is then exposed to compounds of this invention in the presence or absence of the drug to which it is resistant, such as TAXOL®. The viability of the cells treated with both the active compound and the drug can then be compared to the viability of the cells treated only with the drug.

The active compound preferably also has low substrate potential for Pgp or MRP1. More preferably, the active compound has low substrate potential for both Pgp and MRP1. Substrate potential for a transport protein can be determined by using an assay for measuring ATPase activity of the Pgp or MRP1 pumps (see, for example, Reference Example 4, below).

Methods for quantitating accumulation of the active compounds are readily available to one skilled in the art without undue experimentation (see U.S. Pat. No. 5,272,159 which is hereby incorporated by reference for the purpose of disclosing assays for quantitating accumulation). These assays use cell lines resistant to particular chemotherapeutic agents, and characterized by the presence of one or both of Pgp and MRP1. The cell line is exposed to a labeled form of the active compound (e.g., radioactivity or fluorescence labeling) and the accumulation of the active compound is monitored over time. The amount of active compound accumulated in the cell can be compared with a compound which is readily transported by these proteins, e.g. labeled TAXOL®.

Compositions of this Invention

This invention further relates to a composition. The composition can be used for treating various conditions or disease states. The composition is preferably a pharmaceutical composition administered for treatment or prevention of multi-drug resistance. Standard pharmaceutical formulation techniques are used, such as those disclosed in *Remington's*

*Pharmaceutical Sciences*, Mack Publishing Company, Easton, Pa. (1990) and U.S. Pat. No. 5,091,187, which is hereby incorporated by reference.

The composition comprises component (A) the active compound described above and component (B) a carrier. The composition may further comprise component (C) an optional ingredient, such as a therapeutic agent.

Component (B) is a carrier. A carrier is one or more compatible substances that are suitable for administration to a mammal. "Compatible" means that the components of the composition are capable of being commingled with component (A), and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both, depending on the intended use as described herein.

The choice of carrier for component (B) depends on the route by which component (A) will be administered and the form of the composition. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis).

Systemic Compositions

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) surfactants, combinations thereof, and others.

Ingredient a) is a diluent. Suitable diluents include sugars such as glucose, lactose, dextrose, and sucrose; polyols such as propylene glycol; calcium carbonate; sodium carbonate; glycerin; mannitol; sorbitol; and maltodextrin. The amount of ingredient a) in the composition is typically about 1 to about 99%.

Ingredient b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of ingredient b) in the composition is typically about 1 to about 99%.

Ingredient c) is a binder. Suitable binders include polyvinylpyrrolidone; magnesium aluminum silicate; starches such as corn starch and potato starch; gelatin; tragacanth; and cellulose and its derivatives, such as sodium carboxymethylcellulose, ethylcellulose, methylcellulose, microcrystalline cellulose, and hydroxypropylmethylcellulose; carbomer; providone; acacia; guar gum; and xanthan gum. The amount of ingredient c) in the composition is typically about 1 to about 99%.

Ingredient d) is a disintegrant. Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of ingredient d) in the composition is typically about 1 to about 99%.

Ingredient e) is a colorant such as an FD&C dye. The amount of ingredient e) in the composition is typically about 1 to about 99%.

Ingredient f) is a flavor such as menthol, peppermint, and fruit flavors. The amount of ingredient f) in the composition is typically about 1 to about 99%.

Ingredient g) is a sweetener such as saccharin and aspartame. The amount of ingredient g) in the composition is typically about 1 to about 99%.

Ingredient h) is an antioxidant such as butylated hydroxyanisole, butylated hydroxytoluene, and vitamin E. The amount of ingredient h) in the composition is typically about 1 to about 99%.

Ingredient j) is a preservative such as phenol, alkyl esters of parahydroxybenzoic acid, benzoic acid and the salts thereof, boric acid and the salts thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, ethyl paraben, and propyl paraben. Particularly preferred are the salts of benzoic acid, cetylpyridinium chloride, methyl paraben and propyl paraben, and sodium benzoate. The amount of ingredient j) in the composition is typically about 1 to about 99%.

Ingredient k) is a glidant such as silicon dioxide. The amount of ingredient k) in the composition is typically about 1 to about 99%.

Ingredient m) is a solvent, such as water, isotonic saline, ethyl oleate, alcohols such as ethanol, glycerin, cremaphor, glycols (e.g., polypropylene glycol and polyethylene glycol), and buffer solutions (e.g., phosphate, potassium acetate, boric carbonic, phosphoric, succinic, malic, tartaric, citric, acetic, benzoic, lactic, glyceric, gluconic, glutaric, and glutamic). The amount of ingredient m) in the composition is typically about 1 to about 99%.

Ingredient n) is a suspending agent. Suitable suspending agents include AVICEL® RC-591 from FMC Corporation of Philadelphia, Pa. and sodium alginate. The amount of ingredient n) in the composition is typically about 1 to about 99%.

Ingredient o) is a surfactant such as lecithin, polysorbate 80, sodium lauryl sulfate, polyoxyethylene sorbitan fatty acid esters, polyoxyethylene monoalkyl ethers, sucrose monoesters, lanolin esters, and lanolin ethers. Suitable surfactants are known in the art and commercially available, e.g., the TWEENS® from Atlas Powder Company of Wilmington, Del. Suitable surfactants are disclosed in the *C.T.F.A. Cosmetic Ingredient Handbook*, pp. 587-592 (1992); *Remington's Pharmaceutical Sciences*, 15th Ed., pp. 335-337 (1975); and *McCutcheon's Volume 1 Emulsifiers & Detergents*, North American Edition, pp. 236-239 (1994). The amount of ingredient o) in the composition is typically about 1 to about 99%.

The carrier ingredients discussed above are exemplary and not limiting. One skilled in the art would recognize that different carrier ingredients may be added to or substituted for the carrier ingredients above. One skilled in the art would be able to select appropriate carrier ingredients for systemic compositions without undue experimentation.

Compositions for parenteral administration typically comprise (A) about 0.1 to about 10% of an active compound and (B) about 90 to about 99.9% of a carrier comprising a) a diluent and m) a solvent. Preferably, component a) is propylene glycol and m) is selected from the group consisting of ethanol, ethyl oleate, water, isotonic saline, and combinations thereof.

Compositions for oral administration can have various dosage forms. For example, solid forms include tablets, capsules, granules, and bulk powders. These oral dosage forms comprise a safe and effective amount, usually at least about 1%, and preferably from about 5% to about 50%, of component (A). The oral dosage compositions further comprise (B) about 50 to about 99% of a carrier, preferably about 50 to about 95%.

Tablets can be compressed, tablet triturates, enteric-coated, sugar-coated, film-coated, or multiple-compressed. Tablets typically comprise (A) the active compound, and (B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose, and sucrose. Preferred binders include starch, and gelatin. Preferred disintegrants include alginic acid, and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin or f) flavors such as menthol, peppermint, and fruit flavors, or both.

Capsules (including time release and sustained release compositions) typically comprise (A) the active compound and (B) the carrier comprising one or more a) diluents disclosed above in a capsule comprising gelatin. Granules typically comprise (A) the active compound, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art can optimize appropriate ingredients without undue experimentation.

The solid compositions may also be coated by conventional methods, typically with pH or time-dependent coatings, such that component (A) is released in the gastrointestinal tract at various times to extend the desired action. The coatings typically comprise one or more components selected from the group consisting of cellulose acetate phthalate, polyvinylacetate phthalate, hydroxypropyl methyl cellulose phthalate, ethyl cellulose, acrylic resins such as EUDRAGIT® coatings (available from Rohm & Haas G.M.B.H. of Darmstadt, Germany), waxes, shellac, polyvinylpyrrolidone, and other commercially available film-coating preparations such as Dri-Klear, manufactured by Crompton & Knowles Corp., Mahwah, N.J. or OPADRY® manufactured by Colorcon, Inc., of West Point, Pa.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise (A) the active compound and (B) a carrier comprising ingredients selected from the group consisting of a) diluents, e) colorants, and f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the active compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethylcellulose, and hydroxypropylmethylcellulose. Such compositions may further comprise b) lubricants, e) colorants, f) flavors, g) sweeteners, h) antioxidants, and k) glidants.

The composition may further comprise component (C) one or more optional ingredients. Component (C) can be a therapeutic agent used to treat the underlying disease from which the subject suffers. For example, component (C) can be (i) a cancer therapeutic agent, such as a chemotherapeutic agent or a chemosensitizing agent, or a combination thereof; (ii) an antibacterial agent, (iii) an antiviral agent, (iv) an antifungal agent, and combinations thereof. Component (C) can be coadministered with component (A) to increase the susceptibility of the multidrug resistant cells within the subject to the therapeutic agent.

Suitable (i) cancer therapeutic agents are known in the art. Cancer therapeutic agents include chemotherapeutic agents, chemosensitizing agents, and combinations thereof. Suitable chemotherapeutic agents are disclosed in U.S. Pat. No. 5,416,091, which is hereby incorporated by reference for the purpose of disclosing chemotherapeutic agents. Suitable chemotherapeutic agents include actinomycin D, adriyamycin, amsacrine, colchicine, daunorubicin, docetaxel (which is commercially available as TAXOTERE® from Aventis Pharmaceuticals Products, Inc.), doxorubicin, etoposide, mitoxantrone, mytomycin C, paclitaxel (which is commercially available as TAXOL® from Bristol-Myers Squibb Company of New York, N.Y.), tenipaside, vinblastine, vincristine, and combinations thereof.

Suitable chemosensitizing agents include calcium channel blockers, calmodulin antagonists, cyclic peptides, cyclosporins and their analogs, phenothiazines, quinidine, reserpine, steroids, thioxantheres, transflupentixol, trifluoperazine, and combinations thereof. Suitable chemosensitizing agents are disclosed by Amudkar, et. al in "Biochemical, Cellular, and Pharmacological Aspects of the Multidrug Transporter," *Annu. Rev. Pharmacol. Toxicol.*, 39, pp. 361-398 (1999).

Suitable (ii) antibacterial agents, (iii) antiviral agents, and (iv) antifungal agents are known in the art (see "Annual Reports on Medicinal Chemistry—33; Section III Cancer and Infectious Diseases" ed. Plattner, J., Academic Press, Ch. 12, pp. 121-130 (1998)). Suitable antibacterial agents include quinolones, fluoroquinolones, ®-lactam antibiotics, aminoglycosides, macrolides, glycopeptides, tetracyclines, and combinations thereof.

Suitable (iii) antiviral agents include protease inhibitors, DNA synthase inhibitors, reverse transcription inhibitors, and combinations thereof.

Suitable (iv) antifungal agents include azoles, such as ketoconazole, fluconazole, itraconazole, and combinations thereof.

One skilled in the art will recognize that these therapeutic agents are exemplary and not limiting, and that some may be used in the treatment of various multidrug resistant conditions and diseases. One skilled in the art would be able to select therapeutic agents without undue experimentation.

The amount of component (C) used in combination with component (A), whether included in the same composition or separately coadministered, will be less than or equal to that used in a monotherapy. Preferably, the amount of component (C) is less than 80% of the dosage used in a monotherapy. Monotherapeutic dosages of such agents are known in the art.

Component (C) may be part of a single pharmaceutical composition or may be separately administered at a time before, during, or after administration of component (A), or combinations thereof.

In a preferred embodiment, the composition of this invention comprises component (A), component (B), and (C) a chemotherapeutic agent. In an alternative preferred embodiment, the composition comprises component (A), component (B), and (C) a chemosensitizing agent. In another preferred alternative embodiment, the composition comprises component (A), component (B), and (C) both a chemotherapeutic agent and a chemosensitizing agent.

The exact amounts of each component in the systemic compositions depend on various factors. These factors include the specific compound selected as component (A), and the mode by which the composition will be administered. The amount of component (A) in the systemic composition is typically about 1 to about 99%.

The systemic composition preferably further comprises 0 to 99% component (C), and a sufficient amount of component (B) such that the amounts of components (A), (B), and (C), combined equal 100%. The amount of (B) the carrier employed in conjunction with component (A) is sufficient to provide a practical quantity of composition for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Topical Compositions

Topical compositions comprise: component (A), described above, and component (B) a carrier. The carrier of the topical composition preferably aids penetration of component (A) into the skin. Topical compositions preferably further comprise (C) the optional ingredient described above.

Component (B) the carrier may comprise a single ingredient or a combination of two or more ingredients. In the topical compositions, component (B) is a topical carrier. Preferred topical carriers comprise one or more ingredients selected from the group consisting of water, alcohols, aloe vera gel, allantoin, glycerin, vitamin A and E oils, mineral oil, propylene glycol, polypropylene glycol-2 myristyl propionate, dimethyl isosorbide, combinations thereof, and the like. More preferred carriers include propylene glycol, dimethyl isosorbide, and water.

The topical carrier may comprise one or more ingredients selected from the group consisting of q) emollients, r) propellants, s) solvents, t) humectants, u) thickeners, v) powders, and w) fragrances in addition to, or instead of, the preferred topical carrier ingredients listed above. One skilled in the art would be able to optimize carrier ingredients for the topical compositions without undue experimentation.

Ingredient q) is an emollient. The amount of ingredient q) in the topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, polydimethylsiloxane, and combinations thereof. Preferred emollients include stearyl alcohol and polydimethylsiloxane.

Ingredient r) is a propellant. The amount of ingredient r) in the topical composition is typically about 5 to about 95%. Suitable propellants include propane, butane, isobutane, dimethyl ether, carbon dioxide, nitrous oxide, nitrogen, and combinations thereof.

Ingredient s) is a solvent. The amount of ingredient s) in the topical composition is typically about 5 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient t) is a humectant. The amount of ingredient t) in the topical composition is typically about 5 to about 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient u) is a thickener. The amount of ingredient u) in the topical composition is typically 0 to about 95%.

Ingredient v) is a powder. The amount of ingredient v) in the topical composition is typically 0 to about 95%. Suitable powders include chalk, talc, fullers earth, kaolin, starch, gums, colloidal silicon dioxide, sodium polyacrylate, tetraalkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically about 0.001 to about 0.5%, preferably about 0.001 to about 0.1%.

Ingredient x) is a wax. Waxes useful in this invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 40 and 100° C. The amount of ingredient x) in the topical composition is typically about 1 to about 99%.

In an alternative embodiment of the invention, the active compounds may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred composition for topical delivery of the present compounds uses liposomes as described in Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404-407 (1993); Wallach and Philippot, "New Type of Lipid Vesicle: Novasome®", *Liposome Technology*, Vol. 1, pp. 141-156 (1993); U.S. Pat. No. 4,911,928, and U.S. Pat. No. 5,834,014.

The exact amounts of each component in the topical composition depend on various factors. Including the specific compound selected for component (A) and the mode by which the composition will be administered. However, the amount of component (A) typically added to the topical composition is about 0.1 to about 99%, preferably about 1 to about 10%.

The topical composition preferably further comprises 0 to about 99% component (C), more preferably 0 to abut 10%, and a sufficient amount of component (B) such that the amounts of components (A), (B), and (C), combined equal 100%. The amount of (B) the carrier employed in conjunction with component (A) is sufficient to provide a practical quantity of composition for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like.

Component (A) may be included in kits comprising component (A), a systemic or topical composition described above, or both; and information, instructions, or both that use of the kit will provide treatment for multidrug resistance (particularly in humans). The information and instructions may be in the form of words, pictures, or both, and the like. In addition or in the alternative, the kit may comprise component (A), a composition, or both; and information, instructions, or both, regarding methods of administration of component (A) or the composition, preferably with the benefit of treating multidrug resistance in mammals.

In an alternative embodiment of the invention, components (A) and (C) may be included in kits comprising components (A) and (C), systemic or topical compositions described above, or both; and information, instructions, or both that use of the kit will provide treatment for multidrug resistance (particularly humans). The information and instructions may be in the form of words, pictures, or both, and the like. In addition or in the alternative, the kit may comprise components (A) and (C), compositions, or both; and information, instructions, or both, regarding methods of administration of components (A) and (C) or the compositions, preferably with the benefit of treating multidrug resistance in mammals.

Methods of Use of the Invention

This invention relates to a method of inhibiting a transport protein. The method comprises administering to a mammal in need of treatment, (A) an active compound described above.

This invention further relates to a method for treating multidrug resistance. The method comprises administering to a mammal (preferably a human) suffering from multidrug resistance, (A) an active compound described above. For example, a mammal diagnosed with multidrug resistant cancer can be treated by the methods of this invention. Preferably, a systemic or topical composition comprising (A) the active compound and (B) the carrier is administered to the mammal. More preferably, the composition is a systemic composition comprising (A) the active compound, (B) the carrier, and (C) an optional ingredient such as a therapeutic agent. Component (A) may be administered before, during, or after administration of component (C). A preferred administration schedule is a continuous infusion over the 24 hour period during which component (C) is also administered.

The dosage of component (A) administered depends on various factors, including the method of administration, the physical attributes of the subject (e.g., age, weight, and gender), and the condition from which the subject suffers. Effective dosage levels for treating or preventing MDR range from about 0.01 to about 100 mg/kg body weight per day, preferably about 0.5 to about 50 mg/kg body weight per day of (A) a compound of this invention. These dosage ranges are merely exemplary, and daily administration can be adjusted depending on various factors. The specific dosage of the active compound to be administered, as well as the duration of treatment, and whether the treatment is topical or systemic are interdependent. The dosage and treatment regimen will also depend upon such factors as the specific active compound used, the treatment indication, the efficacy of the active compound, the personal attributes of the subject (such as, for example, weight, age, sex, and medical condition of the subject), compliance with the treatment regimen, and the presence and severity of any side effects of the treatment.

In addition to the benefits in treating multidrug resistance in subjects suffering from cancer, the active compounds in the compositions and methods of this invention can also be used to treat other conditions. These other conditions include other types of multidrug resistance (i.e., in addition to cancer multidrug resistance) such as bacterial, viral, and fungal multidrug resistance. For example, many of the FDA approved HIV protease inhibitors used to treat AIDS patients suffering from the HIV virus are substrates for Pgp. Therefore, in an alternative embodiment of this invention, an active compound of this invention is coadministered with a therapeutic agent such as an HIV protease inhibitor.

The active compounds and compositions of this invention can also be administered with other therapeutic agents such as oral drugs. The active compounds and compositions can be used to enhance oral drug absorption and increase bioavailability of various drugs.

The active compounds and compositions can also be used to aid drug delivery through the blood-brain barrier for, e.g., enhancing the effectiveness of drugs to treat Alzheimer's disease, treating memory disorders, enhancing memory performance, or treating any other central nervous system disorder where drug delivery is compromised via this transport pump mechanism.

The active compounds and compositions can also be administered to treat subjects suffering from neurological disorders such as spinal injuries, diabetic neuropathy, and macular degeneration.

The active compounds and compositions can also be administered to treat subjects suffering from vision disorders and to improve vision.

The active compounds and compositions can also be administered to treat hair loss. "Treating hair loss" includes arresting hair loss, reversing hair loss, and promoting hair growth.

The active compounds and compositions can also be administered to treat inflammatory diseases. Inflammatory diseases include irritable bowel disease, arthritis, and asthma.

EXAMPLES

These examples are intended to illustrate the invention to those skilled in the art and should not be interpreted as limiting the scope of the invention set forth in the claims. The active compounds of this invention can be made using conventional organic syntheses, which are readily available to one skilled in the art without undue experimentation. Such syntheses can be found in standard texts such as J. March, *Advanced Organic Chemistry*, John Wiley & Sons, 1992. One of ordinary skill in the art will appreciate that certain reactions are best carried out when other functionalities are masked or protected in the compound, thus increasing the yield of the reaction or avoiding any undesirable side reactions. The skilled artisan may use protecting groups to accomplish the increased yields or to avoid the undesired reactions. These reactions can be found in the literature, see for example, Greene, T. W. and Wuts, P. G. M., *Protecting Groups in Organic Synthesis*, 2nd ed., John Wiley & Sons, 1991.

The starting materials for preparing the compounds of the invention are known, made by known methods, or commercially available. The starting materials for preparing the compounds of the invention may include the following.

The following reagents are available from Aldrich Chemical Company, Milwaukee, Wis.: 1-bromo-3-phenylpropane, 5-hydroxyquinoline, (R)-(–)-glycidyl tosylate, 3,4-pyridinedicarboxylic acid, 4-phenylbutylamine, 3-pyridinepropionic acid, tert-butyl[S-(R*, R*)]-(–)-(1-oxiranyl)-2-phenylethyl)carbamate, epichlorohydrin, 3,4,5-trimethoxybenzoyl chloride, N,N-diisopropylethylamine, 4-dimethylaminopyridine, 1-hydroxybenzotriazole, 4-trans-aminomethylcyclohexanecarboxylic acid, 3,4,5-trimethoxybenzylamine, and 2,2,4-trimethyl-2-oxazoline.

The following reagents are available from Lancaster Synthesis Inc., Windham, N.H.: 4-phenylbutyronitrile, 1-tert-butoxycarbonyl-piperidine-3-carboxylic acid, 1-benzyl-4-aminopiperidine, 3,4-dimethoxybenzenesulfonyl chloride, and 1-benzyl-4-homopiperazine.

The following reagents are available from Fluka Chemie AG, Milwaukee, Wis.: 1-tert-butoxycarbonyl-piperidine-4-carboxylic, and (benzotriazol-1-yloxy)tripyrrolidinophosphonium hexafluorophosphate ("PyBOP"), N-(tert-butoxycarbonyl)-iminodiacetic acid, and 1-(diphenylmethyl)piperazine.

The following reagents are available from Acros Organics, Pittsburgh, Pa.: quinoline-6-carboxylic acid and quinoline-5-carboxylic acid.

The following reagent is available from Bachem Bioscience, King of Prussia, Pa.: tert-butoxycarbonyl-β-(3-pyridyl)-alanine.

The following reagents are available from Sigma Chemical Company, Milwaukee, Wis.: N-(3-dimethylaminopropyl)-N'-ethylcarbodiimide hydrochloride and N-tert-butoxycarbonyl)-(N-methyl)-2-aminoacetic acid.

Various abbreviations are used herein. Abbreviations that can be used and their definitions are shown below in Table 2.

TABLE 2

Abbreviations

| Abbreviation | Definition |
|---|---|
| "AM" | acetoxymethyl ester |
| "Boc" | tert-butoxycarbonyl |
| "CIMS" | chemical ionization mass spectrometry |
| "DMF" | dimethylformamide |
| "ESMS" | electrospray mass spectrometry |
| "Et" | an ethyl group |
| "Me" | a methyl group |
| "MH+" | parent ion in ESMS |
| "MS" | mass spectrometry |
| "MTT" | 3-[4,5-dimethyl-thiazoyl-2-yl]2,5-diphenyl-tetrazolium bromide |
| "NIH" | National Institute of Health |
| "PBS" | Phosphate-buffered saline |
| "THF" | tetrahydrofuran |

Reference Example 1

Method for Measuring Activity to Inhibit Pgp (Reversal Assay)

NIH-MDR1-G185 cells (obtained from M. Gottesman, NIH) were harvested and resuspended at $6 \times 10^4$ cells/ml in RPMI 1640 containing L-glutamine, 10% Cosmic calf serum, and penicillin-streptomycin. Cell suspension aliquots of 100 microliters were added to individual wells of a 96 well microtiter plate and incubated overnight at 37° C. to allow cells to adhere. Cell viability in the presence of an anticancer drug was determined in the presence and absence of an MDR modifying agent using an MTT assay (P. A. Nelson, et. al, *J. Immunol*, 150:2139-2147 (1993)).

Briefly, cells were preincubated with an MDR modulating agent (final concentration 5 micromolar) for 15 min at 37° C., then treated with varying concentrations of an anticancer agent for 72 hr at 37° C. MTT dye (20 microliters of 5 mg/ml PBS solution) was added to each well and incubated for 4 hr at 37° C. Media was carefully removed and dye was solubilized with 100 microliters of acidified isopropyl alcohol. Absorption was measured on a spectrophotometric plate reader at 570 nm and corrected for background by subtraction at 630 nm. Reversal index was calculated for each MDR modulator and normalized to the reversal index of a benchmark modulator, VX-710 as below:

Reversal index=$IC_{50}$ in the absence of modulator/$IC_{50}$ in the presence of modulator Normalized reversal index=Reversal index of modulator/Reversal index of VX-710

VX-710 is (S)-N-[2-Oxo-2-(3,4,5-trimethoxyphenyl)acetyl]piperidine-2-carboxylic acid 1,7-bis(3-pyridyl)-4-heptyl ester.

Reference Example 2

Method for Measuring Activity to Inhibit Pgp and MRP1 (Calcein AM Extrusion Assay)

Pgp-dependent calcein AM extrusion was measured in NIH-MDR1-G185 cells or HL60-MDR1 cells. MRP1-dependent calcein AM extrusion was measured in HL60/ADR cells. Dye uptake was measured by incubating $0.5-1 \times 10^6$ cells/ml in cell culture medium containing 0.25 mM calcein AM at 37° C. at an excitation wavelength=493 nm and an emission wavelength=515 nm. Inhibition of calcein AM transport by varying concentrations of MDR modulators was determined by measuring the rate of increase in fluorescence of free calcein for 5 min periods. The $IC_{50}$ values were obtained by determining the concentration of modulator resulting in 50% of the maximum transport inhibition. Maximum transport inhibition was the % inhibition produced in the presence of 50-60 microliters verapmil.

Reference Example 3

Fluorescent Substrate Accumulation Assay

NIH-MDR1-G185 cells (obtained from M. Gottesman, NIH) were harvested and resuspended in RPMI-1640 containing L-glutamine, 10% Cosmic Calf Serum and penicillin-streptomycin. Cell suspension aliquots of 175 microliters ($1 \times 10^5$ cells) were added to individual wells of a 96 well microtiter plate and preincubated for 15 min at 37° C. with 20 microliters MDR modulator diluted in cell culture media to give a final concentration of 10 micromolar. Control wells received no modulating agent. BODIPY-FL Taxol (Molecular Probes, Eugene, Oreg.) was added to each well in 10 microliter aliquots to give a final concentration of 500 nM and cells were incubated for 40 min at 37° C. Cells were centrifuged at 100×g for 5 min at 4° C. and the cell pellet washed with 200 microliters cold PBS to remove fluorescent medium from wells. Cells were centrifuged once more, media removed, and cells resuspended in 200 microliters cold PBS. Fluorescence accumulation was measured in a fluorescence plate reader fitted with an excitation filter of 485 nm and an emission filter of 538 nm. BODIPY-FL taxol accumulation in the cells was calculated as follows:

Accumulation Index=(fluorescence in NIH-MDR1-G185 cells in the presence of modulator)/(fluorescence in NIH-MDR1-G185 cells in absence of modulator)

Reference Example 4

Method for Measuring Substrate Potential for MDR1 (MDR1 ATPase assay)

Recombinant baculovirus carrying the human MDR1 gene was generated and Sf9 cells infected with virus. The virus-infected cells were harvested and their membranes isolated. MDR1-ATPase activity of the isolated Sf9 cell membranes was estimated by measuring inorganic phosphate liberation as previously described (B. Sarkadi, *J. Biol. Chem.*, 1992, 267:4854-4858). The differences between the ATPase activities measured in the absence and presence of 100 micromolar vanadate were determined as activity specific to MDR1. MDR modulator concentrations causing half-maximum activation (Ka) or half-maximum inhibition of the MDR1-ATPase stimulated by 30-40 micromolar verapamil (Ki) were determined.

Example 1

Preparation of 1,7-diphenyl-4-aminoheptane hydrochloride (1)

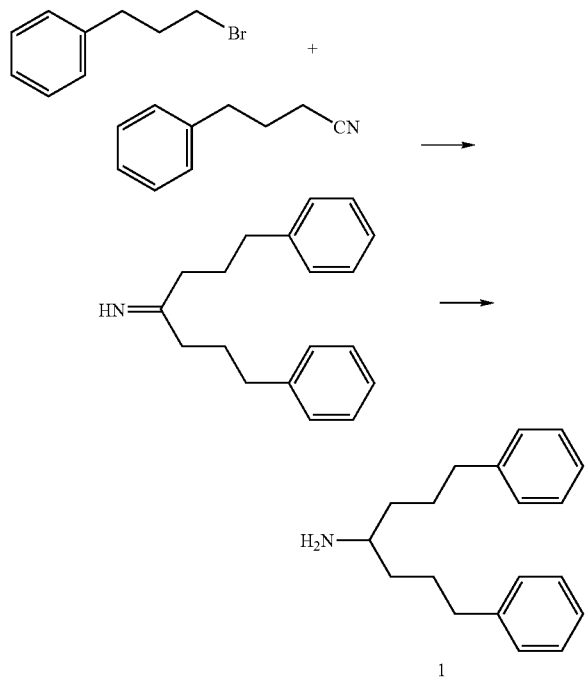

Magnesium (40.2 g, 1.65 mol) and anhydrous ether (3.2 L) are combined in a reaction vessel with stirring. A solution of 1-bromo-3-phenyl propane in 1.6 L of anhydrous ether is added to an addition funnel. The bromide solution is added dropwise to the stirring reaction vessel over a 1 hour period. Upon completion of addition, the mixture stirs for 1-2 hours. A solution of 4-phenylbutyronitrile (160 g, 1.1 mol) in anhydrous ether (2.4 L) is placed in the addition funnel. The solution is added to the reaction vessel over a 1 hour time period. Upon complete addition the solution is heated to reflux for 10 hours, and then stirs at room temperature for six hours. The reaction mixture is diluted with methanol (3.2 L) using an addition funnel. Sodium borohydride (83.4 g, 2.2 mol) is added in portions. Upon complete addition the reaction is stirred at room temperature for six hours. The reaction mixture is quenched by a slow addition of water (3.2 L). The mixture is diluted with ether (3.2 L) and water (1.6 L). The ether layer is separated and the aqueous layer is extracted twice with ether (3.2 L×2). The combined ether extracts are washed once with sodium chloride solution, dried, filtered, and concentrated in vacuo to give the crude product. This product is diluted in ether (1.2 L) and acidified by slow addition of 1M HCl (1.2 L). The mixture stirs for one hour and is concentrated in vacuo. The resulting precipitate is diluted with acetonitrile and is stirred for 16 hours. The desired 1,7-diphenyl-4-aminoheptane hydrochloride is collected by filtration.

Example 2

Preparation of (R)-5-oxiranylmethoxy-quinoline (2)

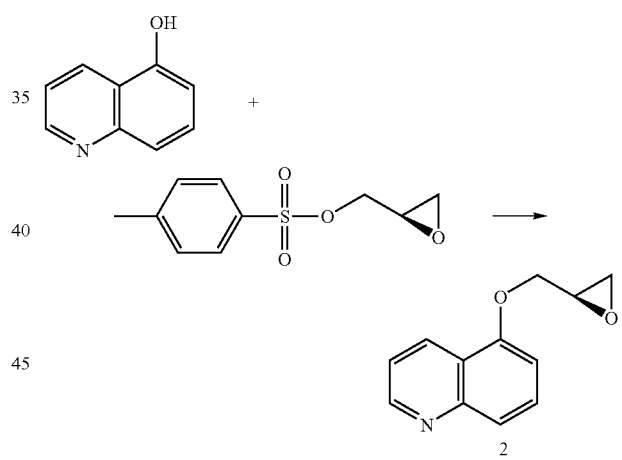

Sodium hydride (60 weight %; 1.79 g; 44.8 mmol) is washed with hexanes (3×10 mL) under an argon blanket. DMF (17 mL) is then added at ambient temperature and the stirred slurry is cooled to 5° C. A solution of 5-hydroxyquinoline (5.00 g; 34.4 mmol) in DMF (65 mL) is added dropwise over 30 minutes. The resulting mixture is allowed to warm to ambient temperature over 1 hour affording a clear, reddish-brown solution. A solution of (R)-(−)-glycidyl tosylate (10.22 g; 44.8 mmol) in DMF (50 mL) is added dropwise over 20 minutes. The resulting mixture is stirred at ambient temperature for 4 hours, quenched by the addition of saturated aqueous ammonium chloride (25 mL), poured onto water (750 mL), and extracted with ether (3×375 mL). The combined ether layers are washed with saturated aqueous sodium bicarbonate (2×375 mL), then dried over $MgSO_4$, filtered, and concentrated in vacuo. The residue is purified via silica gel chromatography with gradient elution (33%→50% ethyl acetate in hexanes) affording the desired product (4.95 g) as a tan solid. ESMS: MH+ 202.2 (base).

Example 3

Preparation of 4-[4-phenyl-1-(3-phenyl-propyl)-butylcarbamoyl]-piperidine-1-carboxylic acid tert-butyl ester (3)

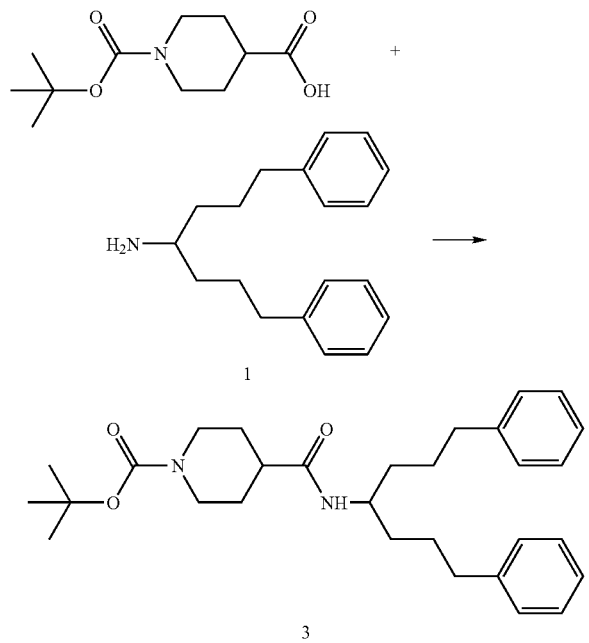

1-tert-Butoxycarbonyl-piperidine-4-carboxylic acid (1 g; 4.36 mmol) is dissolved in methylene chloride (25 mL) at ambient temperature. 1,7-Diphenyl-4-aminoheptane hydrochloride (1) (1.33 g; 4.38 mmol), triethylamine (1.22 mL; 8.75 mmol), and N-(3-dimethylaminopropyl)-N'-ethylcarbodiimide hydrochloride (0.92 g; 4.8 mmol) are added sequentially. The mixture is stirred for 18 hours at ambient temperature then concentrated in vacuo at 40° C. The residue is diluted with ethyl acetate (150 mL) and washed successively with water (150 mL), 0.1 N HCl (100 mL), saturated aqueous sodium bicarbonate (50 mL), and saturated brine (50 mL). The organic layer is dried over MgSO$_4$, filtered, and concentrated in vacuo. The residue is purified via silica gel chromatography with gradient elution (5%→40% ethyl acetate in hexanes) affording the desired product (0.77 g) as a solid.

Example 4

Preparation of piperidine-4-carboxylic acid [4-phenyl-1-(3-phenyl-propyl)-butyl]-amide (4)

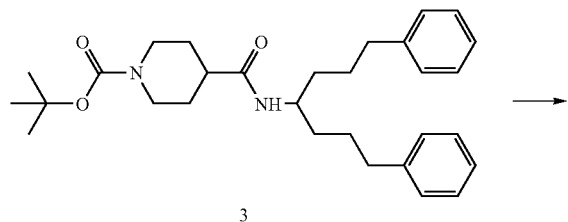

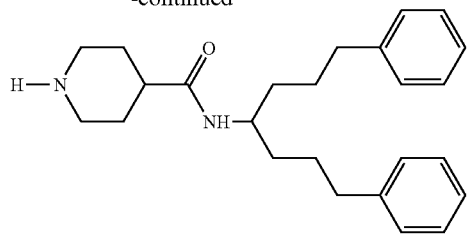

4-[4-Phenyl-1-(3-phenyl-propyl)-butylcarbamoyl]-piperidine-1-carboxylic acid tert-butyl ester (3) (0.77 g; 1.61 mmol) is dissolved in methylene chloride (20 mL) at ambient temperature. Trifluoroacetic acid (20 mL) is added in a slow stream, and the solution is stirred for 90 minutes at ambient temperature. The solution is concentrated in vacuo at 40° C. The residue is slurried in a mixture of methylene chloride (10 mL) and water (100 mL), then potassium carbonate is added until the slurry is alkaline. The slurry is diluted with water (200 mL) then extracted with methylene chloride (3×100 mL). The organic extracts are dried over MgSO$_4$, filtered, and concentrated in vacuo affording the desired product (0.58 g) as an oil.

Example 5

Preparation of (R)-1-[2-hydroxy-3-(quinolin-5-yloxy)-propyl]-piperidine-4-carboxylic acid [4-phenyl-1-(3-phenyl-propyl)-butyl]-amide (5)

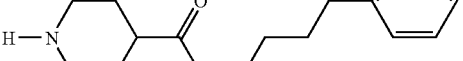

Piperidine-4-carboxylic acid [4-phenyl-1-(3-phenyl-propyl)-butyl]-amide (4) (150.7 mg; 0.4 mmol) is dissolved in isopropanol (10 mL) at ambient temperature. (R)-5-Oxiranylmethoxy-quinoline (2) (79.8 mg; 0.4 mmol) is added, then the mixture is heated to 70° C. and maintained for 18 hours.

After cooling to ambient temperature, the solution is concentrated in vacuo at 40° C. The residue is purified via silica gel chromatography with gradient elution (10%→100% acetone in hexanes) affording the desired product (118.2 mg) as a white solid. ESMS: MH⁺ 580.4 (base).

Example 6

Preparation of 1-[2-hydroxy-3-(3,4,5-trimethoxyphenyl)-propyl]-piperidine-4-carboxylic acid [4-phenyl-1-(3-phenyl-propyl)-butyl]-amide (6)

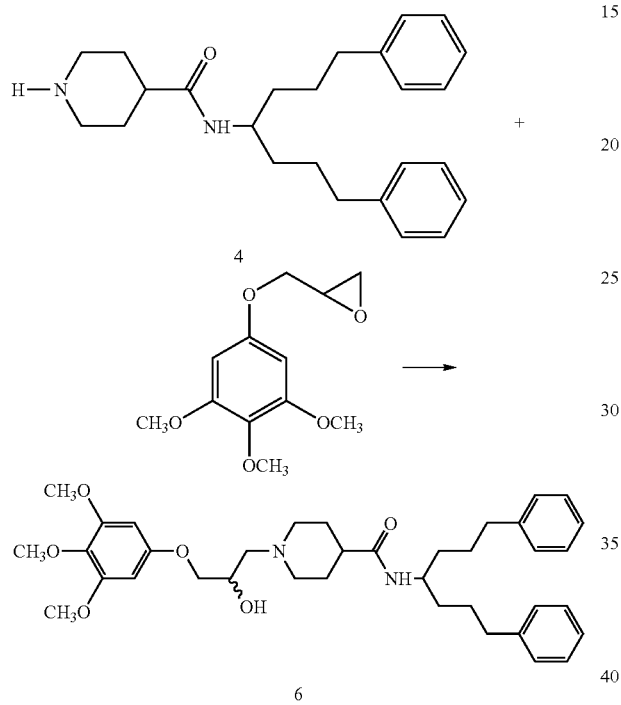

Piperidine-4-carboxylic acid [4-phenyl-1-(3-phenyl-propyl)-butyl]-amide (4) (150.7 mg; 0.4 mmol) is dissolved in isopropanol (10 mL) at ambient temperature. (+/−)-2-(3,4,5-Trimethoxy-phenoxymethyl)-oxirane (95.2 mg; 0.4 mmol) is added, then the mixture is heated to 70° C. and maintained for 18 hours. After cooling to ambient temperature, the solution is concentrated in vacuo at 40° C. The residue is purified via silica gel chromatography with gradient elution (10%→100% acetone in hexanes) affording the desired product (145.9 mg) as an oil. ESMS: MH⁺ 619.4 (base).

Example 7

Preparation of pyridine-3,4-dicarboxylic acid bis-[(4-phenyl-butyl)-amide] (7)

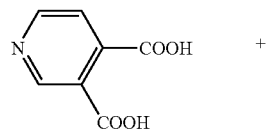

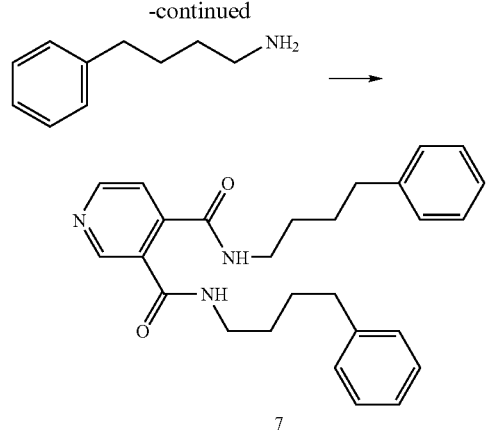

3,4-Pyridinedicarboxylic acid (1 g; 6.0 mmol) is slurried in DMF (50 mL) at ambient temperature. To this reaction mixture is added sequentially 1-hydroxybenzotriazole hydrate (2.43 g; 18.0 mmol), 4-phenylbutylamine (2.08 mL; 13.2 mmol), triethylamine (1.67 mL; 12.0 mmol), and N-(3-dimethylaminopropyl)-N'-ethylcarbodiimide hydrochloride (2.87 g; 15.0 mmol). The reaction mixture is stirred for 18 hours at ambient temperature. The batch is poured onto ethyl acetate (300 mL), then extracted sequentially with water (100 mL), 1N HCl (100 mL), saturated aqueous sodium bicarbonate (50 mL), and brine (50 mL). The organic phase is dried over MgSO₄, filtered, and concentrated in vacuo affording the desired product (2.65 g) as a semi-solid. ESMS: MH⁺ 430.0.

Examples 8 and 9

Preparation of trans-piperidine-3,4-dicarboxylic acid bis[(4-phenyl-butyl)-amide] (8) and cis-piperidine-3,4-dicarboxylic acid bis[(4-phenyl-butyl)-amide] (9)

-continued

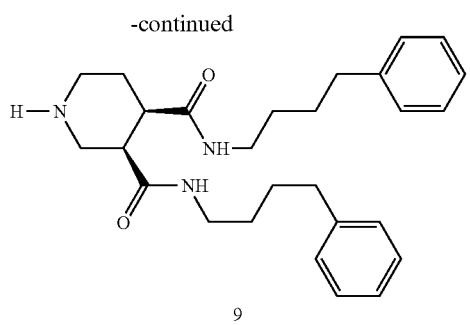

9

Pyridine-3,4-dicarboxylic acid bis-[(4-phenyl-butyl)-amide] (7) (0.46 g; 1.07 mmol) is combined with ethanol (20 mL) and 20% Pd(OH)$_2$ on carbon (0.4 g) in a hydrogenation bottle. The mixture is hydrogenated at 50 psi for 18 hours, then additional 20% Pd(OH)$_2$ on carbon (0.25 g) is added to the mixture and the hydrogenation is resumed for an additional 18 hours. The mixture is filtered through a celite pad and washed with ethanol. The combined filtrate plus wash is concentrated in vacuo. The residue is purified via silica gel chromatography with gradient elution (5%→100% methanol in methylene chloride) affording the desired products as separable diastereomers.

The first eluted diastereomer is (8) 70.9 mg; ESMS: MH$^+$ 436.4 (base). The second eluted diastereomer is (9) 78.1 mg; ESMS: MH$^+$ 436.4 (base).

Example 10

Preparation of trans-(R)-1-[2-hydroxy-3-(quinolin-5-yloxy)-propyl]-piperidine-3,4-dicarboxylic acid bis-[(4-phenyl-butyl)-amide] (10)

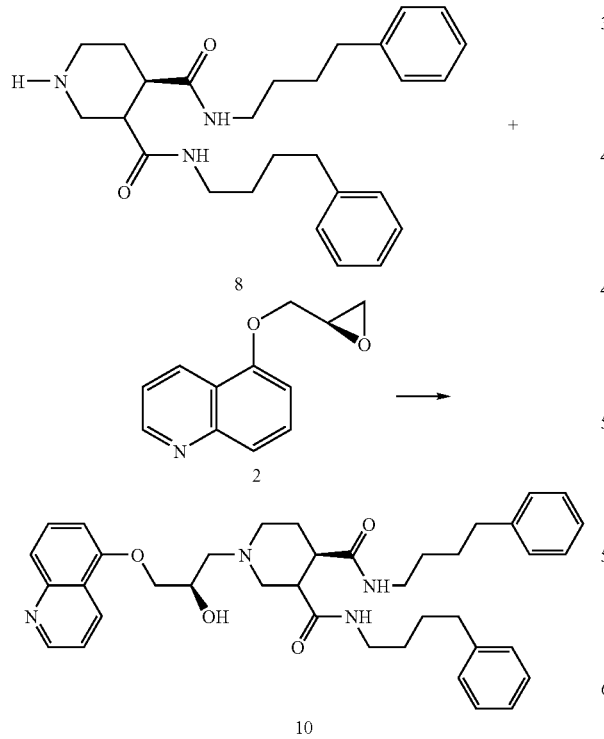

trans-Piperidine-3,4-dicarboxylic acid bis[(4-phenyl-butyl)-amide] (8) (78.1 mg; 0.179 mmol) is dissolved in isopropanol (10 mL) at ambient temperature. (R)-5-Oxiranyl-methoxy-quinoline (2) (36.1 mg; 0.179 mmol) is added then the mixture is heated to 70° C. and maintained for 18 hours. After cooling to ambient temperature the solution is concentrated in vacuo at 40° C. The residue is purified via silica gel chromatography with gradient elution (0%→50% methanol in methylene chloride) affording the desired product (69.6 mg) as a solid. ESMS: MH$^+$ 637.4 (base).

Example 11

Preparation of cis-(R)-1-[2-hydroxy-3-(quinolin-5-yloxy)-propyl]-piperidine-3,4-dicarboxylic acid bis-[(4-phenyl-butyl)-amide] (11)

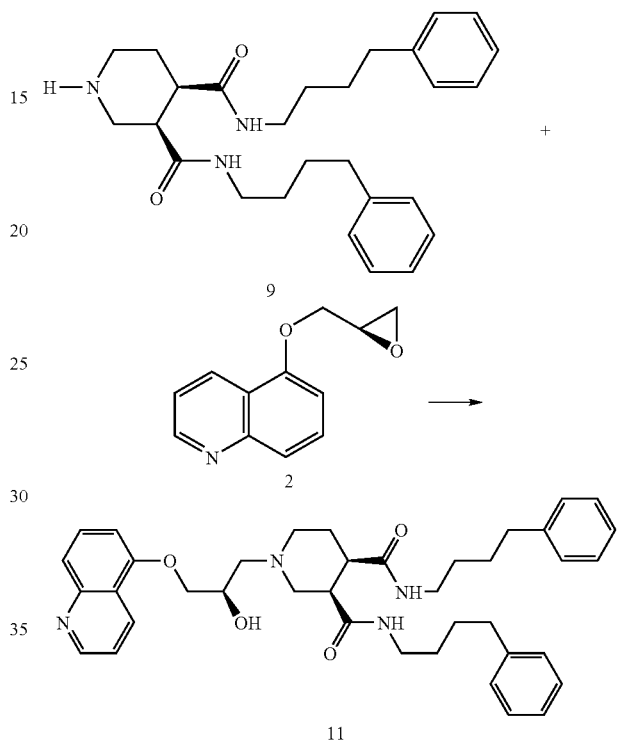

cis-Piperidine-3,4-dicarboxylic acid bis[(4-phenyl-butyl)-amide] (9) (70.9 mg; 0.163 mmol) is dissolved in isopropanol (10 mL) at ambient temperature. (R)-5-Oxiranylmethoxy-quinoline (2) (32.8 mg; 0.163 mmol) is added then the mixture is heated to 70° C. and maintained for 18 hours. After cooling to ambient temperature the solution is concentrated in vacuo at 40° C. The residue is purified via silica gel chromatography with gradient elution (0%→50% methanol in methylene chloride) affording the desired product (86.0 mg) as an oil. ESMS: MH$^+$ 637.4 (base).

Example 12

Preparation of 3-[4-phenyl-1-(3-phenyl-propyl)-butylcarbamoyl]-piperidine-1-carboxylic acid tert-butyl ester (12)

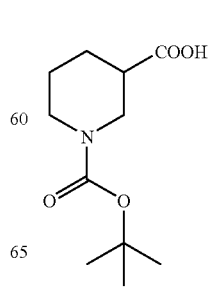

-continued

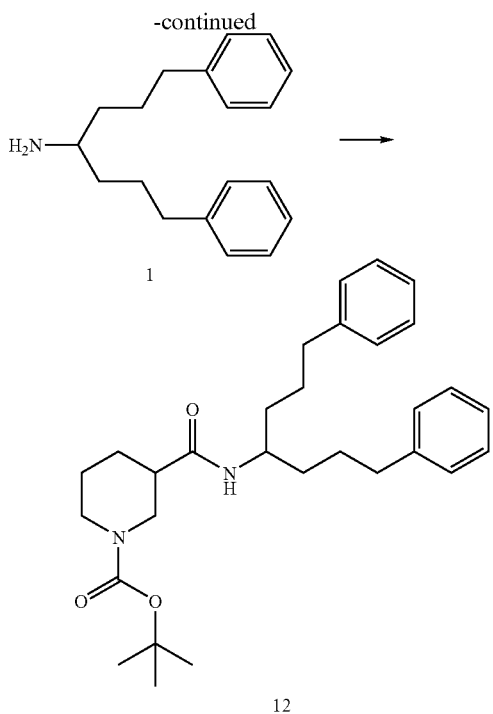

1-tert-Butoxycarbonyl-piperidine-3-carboxylic acid (1 g; 4.36 mmol) is dissolved in methylene chloride (50 mL) at ambient temperature. 1,7-Diphenyl-4-aminoheptane hydrochloride (1) [1.33 g; 4.36 mmol], triethylamine (0.61 mL; 4.36 mmol), and N-(3-dimethylaminopropyl)-N'-ethylcarbodiimide hydrochloride (0.84 g; 4.4 mmol) are added sequentially. The mixture is stirred for 18 hours at ambient temperature then concentrated in vacuo at 30° C. The residue is diluted with ethyl acetate (100 mL) and washed successively with water (200 mL), saturated aqueous sodium bicarbonate (50 mL), and saturated brine (50 mL). The organic layer is dried over MgSO$_4$, filtered, and concentrated in vacuo. The residue is purified via silica gel chromatography with gradient elution (5%→40% ethyl acetate in hexanes) affording the desired product (1.30 g) as a viscous oil. ESMS: MH$^+$ 479.4

Example 13

Preparation of piperidine-3-carboxylic acid [4-phenyl-1-(3-phenyl-propyl)-butyl]-amide (13)

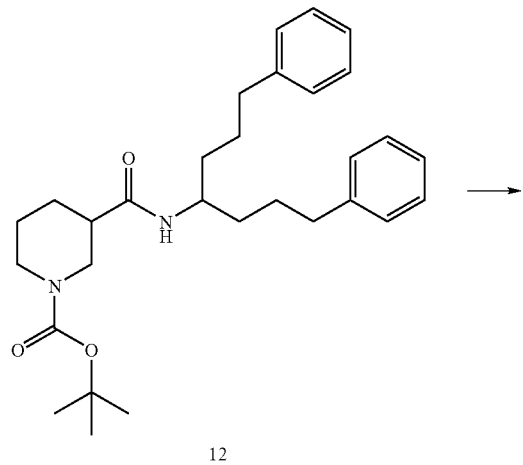

-continued

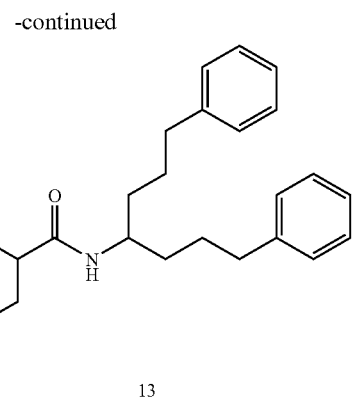

3-[4-Phenyl-1-(3-phenyl-propyl)-butylcarbamoyl]-piperidine-1-carboxylic acid tert-butyl ester (12) (0.202 g; 0.42 mmol) is dissolved in methylene chloride (5 mL) at ambient temperature. Trifluoroacetic acid (5 mL) is added in a slow stream, and the solution is stirred for 90 minutes at ambient temperature. The solution is concentrated in vacuo at 40° C. The residue is slurried in a mixture of methylene chloride (10 mL) and water (100 mL), then potassium carbonate is added until the slurry is alkaline. The slurry is diluted with water (50 mL) then extracted with methylene chloride (3×50 mL). The organic extracts are dried over MgSO$_4$, filtered, and concentrated in vacuo affording the desired product (0.147 g) as an oil.

Example 14

Preparation of (R)-1-[2-hydroxy-3-(quinolin-5-yloxy)-propyl]-piperidine-3-carboxylic acid [4-phenyl-1-(3-phenyl-propyl)-butyl-amide (14)

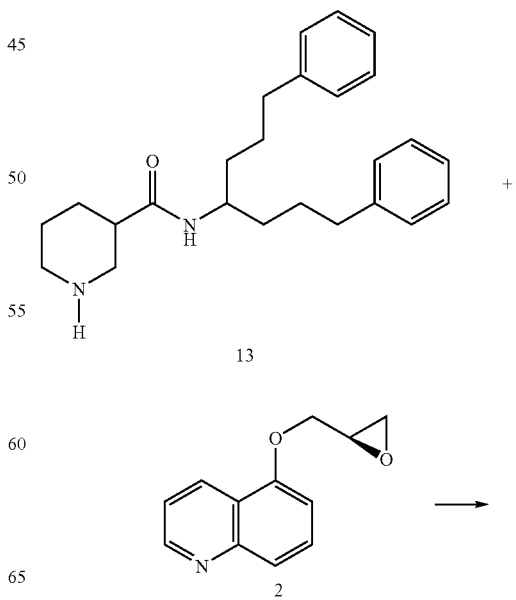

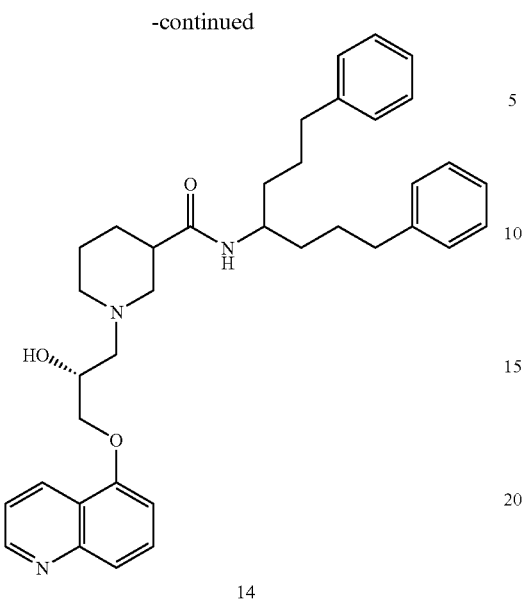

14

Piperidine-3-carboxylic acid [4-phenyl-1-(3-phenyl-propyl)-butyl]-amide (13) (146.6 mg; 0.39 mmol) is dissolved in isopropanol (10 mL) at ambient temperature. (R)-5-Oxiranylmethoxy-quinoline (2) (80.0 mg; 0.39 mmol) is added, then the mixture is heated to 70° C. and maintained for 18 hours. After cooling to ambient temperature, the solution is concentrated in vacuo at 40° C. The residue is purified via silica gel chromatography with gradient elution (10%→100% acetone in hexanes) affording the desired product as a solid. ESMS: MH+ 580.4 (base).

Example 15

Preparation of (R)-1-[2-hydroxy-3-(3,4,5-trimethoxyphenyl)-propyl]-piperidine-3-carboxylic acid [4-phenyl-1-(3-phenyl-propyl)-butyl-amide (15)

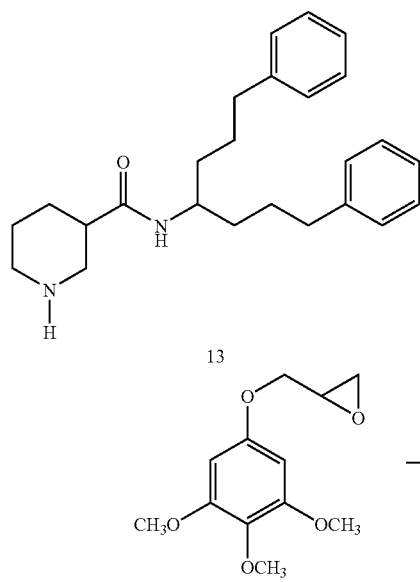

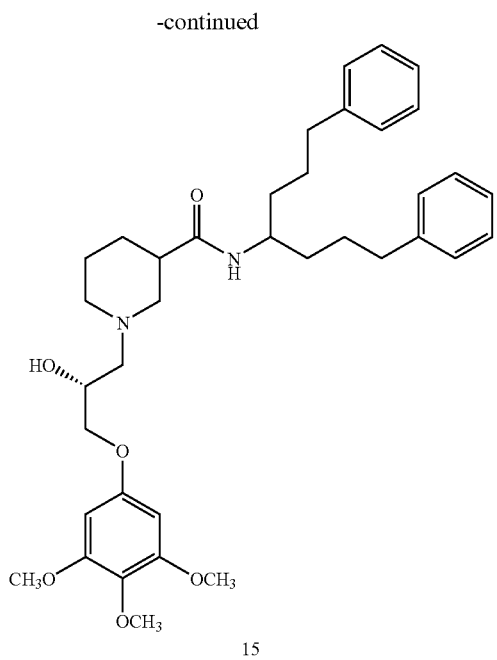

15

Piperidine-3-carboxylic acid [4-phenyl-1-(3-phenyl-propyl)-butyl]-amide (13) (150 mg; 0.4 mmol) is dissolved in isopropanol (10 mL) at ambient temperature. (R)-2-(3,4,5-Trimethoxy-phenoxymethyl)-oxirane (95.2 mg; 0.4 mmol) is added, then the mixture is heated to 70° C. and maintained for 18 hours. After cooling to ambient temperature, the solution is concentrated in vacuo at 40° C. The residue is purified via silica gel chromatography with gradient elution (1%→20% methanol in methylene chloride) affording the desired product (220.3 mg) as an oil. ESMS: MH+ 619.4 (base).

Example 16

Preparation of 1-(3-pyridin-3-yl-propionyl)-piperidine-3-carboxylic acid [4-phenyl-1-(3-phenyl-propyl)-butyl]-amide (16)

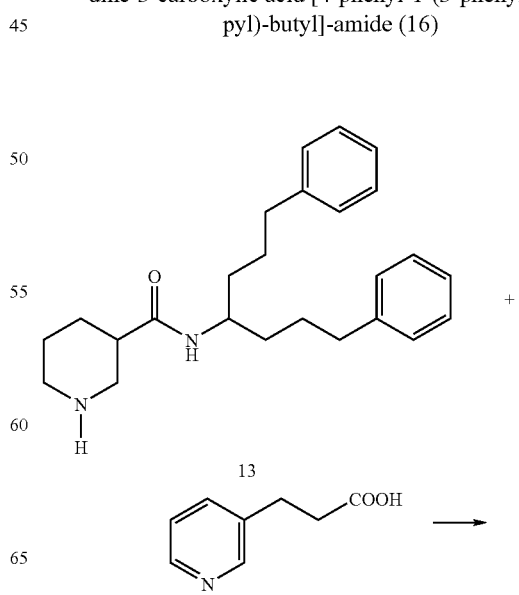

-continued

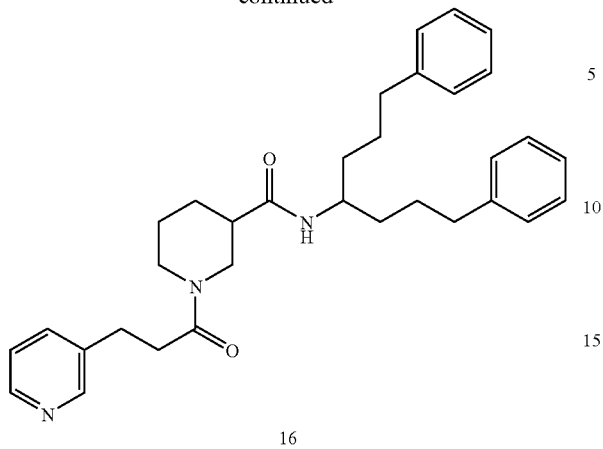

16

Piperidine-3-carboxylic acid [4-phenyl-1-(3-phenyl-propyl)-butyl]-amide (13) (150 mg; 0.4 mmol) is dissolved in methylene chloride (10 mL) at ambient temperature. 3-Pyridinepropionic acid (60.0 mg; 0.4 mmol), triethylamine (0.111 mL; 0.4 mmol), and N-(3-dimethylaminopropyl)-N'-ethylcarbodiimide hydrochloride (0.0836 g; 0.4 mmol) are added sequentially. The mixture is stirred for 18 hours at ambient temperature then diluted with methylene chloride (90 mL) and washed successively with water (40 mL), saturated aqueous sodium bicarbonate (40 mL), and saturated brine (25 mL). The organic layer is dried over MgSO₄, filtered, and concentrated in vacuo. The residue is purified via silica gel chromatography with gradient elution (1%→20% methanol in methylene chloride) affording the desired product (138.4 mg) as an oil. ESMS: MH⁺ 512.4 (base).

Example 17

Preparation of quinoline-6-carboxylic acid oxiranylmethyl ester (17)

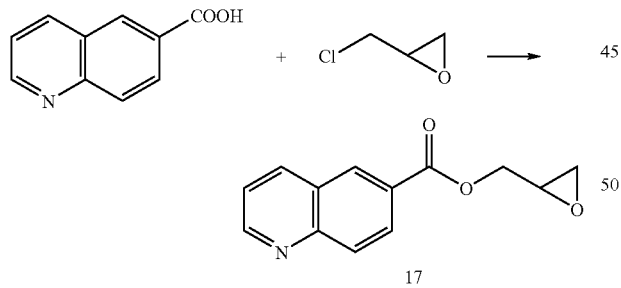

Quinoline-6-carboxylic acid (1 g; 5.78 mmol) is dissolved in DMF (10 mL) at ambient temperature. Epichlorohydrin (0.4517 mL; 5.59 mmol) is added followed by mortar ground potassium carbonate (0.80 g; 5.79 mmol). The mixture is stirred at ambient temperature for 48 hours. Potassium iodide (96 mg; 0.58 mmol) is added and stirring is continued at ambient temperature for 24 hours. The mixture is heated to 60° C. and maintained for 72 hours. After cooling, the mixture is poured onto water (700 mL) and extracted with ethyl acetate (3×100 mL). The combined organic extracts are washed successively with water (100 mL), and brine (50 mL), then dried over MgSO₄, filtered, and concentrated in vacuo at 30C. The residue is purified via silica gel chromatography with gradient elution (20%→67% ethyl acetate in hexanes) affording the desired product (270 mg) as a white solid. ESMS: MH⁺ 230.0 (base).

Example 18

Preparation of quinoline-6-carboxylic acid 2-hydroxy-3-{3-[4-phenyl-1-(3-phenyl-propyl)-butylcarbamoyl]-piperidin-1-yl}-propyl ester (18)

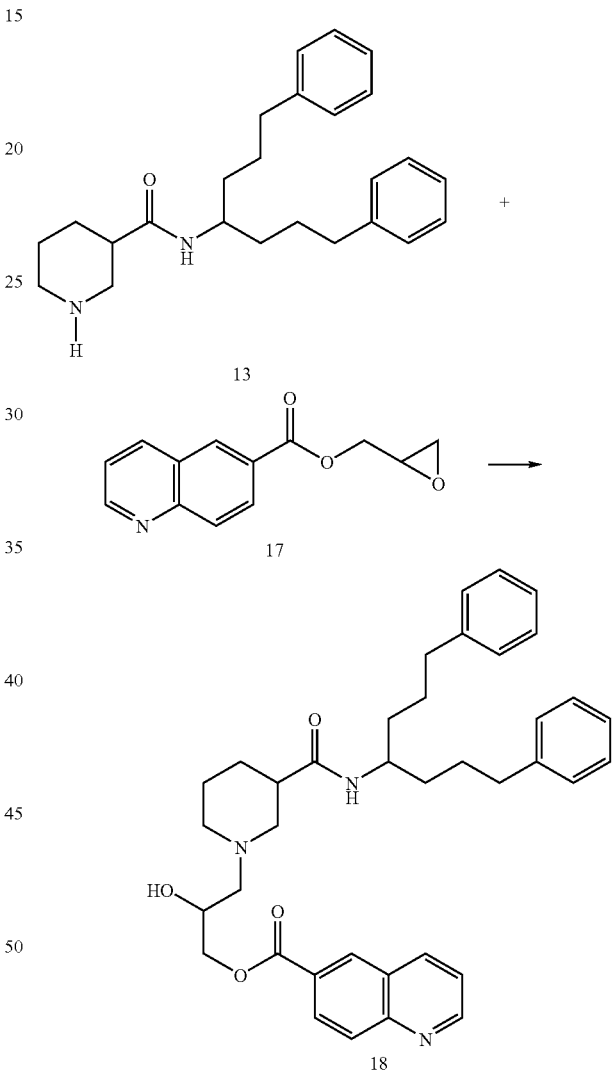

Piperidine-3-carboxylic acid [4-phenyl-1-(3-phenyl-propyl)-butyl]-amide (13) (150 mg; 0.4 mmol) is dissolved in isopropanol (10 mL) at ambient temperature. Quinoline-6-carboxylic acid oxiranylmethyl ester (17) (90.8 mg; 0.4 mmol) is added, then the mixture is heated to 70° C. and maintained for 18 hours. After cooling to ambient temperature, the solution is concentrated in vacuo at 40° C. The residue is purified via silica gel chromatography with gradient elution (1%→20% methanol in methylene chloride) affording the desired product (203.4 mg) as an oil. ESMS: MH⁺ 608.4 (base).

Example 19

Preparation of (1-benzyl-2-hydroxy-3-{3-[4-phenyl-1-(3-phenyl-propyl)-butylcarbamoyl]-piperidine-1-yl}-propyl)-carbamic acid tert-butyl ester (19)

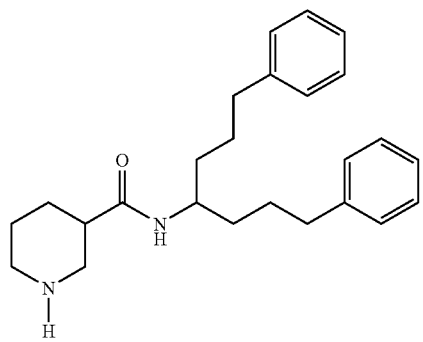

13

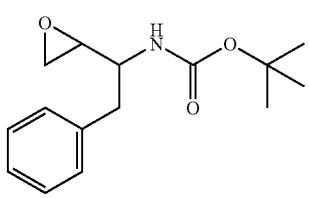

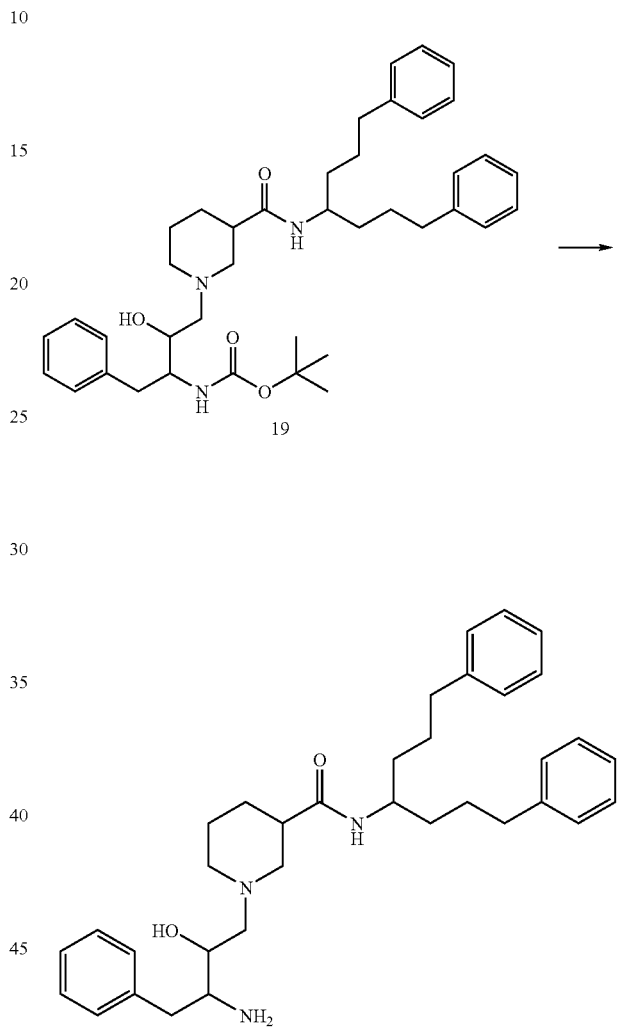

Example 20

Preparation of 1-(3-amino-2-hydroxy-4-phenyl-butyl)-piperidine-3-carboxylic acid [4-phenyl-1-(3-phenyl-propyl)-butyl]-amide (20)

Piperidine-3-carboxylic acid [4-phenyl-1-(3-phenyl-propyl)-butyl]-amide (13) (150 mg; 0.4 mmol) is dissolved in isopropanol (10 mL) at ambient temperature. tert-Butyl[S-(R*, R*)]-(−)-(1-oxiranyl)-2-phenylethyl)carbamate (104.4 mg; 0.4 mmol) is added, then the mixture is heated to 70° C. and maintained for 18 hours. After cooling to ambient temperature, the solution is concentrated in vacuo at 40° C. The residue is purified via silica gel chromatography with gradient elution (1%→20% methanol in methylene chloride) affording the desired product (166.7 mg) as an oil. ESMS: MH+ 642.6 (base).

(1-Benzyl-2-hydroxy-3-{3-[4-phenyl-1-(3-phenyl-propyl)-butylcarbamoyl]-piperidine-1-yl}-propyl)-carbamic acid tert-butyl ester (19) (194.4 mg; 0.3 mmol) is dissolved in methylene chloride (5 mL) at ambient temperature. Trifluoroacetic acid (5 mL) is added in a slow stream, and the solution is stirred for 90 minutes at ambient temperature. The solution is concentrated in vacuo at 40° C. The residue is slurried in a mixture of methylene chloride (10 mL) and water (100 mL), then potassium carbonate is added until the slurry is alkaline. The slurry is diluted with water (50 mL) then extracted with methylene chloride (3×50 mL). The organic extracts are dried over MgSO4, filtered, and concentrated in vacuo affording the desired product (150 mg) as an oil.

Example 21

Preparation of quinoline-6-carboxylic acid (1-benzyl-2-hydroxy-3-{3-[-phenyl-1-(3-phenyl-propyl)-butylcarbamoyl]-piperidin-1-yl}-propyl)-amide (21)

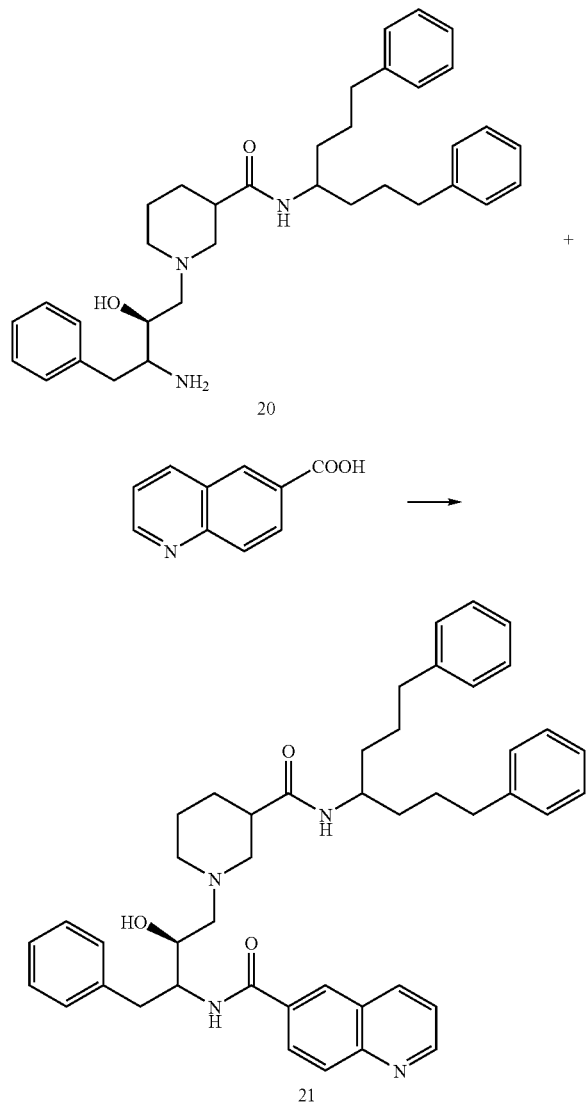

1-(3-Amino-2-hydroxy-4-phenyl-butyl)-piperidine-3-carboxylic acid [4-phenyl-1-(3-phenyl-propyl)-butyl]-amide (20) (150 mg; 0.28 mmol) is dissolved in methylene chloride (10 mL) at ambient temperature. 6-Quinolinecarboxylic acid (48 mg; 0.28 mmol), triethylamine (0.0772 mL; 0.55 mmol), and N-(3-Dimethylaminopropyl)-N'-ethylcarbodiimide hydrochloride (58.4 mg; 0.31 mmol) are added sequentially. The mixture is stirred for 18 hours at ambient temperature then concentrated in vacuo at 30° C. The residue is diluted with ethyl acetate (100 mL) and washed successively with water (50 mL), saturated aqueous sodium bicarbonate (50 mL), and saturated brine (50 mL). The organic layer is dried over MgSO₄, filtered, and concentrated in vacuo. The residue is purified via silica gel chromatography with gradient elution (2%→20% methanol in methylene chloride) affording the desired product diastereomers (70 mg) as an oil. ESMS: MH+ 697.6 (base).

Example 22

Preparation of 5-phenyl-2-(3-phenyl-propyl)-pentanoic acid (22)

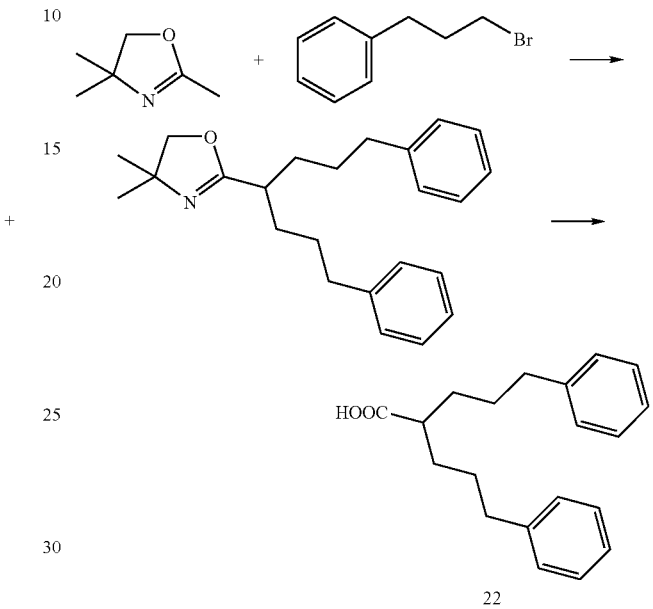

2,2,4-Trimethyl-2-oxazoline (5.64 mL; 44.2 mmol) is dissolved in THF (40 mL) in a dry, argon purged flask at ambient temperature. The solution is cooled to −78° C., then n-butyllithium in hexanes (31.3 mL of 1.6 M solution; 50 mmol) is added dropwise via syringe, followed by a solution of 1-bromo-3-phenylpropane (7.42 mL; 48.8 mmol) in THF (20 mL) dropwise via syringe. The cooling bath is removed and the solution is allowed to slowly warm to ambient temperature. After approximately 30 minutes, the reaction is cooled to −78° C., then n-butyllithium in hexanes (31.3 mL of 1.6 M solution; 50 mmol) is added dropwise via syringe, followed by a solution of 1-bromo-3-phenylpropane (7.42 mL; 48.8 mmol) in THF (20 mL) dropwise via syringe. The reaction mixture is stirred overnight with very slow warming to ambient temperature. The solution is poured onto water (200 mL) and 1N HCl is added to make the mixture acidic. The mixture is extracted with ether (150 mL), then made alkaline with 50% aqueous sodium hydroxide solution. The alkaline mixture is extracted with ether (3×100 mL). The combined ether extracts are dried over MgSO₄, filtered, and concentrated in vacuo. The residue is purified via silica gel chromatography with gradient elution (0%→33% ethyl acetate in hexanes) affording the dialkylated oxazoline intermediate (13.55 g) as a colorless liquid. ESMS: MH⁺ 349.6 (base). The dialkylated oxazoline intermediate (1 g; 2.86 mmol) is dissolved in dioxane (10 mL) at ambient temperature. 3N HCl (20 mL) is added and the solution is heated to gentle reflux for 18 hours. After cooling, the reaction mixture is poured onto water (20 mL) and extracted with ether (3×30 mL). The combined ether extracts are washed successively with water (20 mL), and brine (20 mL), then dried over MgSO₄, filtered, and concen-

Example 23

Preparation of 5-phenyl-2-(3-phenyl-propyl)-pentanoic acid (1-benzyl-piperidin-4-yl)-amide (23)

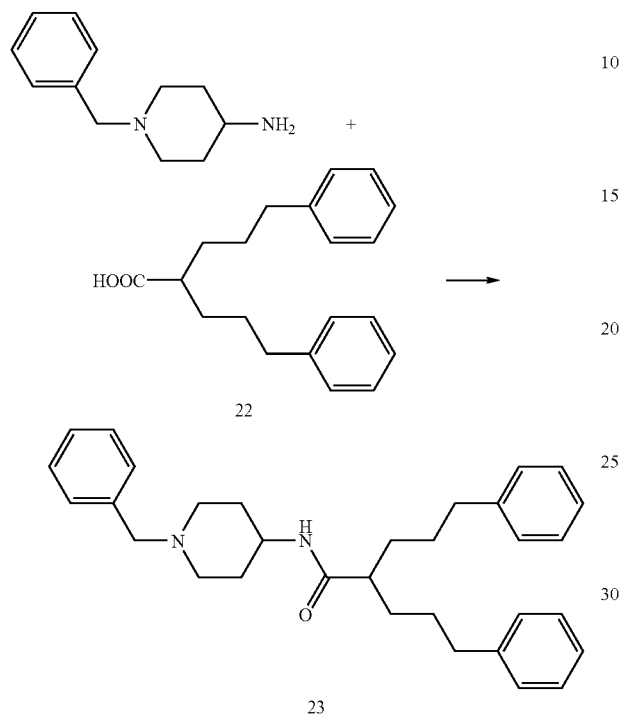

1-Benzyl-4-aminopiperidine (0.5 g; 2.63 mmol) is dissolved in DMF (25 mL) at ambient temperature. 5-Phenyl-2-(3-phenyl-propyl)-pentanoic acid (22) (0.78 g; 2.62 mmol), triethylamine (0.46 mL; 3.28 mmol), 1-hydroxybenzotriazole (0.444 g; 3.28 mmol), and N-(3-dimethylaminopropyl)-N'-ethylcarbodiimide hydrochloride (0.554 g; 2.89 mmol) are added sequentially. The mixture is stirred for 18 hours at ambient temperature then poured onto ethyl acetate (250 mL) and extracted successively with water (50 mL), saturated aqueous sodium bicarbonate (50 mL), and brine (50 mL), then dried over MgSO$_4$, filtered, and concentrated in vacuo. The residue is purified via silica gel chromatography with gradient elution (10%→67% ethyl acetate in hexanes) affording the desired product (1.07 g) as a white solid. ESMS: MH+ 469.4 (base).

Example 24

Preparation of 5-phenyl-2-(3-phenyl-propyl)-pentanoic acid piperidin-4-ylamide (24)

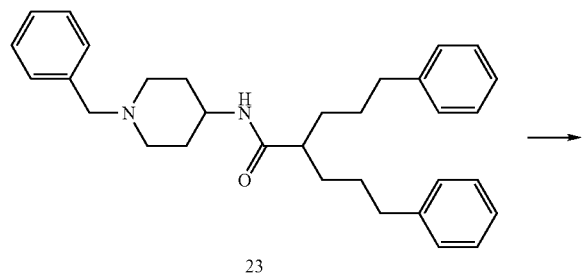

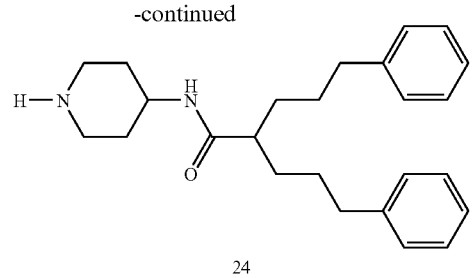

5-Phenyl-2-(3-phenyl-propyl)-pentanoic acid (1-benzyl-piperidin-4-yl)-amide (23) (0.5 g; 1.07 mmol) is combined with ethanol (25 mL) and 20% Pd(OH)$_2$ on carbon (0.2 g) in a hydrogenation bottle. The mixture is hydrogenated at 50 psi for 18 hours then filtered through a celite pad and washed with ethanol. The combined filtrate plus wash is concentrated in vacuo affording the desired product (0.38 g) as an oil. ESMS: MH$^+$ 379.4 (base).

Example 25

Preparation of 5-phenyl-2-(3-phenyl-propyl)-pentanoic acid {1-[2-hydroxy-3-(quinolin-5-yloxy)-propyl]-piperidin-4-yl}-amide (25)

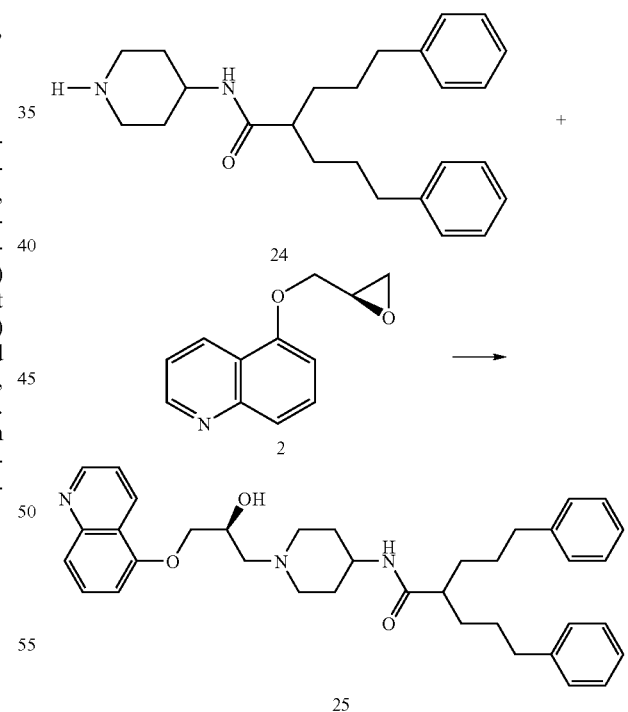

5-Phenyl-2-(3-phenyl-propyl)-pentanoic acid piperidin-4-ylamide (24) (100 mg; 0.264 mmol) is dissolved in isopropanol (10 mL) at ambient temperature. (R)-5-Oxiranylmethoxyquinoline (2) (53.2 mg; 0.264 mmol) is added, then the mixture is heated to 70° C. and maintained for 18 hours. After cooling to ambient temperature, the solution is concentrated in vacuo at 40° C. The residue is purified via silica gel chromatography with gradient elution (0%→25% methanol in methylene chloride) affording the desired product (117 mg) as a solid. ESMS: MH+ 580.4 (base).

Example 26

Preparation of 1-(3,4,5-trimethoxyglyoxyl)-piperidine-3-carboxylic acid [4-phenyl-1-(3-phenyl-propyl)-butyl]-amide (26)

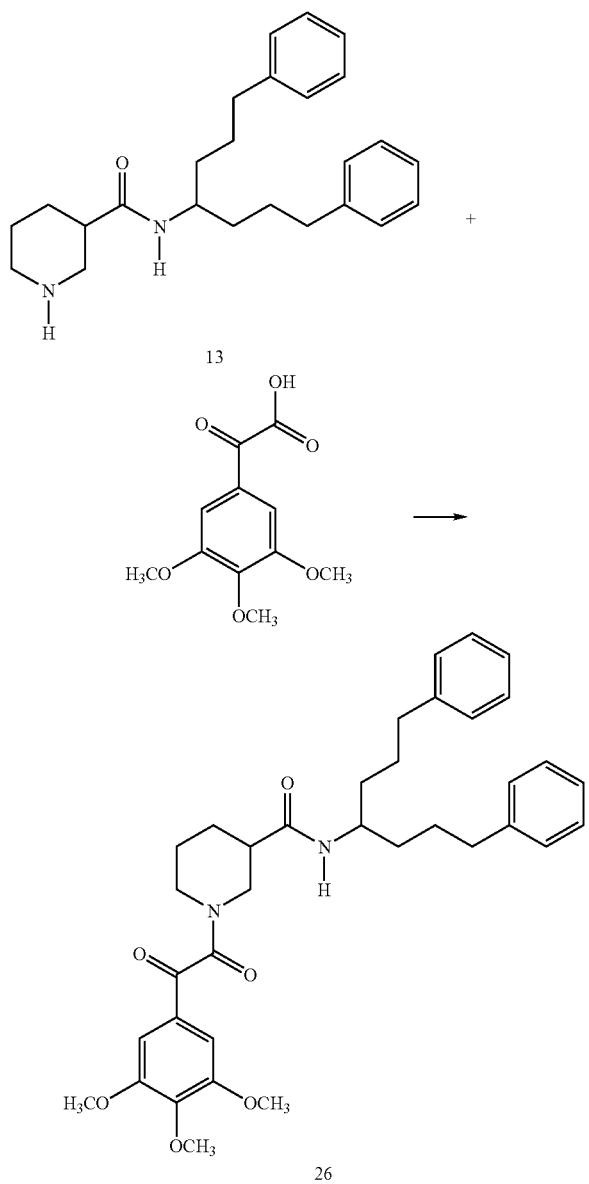

Piperidine-3-carboxylic acid [4-phenyl-1-(3-phenyl-propyl)-butyl]-amide (13) (0.46 g; 1.23 mmol) is dissolved in N,N-dimethylformamide (25 mL) at ambient temperature. 3',4',5'-Trimethoxyphenylglyoxylic acid (0.29 g; 1.23 mmol), N,N-diisopropylethylamine (0.31 g; 2.43 mmol) and PyBOP (0.63 g; 17.0 mmol) are added sequentially. The reaction is stirred for 18 hr. at room temperature, then poured onto ice-cold 0.1N HCl (150 mL) and extracted with ethyl acetate (150 mL). The layers are separated and the organic layer washed successively with brine (100 mL), saturated NaHCO$_3$ solution (150 mL) and brine (100 mL). The organic solution is dried over MgSO$_4$, filtered and concentrated under reduced pressure. Purification of the product by chromatography on silica gel (4:6 hexane:ethyl acetate) affords the desired amide (26). MS (NH$_3$CI): 601 (MH+)

Example 27

Preparation of 1-(3-butenoyl)-piperidine-4-carboxylic acid [4-phenyl-1-(3-phenyl-propyl)-butyl]-amide (27)

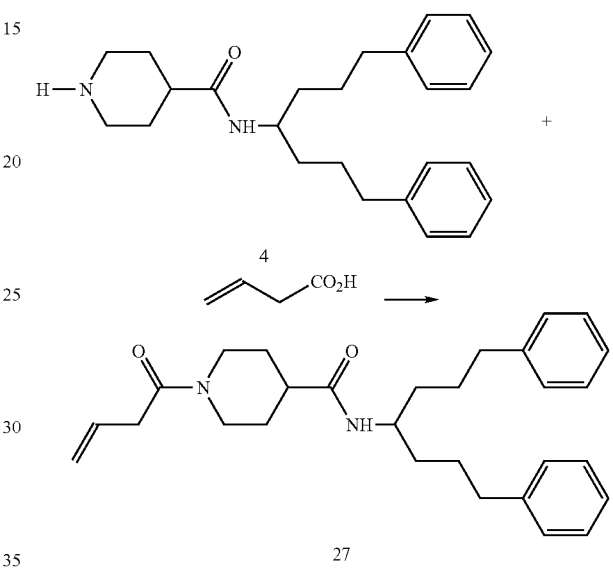

Piperidine-4-carboxylic acid [4-phenyl-1-(3-phenyl-propyl)-butyl]-amide (4) (1.00 g; 2.64 mmol) is dissolved in methylene chloride (30 mL) at ambient temperature. 3-Butenoic acid (0.27 g; 3.17 mmol), N,N-diisopropylethylamine (0.75 g; 5.81 mmol) and PyBOP (1.65 g; 3.17 mmol) are added sequentially. The reaction is stirred for 27 hr. at room temperature, then concentrated under reduced pressure. The residue is purified via silica gel chromatography with gradient elution (70%→90% ethyl acetate in hexanes) affording the desired product (27) as a solid. CIMS (NH$_3$CI): 447 (MH+)

Example 28

Preparation of 1-(oxiranylacetyl)-piperidine-4-carboxylic acid [4-phenyl-1-(3-phenyl-propyl)-butyl]-amide (28)

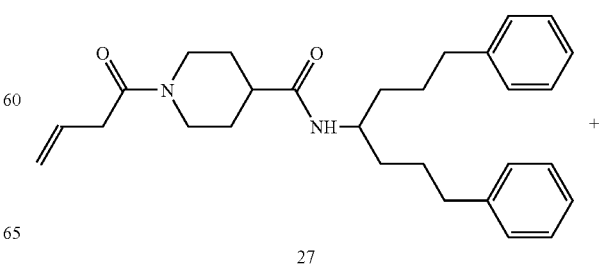

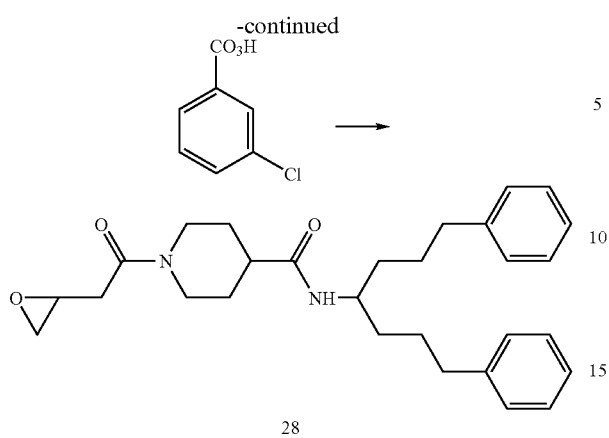

1-(3-Butenoyl)-piperidine-4-carboxylic acid [4-phenyl-1-(3-phenyl-propyl)-butyl]-amide (27) (1.00 g; 2.24 mmol) and m-chloroperbenzoic acid (Aldrich Chemical Company; 71% by assay; 0.65 g; 2.91 mmol) are combined in 10 mL of methylene chloride and refluxed for 24 hours. The solution is stirred at ambient temperature for 72 hours, diluted with methylene chloride (50 mL) and shaken with 10% aqueous Na$_2$SO$_3$ (50 mL). The methylene chloride layer is separated and washed successively with saturated aqueous NaHCO$_3$ solution and brine. The organic layer is dried over MgSO$_4$, filtered and concentrated in vacuo. The residue is purified by chromatography on silica gel using a gradient elution (80%→90% ethyl acetate in hexanes, then 50%→60% acetone in hexanes) affording 28 as a solid. CIMS (NH$_3$CI): 463 (MH$^+$)

Example 29

Preparation of 1-{3-hydroxy-4-[2-(1,2,3,4-tetrahydroisoguinoline)]-butyryl}-piperidine-4-carboxylic acid [4-phenyl-1-(3-phenyl-propyl)-butyl]-amide (29)

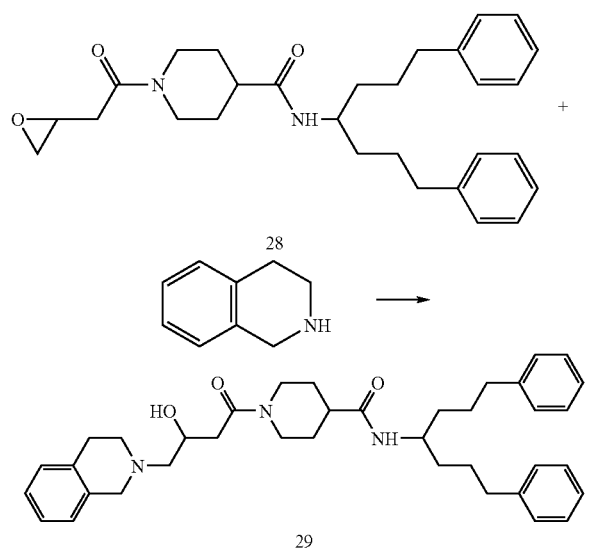

1-(Oxiranylacetyl)-piperidine-4-carboxylic acid [4-phenyl-1-(3-phenyl-propyl)-butyl]-amide (28) (100 mg; 0.216 mmol) and 1,2,3,4-tetrahydroisoquinoline (28.8 mg; 0.216 mmol) are combined in absolute ethanol (10 mL) and refluxed for 18 hours. After cooling to ambient temperature, the solution is concentrated in vacuo at 40° C. The residue is chromatographed on silica gel with a gradient elution (80%→90% ethyl acetate in hexanes, then 50%→60% acetone in hexanes) affording the desired product (29) as a solid. CIMS (NH$_3$CI): 596 (MH$^+$)

Example 30

Preparation of (R)-1-[2-hydroxy-3-(quinolin-5-yloxy)-propyl]-piperidine-4-carboxylic acid ethyl ester (31)

Piperidine-4-carboxylic acid ethyl ester (30) (0.75 g; 4.77 mmol) and (R)-5-oxiranylmethoxy-quinoline (2) 0.96 g; 4.77 mmol) are combined in 95 mL of absolute ethanol. The mixture is heated to reflux for 8 hours. After cooling to ambient temperature, the solution is concentrated in vacuo at 40° C. The residue is chromatographed on silica gel with a gradient elution (90% ethyl acetate in hexanes, then 50%→60% acetone in hexanes) affording the desired product (29) as an oil. CIMS (NH$_3$CI): 359 (MH$^+$)

Example 31

Preparation of lithium (R)-1-[2-hydroxy-3-(quinolin-5-yloxy)-propyl]-piperidine-4-carboxylate (32)

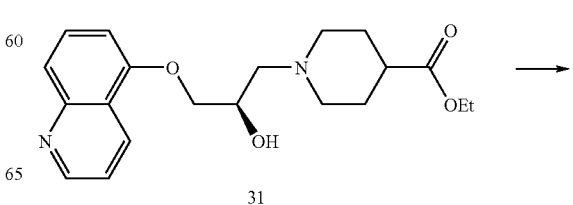

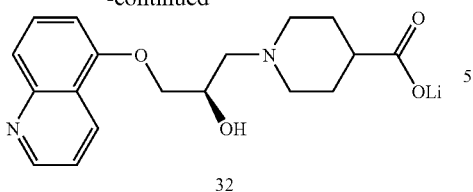

(R)-1-[2-Hydroxy-3-(quinolin-5-yloxy)-propyl]-piperidine-4-carboxylic acid ethyl ester (31) (1.15 g; 3.21 mmol) is dissolved in 21 mL of a 40:40:20 mixture of tetrahydrofuran:water:methanol. Lithium hydroxide (81 mg; 3.37 mmol) is added and the mixture stirred at ambient temperature. After 4.5 hours, the mixture is concentrated in vacuo at 40° C. Further drying on the vacuum pump affords the desired product (32) as a white solid.

Example 32

Preparation of (R)-1-[2-hydroxy-3-(quinolin-5-yloxy)-propyl]-piperidine-4-carboxylic acid 4-[1-(diphenylmethyl)-piperazine] amide (34)

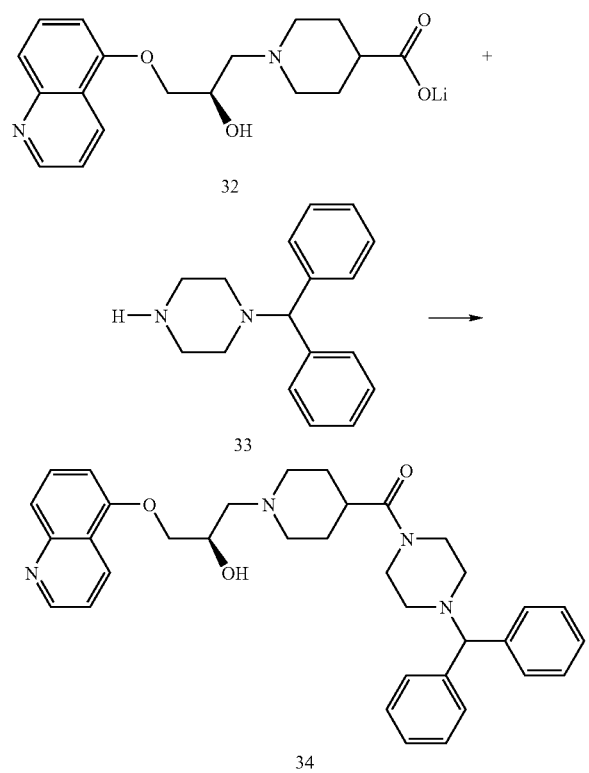

Lithium (R)-1-[2-hydroxy-3-(quinolin-5-yloxy)-propyl]-piperidine-4-carboxylate (32) (100 mg; 0.297 mmol) is dissolved in methylene chloride (3 mL) at ambient temperature. 1-(Diphenylmethyl)piperazine (33) (80 mg; 0.312 mmol), N,N-diisopropylethylamine (0.85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography with gradient elution (90% ethyl acetate in hexanes, then 50%→100% acetone in hexanes) affording the desired product (34) as a solid. CIMS (NH$_3$CI): 565 (MH$^+$)

Example 33

Preparation of (R)-1-[2-hydroxy-3-(quinolin-5-yloxy)-propyl]-piperidine-4-carboxylic acid 4-[1-(o-tolyl)-piperazine] amide (36)

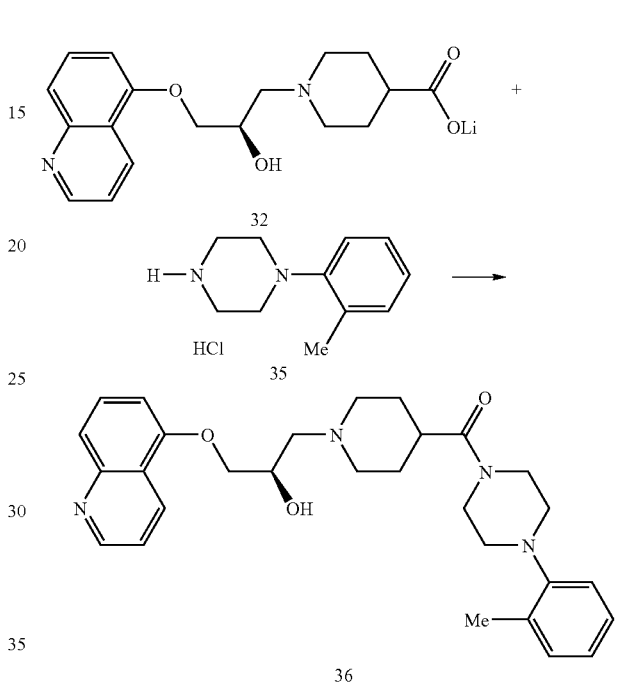

Lithium (R)-1-[2-hydroxy-3-(quinolin-5-yloxy)-propyl]-piperidine-4-carboxylate (32) (100 mg; 0.297 mmol) is dissolved in methylene chloride (3 mL) at ambient temperature. 1-(o-Tolyl)piperazine hydrochloride (35) (66 mg; 0.312 mmol), N,N-diisopropylethylamine (123 mg; 0.952 mmol) and PyBOP (186 mg; 0.357 mmol) are added sequentially. The reaction is stirred for 18 hr. at room temperature, then concentrated under reduced pressure. The residue is purified via silica gel chromatography with gradient elution (90% ethyl acetate in hexanes, then 50%→100% acetone in hexanes) affording the desired product (36) as an oil. CIMS (NH$_3$CI): 489 (MH$^+$)

Example 34

Preparation of (R)-1-[2-hydroxy-3-(quinolin-5-yloxy)-propyl]-piperidine-4-carboxylic acid 1-[4-(phenyl)-butyl]amide (38)

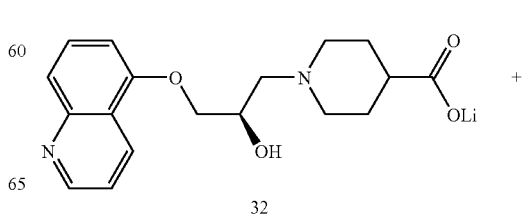

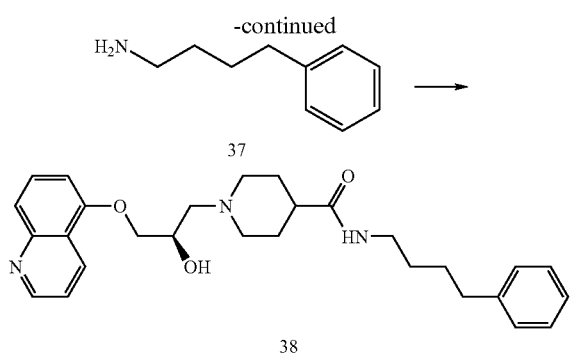

Lithium (R)-1-[2-hydroxy-3-(quinolin-5-yloxy)-propyl]-piperidine-4-carboxylate (32) (100 mg; 0.297 mmol) is dissolved in methylene chloride (3 mL) at ambient temperature. 4-Phenylbutylamine (37) (47 mg; 0.312 mmol), N,N-diisopropylethylamine (85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography with gradient elution (90% ethyl acetate in hexanes, then 50%→100% acetone in hexanes) affording the desired product (38) as a solid. CIMS (NH₃Cl): 462 (MH⁺)

Example 35

Preparation of (R)-1-[2-hydroxy-3-(quinolin-5-yloxy)-propyl]-piperidine-4-carboxylic acid benzyl amide (40)

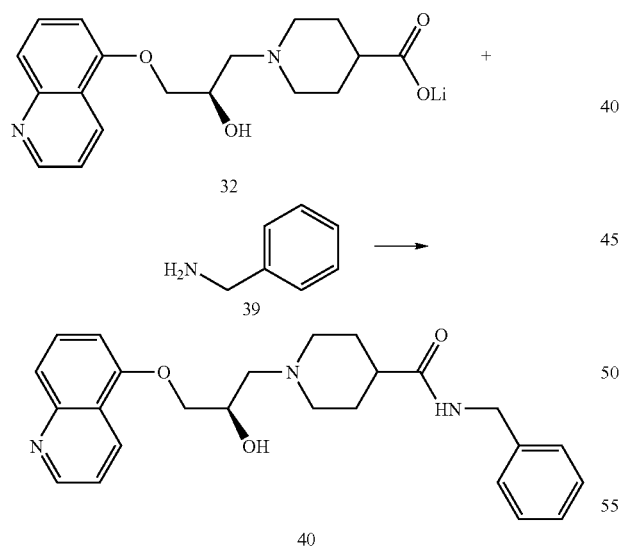

Lithium (R)-1-[2-hydroxy-3-(quinolin-5-yloxy)-propyl]-piperidine-4-carboxylate (32) (100 mg; 0.297 mmol) is dissolved in methylene chloride (3 mL) at ambient temperature. Benzylamine (39) (33 mg; 0.312 mmol), N,N-diisopropylethylamine (85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography with gradient elution (90% ethyl acetate in hexanes, then 50%→100% acetone in hexanes) affording the desired product (40) as an oil. CIMS (NH₃Cl): 420 (MH⁺)

Example 36

Preparation of (R)-1-[2-hydroxy-3-(quinolin-5-yloxy)-propyl]-piperidine-4-carboxylic acid dibenzyl amide (42)

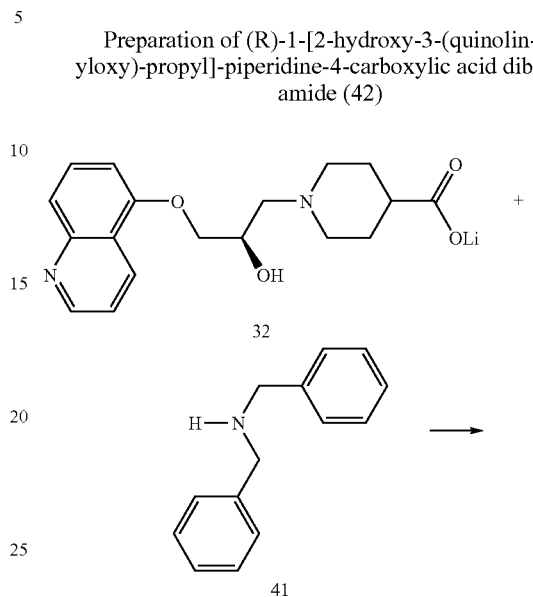

Lithium (R)-1-[2-hydroxy-3-(quinolin-5-yloxy)-propyl]-piperidine-4-carboxylate (32) (100 mg; 0.297 mmol) is dissolved in methylene chloride (3 mL) at ambient temperature. Dibenzylamine (41) (62 mg; 0.312 mmol), N,N-diisopropylethylamine (85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography with gradient elution (90% ethyl acetate in hexanes, then 50%→100% acetone in hexanes) affording the desired product (42) as a solid. CIMS (NH₃Cl): 510 (MH⁺)

Example 37

Preparation of (R)-1-[2-hydroxy-3-(quinolin-5-yloxy)-propyl]-piperidine-3-carboxylic acid ethyl ester (44)

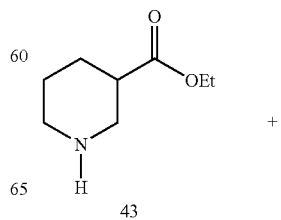

-continued

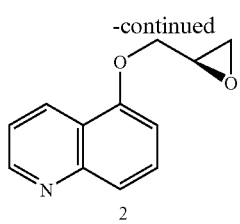

Example 39

Preparation of (R)-1-[2-hydroxy-3-(quinolin-5-yloxy)-propyl]-piperidine-3-carboxylic acid 4-[1-(diphenylmethyl)-piperazine] amide (46)

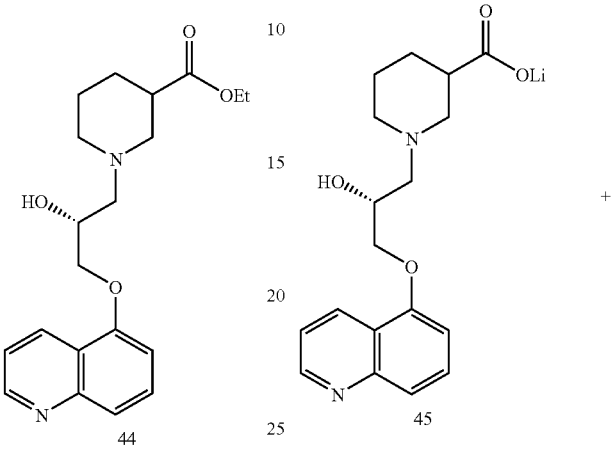

Piperidine-3-carboxylic acid ethyl ester (43) (1.0 g; 6.36 mmol) and (R)-5-oxiranylmethoxy-quinoline (2) (1.28 g; 6.36 mmol) are combined in 10 mL of absolute ethanol. The mixture is heated at reflux for 16 hours. After cooling to ambient temperature, the solution is concentrated in vacuo at 40° C. The residue is chromatographed on silica gel (1:1 acetone:hexanes) affording the desired product (44) as an oil. ESMS: MH⁺ 359

Example 38

Preparation of lithium (R)-1-[2-hydroxy-3-(quinolin-5-yloxy)-propyl]-piperidine-3-carboxylate (45)

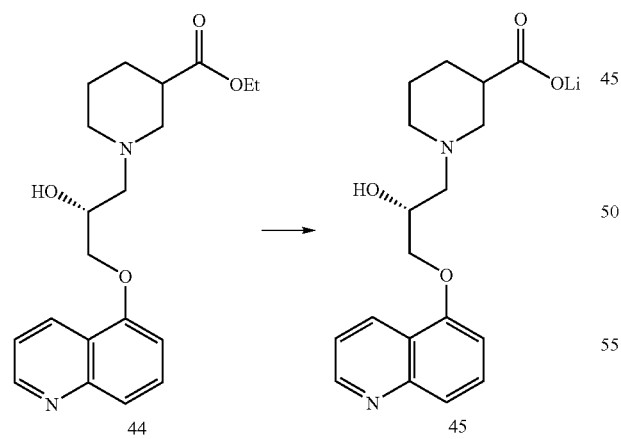

(R)-1-[2-Hydroxy-3-(quinolin-5-yloxy)-propyl]-piperidine-3-carboxylic acid ethyl ester (44) (0.739 g; 2.06 mmol) is dissolved in 20 mL of a 2:2:1 mixture of tetrahydrofuran:water:methanol. Lithium hydroxide (52 mg; 2.17 mmol) is added and the mixture stirred at ambient temperature. After 16 hours, the mixture is concentrated in vacuo at 40° C. Further drying on the vacuum pump affords the desired product (45) as a white solid.

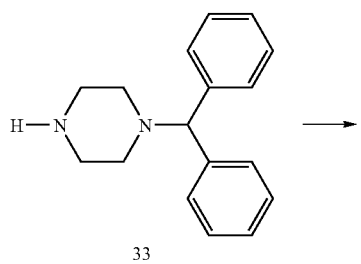

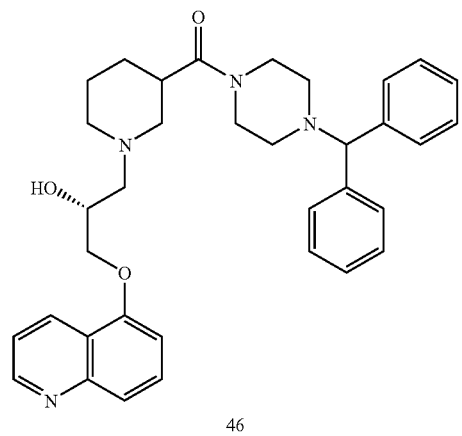

Lithium (R)-1-[2-hydroxy-3-(quinolin-5-yloxy)-propyl]-piperidine-3-carboxylate (45) (100 mg; 0.297 mmol) is dissolved in methylene chloride (2 mL) at ambient temperature. 1-(Diphenylmethyl)piperazine (33) (80 mg; 0.312 mmol), N,N-diisopropylethylamine (0.85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography (1:1 acetone:hexanes) affording the desired product (46) as a solid. ESMS: MH⁺ 565

Example 40

Preparation of (R)-1-[2-hydroxy-3-(quinolin-5-yloxy)-propyl]-piperidine-3-carboxylic acid 4-[1-(o-tolyl)-piperazine] amide (47)

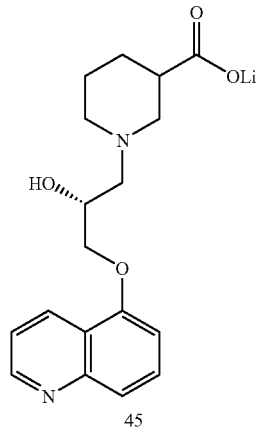

45

+

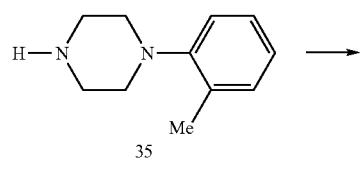

35

→

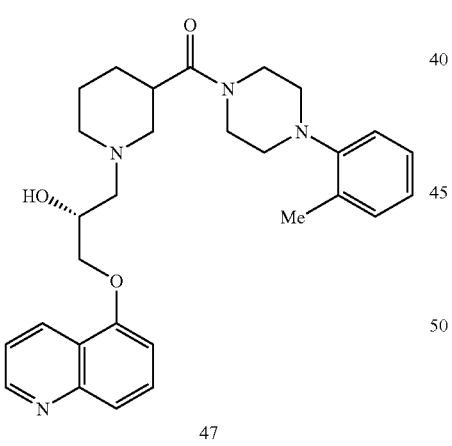

47

Lithium (R)-1-[2-hydroxy-3-(quinolin-5-yloxy)-propyl]-piperidine-3-carboxylate (45) (100 mg; 0.297 mmol) is dissolved in methylene chloride (2 mL) at ambient temperature. 1-(o-Tolyl)piperazine hydrochloride (35) (66 mg; 0.312 mmol), N,N-diisopropylethylamine (123 mg; 0.952 mmol) and PyBOP (186 mg; 0.357 mmol) are added sequentially. The reaction is stirred for 18 hr. at room temperature, then concentrated under reduced pressure. The residue is purified via silica gel chromatography (1:1 acetone:hexanes) affording the desired product (47) as an oil.

ESMS: MH$^+$ 489

Example 41

Preparation of (R)-1-[2-hydroxy-3-(quinolin-5-yloxy)-propyl]-piperidine-3-carboxylic acid 1-[4-(phenyl)-butyl]amide (48)

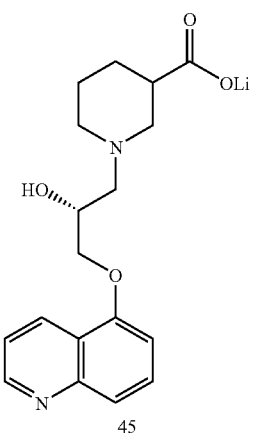

45

+

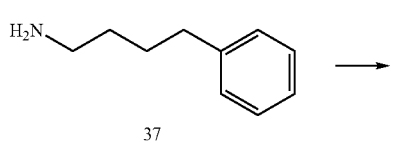

37

→

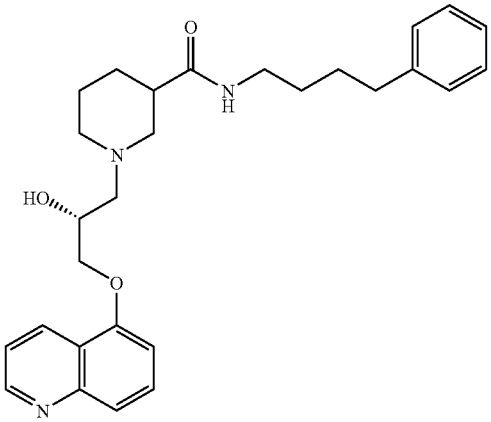

48

Lithium (R)-1-[2-hydroxy-3-(quinolin-5-yloxy)-propyl]-piperidine-3-carboxylate (45) (100 mg; 0.297 mmol) is dissolved in methylene chloride (2 mL) at ambient temperature. 4-Phenylbutylamine (37) (47 mg; 0.312 mmol), N,N-diisopropylethylamine (85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography (1:1 acetone:hexanes) affording the desired product (48) as an oil. ESMS: MH$^+$ 462

Example 42

Preparation of (R)-1-[2-hydroxy-3-(quinolin-5-yloxy)-propyl]-piperidine-3-carboxylic acid 1-[3,3-(diphenyl)-propyl]amide (50)

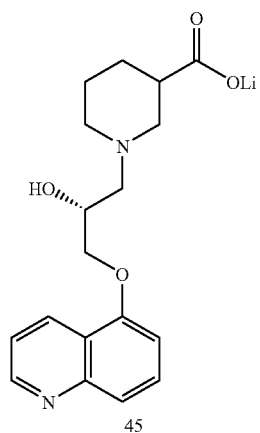

45

+

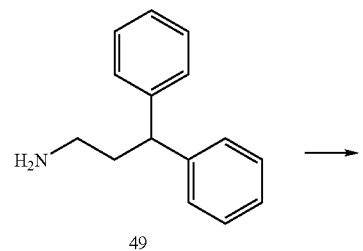

49

→

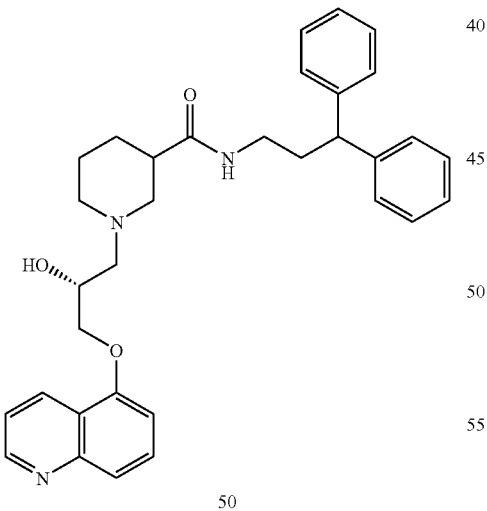

50

Lithium (R)-1-[2-hydroxy-3-(quinolin-5-yloxy)-propyl]-piperidine-3-carboxylate (45) (100 mg; 0.297 mmol) is dissolved in methylene chloride (2 mL) at ambient temperature. 3,3-Diphenylpropylamine (49) (66 mg; 0.312 mmol), N,N-diisopropylethylamine (85 mg; 0.654 mmol) and PyBOP (186 mg; 0.357 mmol) are added sequentially. The reaction is stirred for 18 hr. at room temperature, then concentrated under reduced pressure. The residue is purified via silica gel chromatography (1:1 acetone:hexanes) affording the desired product (50) as a solid. ESMS: MH$^+$ 524

Example 43

Preparation of 1-tert-butoxycarbonyl-4-aminomethylpiperidine (51)

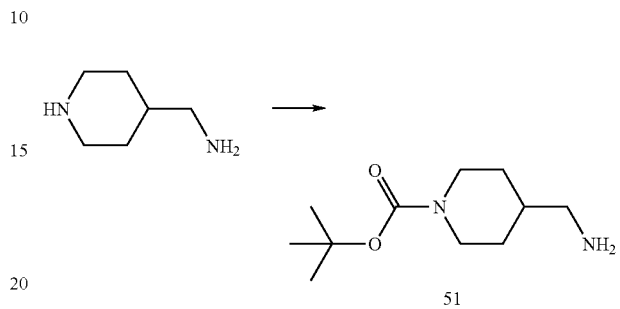

51

4-Aminomethylpiperidine (2.28 g; 20 mmol) is dissolved in dry toluene (25 mL) at ambient temperature. Benzaldehyde (2.03 mL; 20 mmol) is added in one portion and the solution is heated to azeotropic reflux for 135 minutes (with concomitant removal of water from the reaction medium). The reaction mixture is cooled to ambient temperature then di-tert-butyl dicarbonate (4.8 g; 22 mmol) is added portionwise and the resulting solution is stirred at ambient temperature for 64 hours. The solution is concentrated to dryness in vacuo at 40° C., then 1N KHSO$_4$ (22 mL) is added to the residue and the resulting mixture is stirred rapidly at ambient temperature for 4 hours. The mixture is extracted with ether (3×20 mL), then the aqueous layer is basicified with 1N NaOH (30 mL). Solid NaCl is added to the alkaline aqueous layer, then it is extracted with dichloromethane (3×30 mL). The organic extracts are dried (MgSO$_4$), filtered, and concentrated in vacuo affording the title compound (3.34 g) as a light colored liquid. ESMS: MH$^+$ 215.4

Example 44

Preparation of 5-phenyl-2-(3-phenyl-propyl)-pentanoic acid (1-tert-butoxycarbonyl-aminomethylpiperidin-yl)-amide (52)

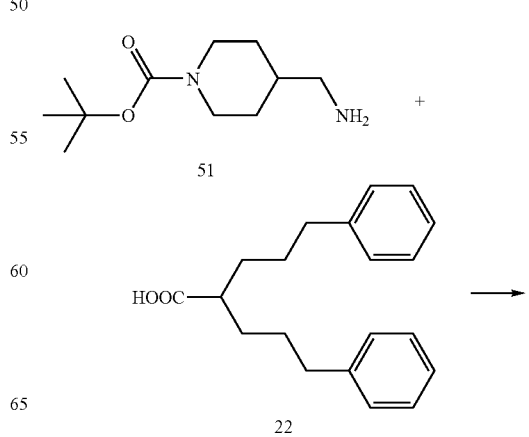

22

→

-continued

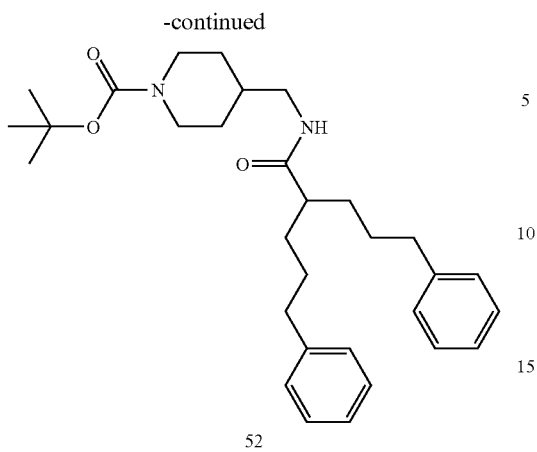

52

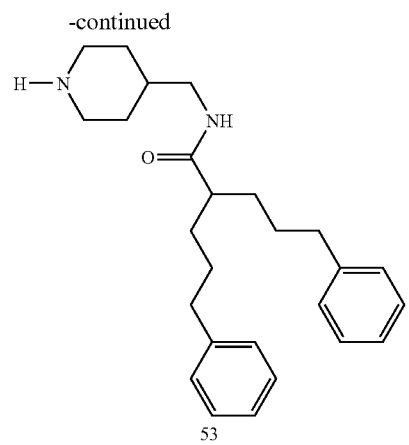

53

5-Phenyl-2-(3-phenyl-propyl)-pentanoic acid (1-tert-butoxycarbonyl-aminomethylpiperidin-yl)-amide (52) (0.67 g; 1.36 mmol) is dissolved in methylene chloride (25 mL) at ambient temperature. Trifluoroacetic acid (25 mL) is added in a slow stream, and the solution is stirred for 90 minutes at ambient temperature. The solution is concentrated in vacuo at 40° C. The residue is slurried in a mixture of methylene chloride (10 mL) and water (100 mL), then potassium carbonate is added until the slurry is alkaline. The slurry is diluted with water (200 mL) then extracted with methylene chloride (3×100 mL). The organic extracts are dried over MgSO$_4$, filtered, and concentrated in vacuo affording the desired product (0.46 g) as a white solid.

1-Butoxycarbonyl-4-aminomethylpiperidine (51) (0.30 g; 1.4 mmol) is dissolved in DMF (10 mL) at ambient temperature. 5-Phenyl-2-(3-phenyl-propyl)-pentanoic acid (22) (0.415 g: 1.4 mmol) is added followed sequentially by 1-hydroxybenzotriazole (0.2364 g; 1.75 mmol), triethylamine (0.2439 mL; 1.75 mmol), and N-(3-dimethylaminopropyl)-N'-ethylcarbodiimide hydrochloride (0.2952 g; 1.54 mmol). The mixture is stirred at ambient temperature for 18 hours then poured onto ethyl acetate (300 mL) and extracted sequentially with water (100 mL), 1N HCl (50 mL), saturated NaHCO$_3$ (50 mL), and brine (50 mL). The organic layer is dried (MgSO$_4$), filtered, and concentrated in vacuo. The residue is purified via silica gel chromatography with gradient elution (10%→50% ethyl acetate in hexanes) affording the desired compound (0.67 g) as a colorless oil. ESMS: MH$^+$ 493.4

Example 45

Preparation of 5-phenyl-2-(3-phenyl-propyl)-pentanoic acid aminomethyl-piperidin-4-ylamide (53)

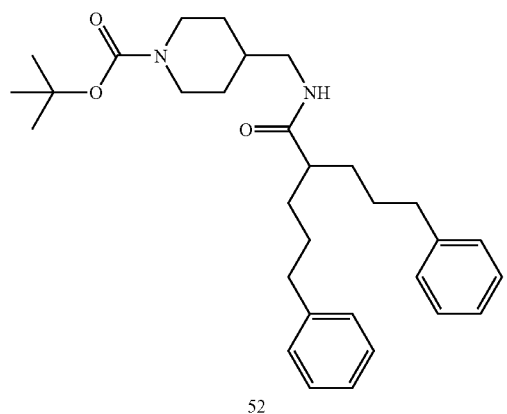

52

Example 46

Preparation of 5-phenyl-2-(3-phenyl-propyl)-pentanoic acid {1-[2-hydroxy-3-quinolin-5-yloxy)-propyl]-aminomethyl-piperidin-4-ylamide (54)

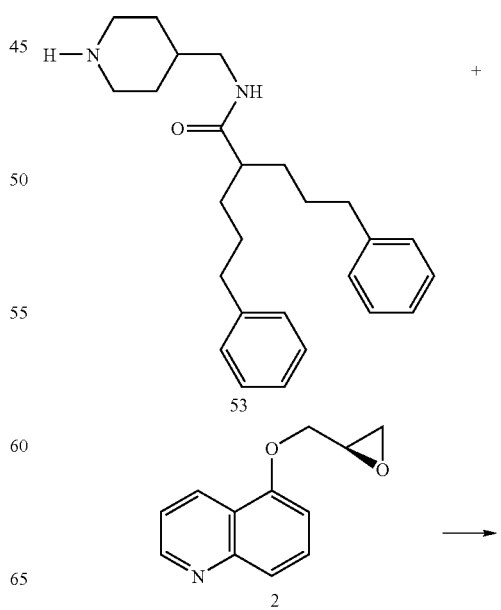

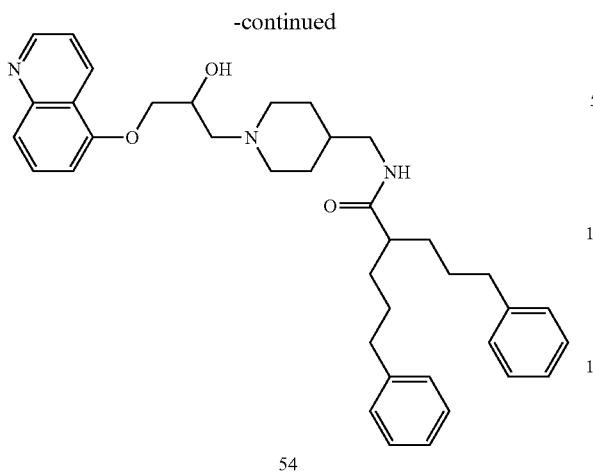

54

5-Phenyl-2-(3-phenyl-propyl)-pentanoic acid aminomethyl-piperidin-4-ylamide (53) (147.5 mg; 0.376 mmol) is dissolved in isopropanol (10 mL) at ambient temperature. (R)-5-Oxiranylmethoxy-quinoline (2) (76.2 mg; 0.376 mmol) is added, then the mixture is heated to 70° C. and maintained for 18 hours. After cooling to ambient temperature, the solution is concentrated in vacuo at 40° C. The residue is purified via silica gel chromatography with gradient elution (0%→20% methanol in methlene chloride) affording the desired product (176.2 mg) as a light colored solid. ESMS: MH+ 594.4 (base).

Example 47

Preparation of 1-tert-butoxycarbonyl-4-carboxymethylpiperidine (55)

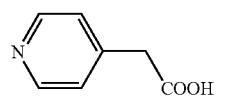

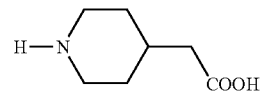

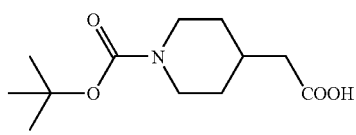

55

4-Pyridylacetic acid hydrochloride (2.5 g; 14.4 mmol) is dissolved in deionized water (30 mL) in a hydrogenation flask. $PtO_2$ (0.2 g) is added and the mixture is hydrogenated at 50 psi for 18 hours at ambient temperature. The solids are separated by decantation, and the aqueous solution is basicified with $Na_2CO_3$ (3 g). Dioxane (10 mL) is added and the mixture is stirred rapidly at ambient temperature. A solution of di-tert-butyl dicarbonate (9.44 g; 43.3 mmol) in dioxane (20 mL) is added dropwise. The resulting mixture is stirred for 18 hours then concentrated in vacuo at 40° C. The resulting aqueous solution is poured onto a solution of water (300 mL) and saturated aqueous $NaHCO_3$ (10 mL), then the mixture is extracted with ethyl acetate (3×50 mL). The aqueous layer is acidified with citric acid then extracted with ethyl acetate (3×100 mL), dried ($MgSO_4$), filtered, and concentrated in vacuo affording the desired product (3.60 g) as a solid. ESMS: MH+ 244.4

Example 48

Preparation of 4-[4-phenyl-1-(3-phenyl-propyl)-butylcarbamoyl]-methylpiperidine-1-carboxylic acid tert-butyl ester (56)

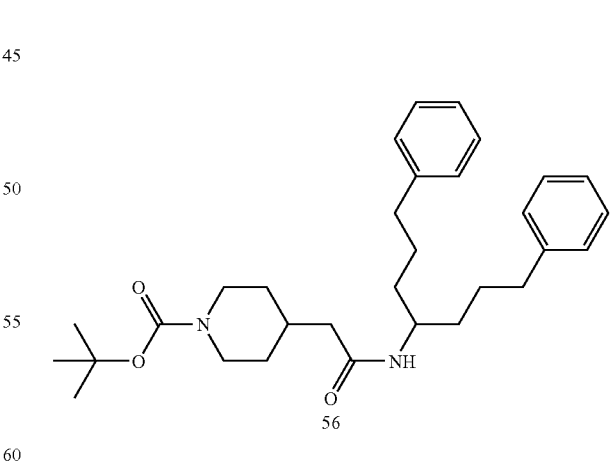

56

4-[4-Phenyl-1-(3-phenyl-propyl)-butylcarbamoyl]-methylpiperidine-1-carboxylic acid tert-butyl ester (55) (1 g; 4.11 mmol) is dissolved in DMF (30 mL) at ambient temperature. 1,7-Diphenyl-4-aminoheptane hydrochloride (1) (1.25 g; 4.11 mmol), 1-Hydroxybenzotriazole (0.694 g; 5.14 mmol), triethylamine (0.716; 5.14 mmol), and N-(3-dimethylaminopropyl)-N'-ethylcarbodiimide hydrochloride (0.87 g; 4.54 mmol) are added sequentially. The mixture is stirred for 18 hours at ambient temperature then poured onto ethyl acetate (300 mL) and extracted sequentially with water (100 mL), 1N HCl (50 mL), saturated NaHCO₃ (50 mL), and brine (50 mL). The organic layer is dried (MgSO₄), filtered, and concentrated in vacuo. The residue is purified via silica gel chromatography with gradient elution (10%→50% ethyl acetate in hexanes) affording the desired compound (1.62 g) as a colorless oil. ESMS: MH⁺ 493.6

Example 49

Preparation of methylpiperidine-4-carboxylic acid [4-phenyl-1-(3-phenyl-propyl)-butyl]-amide (57)

4-[4-Phenyl-1-(3-phenyl-propyl)-butylcarbamoyl]-methylpiperidine-1-carboxylic acid tert-butyl ester (56) (1.62 g; 3.29 mmol) is dissolved in methylene chloride (50 mL) at ambient temperature. Trifluoroacetic acid (50 mL) is added in a slow stream, and the solution is stirred for 90 minutes at ambient temperature. The solution is concentrated in vacuo at 40° C. The residue is slurried in a mixture of methylene chloride (30 mL) and water (200 mL), then potassium carbonate is added until the slurry is alkaline. The slurry is diluted with water (200 mL) then extracted with methylene chloride (3×100 mL). The organic extracts are dried over MgSO₄, filtered, and concentrated in vacuo affording the desired product (1.23 g) as a white solid.

Example 50

Preparation of (R)-1-[2-hydroxy-3-(quinolin-5-yloxy)-propyl]-methylpiperidine-4-carboxylic acid [4-phenyl-1-(3-phenyl-propyl)-butyl]-amide (58)

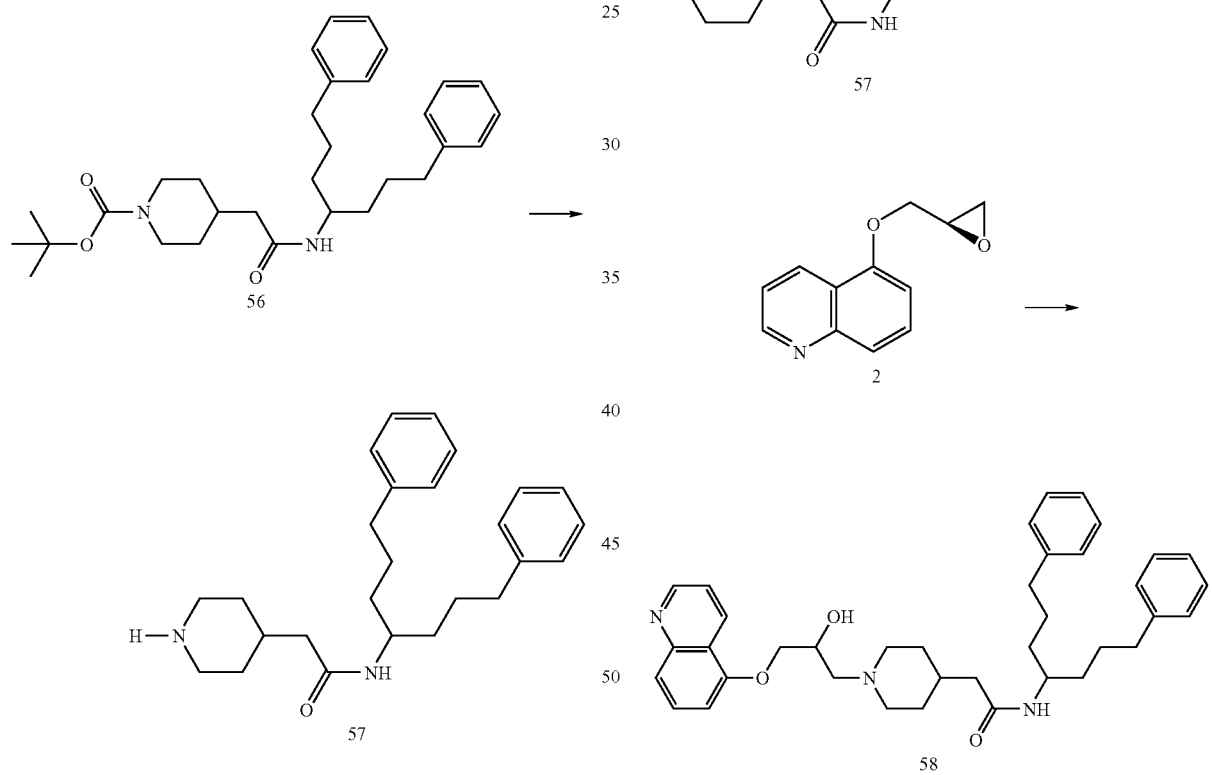

Methylpiperidine-4-carboxylic acid [4-phenyl-1-(3-phenyl-propyl)-butyl]-amide (57) (150 mg; 0.382 mmol) is dissolved in isopropanol (10 mL) at ambient temperature. (R)-5-Oxiranylmethoxy-quinoline (2) (77.5 mg; 0.382 mmol) is added, then the mixture is heated to 70° C. and maintained for 18 hours. After cooling to ambient temperature, the solution is concentrated in vacuo at 40° C. The residue is purified via silica gel chromatography with gradient elution (0%→25% methanol in methylene chloride) affording the desired product (187.4 mg) as a solid foam. ESMS: MH⁺ 594.4 (base).

Example 51

Preparation of 4-[4-(3-pyridyl)-1-(3-pyridyl-propyl)-butylcarbamoyl]-piperidine-1-carboxylic acid tert-butyl ester (59)

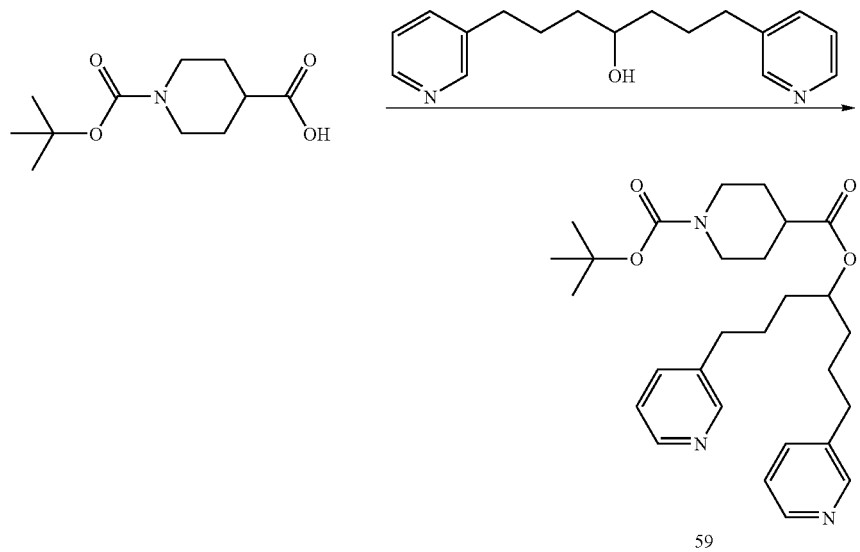

1-tert-Butoxycarbonyl-piperidine-4-carboxylic acid (0.5 g; 2.18 mmol) is dissolved in DMF (10 mL) at ambient temperature. 1-Hydroxybenzotriazole (0.37, 2.74 mmol), triethylamine (0.46 mL, 3.3 mmol), 1,7-di-(3-pyridyl)-heptan-4-ol (0.59 g; 2.4 mmol) as prepared according to WO 98/20893 A1 assigned to Vertex Pharmaceuticals, and N-(3-dimethylamino-propyl)-N'-ethylcarbodiimide hydrochloride (0.46 g; 2.4 mmol) are added sequentially. The mixture is stirred at ambient temperature for 18 hours. The mixture is then poured onto ethyl acetate (150 mL) and washed successively with water (50 mL), saturated aqueous sodium bicarbonate (10 mL), and brine (30 mL). The organic layer is dried over MgSO$_4$, filtered, and concentrated in vacuo. The residue is purified via silica gel chromatography with gradient elution (0%→25% methanol in methylene chloride) affording the desired product (0.3754 g) as a yellow solid. ESMS: MH$^+$ 482.4.

Example 52

Preparation of piperidine-4-carboxylic acid [4-(3pyridyl)-1-(3-pyridyl-propyl)-butyl]-amide (60)

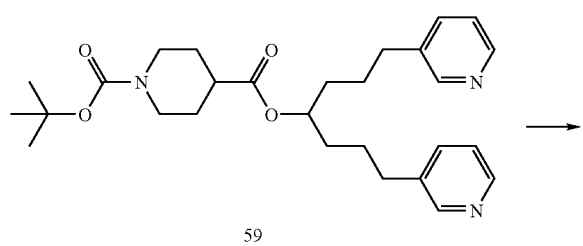

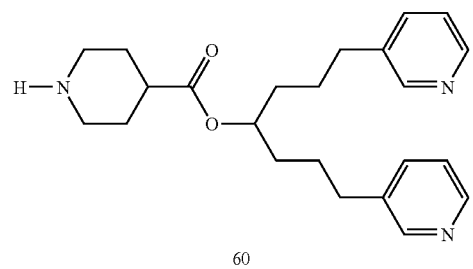

4-[4-(3-Pyridyl)-1-(3-pyridyl-propyl)-butylcarbamoyl]-piperidine-1-carboxylic acid tert-butyl ester (59) (0.3754 g; 0.78 mmol) is dissolved in methylene chloride (6 mL) at ambient temperature. Trifluoroacetic acid (6 mL) is added in a slow stream, and the solution is stirred for 90 minutes at ambient temperature. The solution is concentrated in vacuo at 40° C. The residue is slurried in a mixture of methylene chloride (10 mL) and water (50 mL), then potassium carbonate is added until the slurry is alkaline. The slurry is diluted with water (50 mL) then extracted with methylene chloride (3×10 mL). The organic extracts are dried over MgSO$_4$, filtered, and concentrated in vacuo affording the desired product (0.1704 g) as a yellow oil. ESMS: MH$^+$ 382.4 (base).

Example 53

Preparation of (R)-1-[2-hydroxy-3-(quinolin-5-yloxy)-propyl]-piperidine-4-carboxylic acid [4-(3-pyridyl-1-(3-pyridyl-propyl)-butyl]-amide (61)

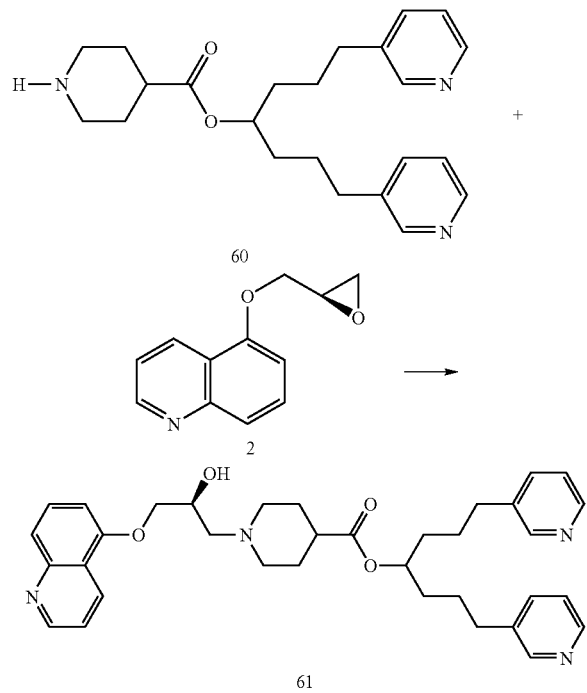

Piperidine-4-carboxylic acid [4-(3-pyridyl)-1-(3-pyridyl-propyl)-butyl]-amide (60) (170.4 mg; 0.45 mmol) is dissolved in isopropanol (10 mL) at ambient temperature. (R)-5-Oxiranylmethoxy-quinoline (2) (90.0 mg; 0.45 mmol) is added, then the mixture is heated to 70° C. and maintained for 18 hours. After cooling to ambient temperature, the solution is concentrated in vacuo at 40° C. The residue is purified via silica gel chromatography with gradient elution (0%→50% methanol in methylene chloride) affording the desired product (120.2 mg) as an amber oil. ESMS: MH+ 583.4.

Example 54

Preparation of 1-[(N-tert-butoxycarbonyl)-(N-methyl)-2-aminoacetyl]-piperidine-4-carboxylic acid [4-phenyl-1-(3-phenyl-propyl)-butyl]-amide (62)

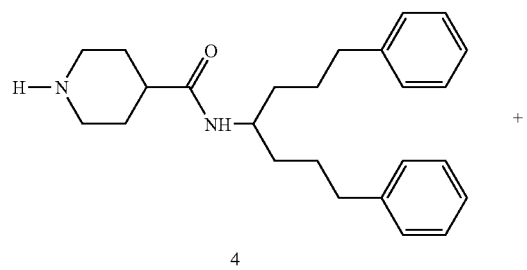

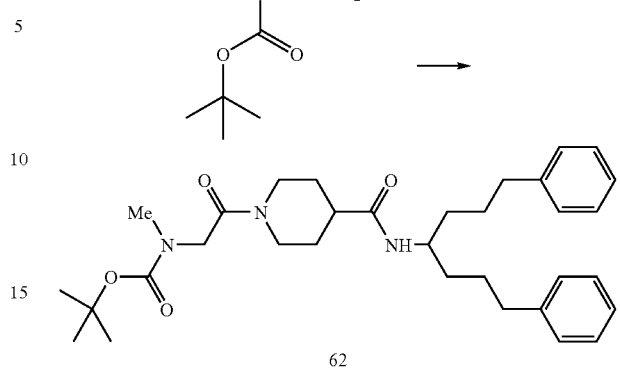

Piperidine-4-carboxylic acid [4-phenyl-1-(3-phenyl-propyl)-butyl]-amide (4) (1.00 g; 2.64 mmol) is dissolved in methylene chloride (25 mL) at ambient temperature. (N-tert-butoxycarbonyl)-(N-methyl)-2-aminoacetic acid (0.60 g; 3.17 mmol), N,N-diisopropylethylamine (0.75 g; 5.81 mmol) and PYBOP (1.65 g; 3.17 mmol) are added sequentially. The reaction is stirred for 18 hours at room temperature, then concentrated under reduced pressure. The residue is purified via silica gel chromatography (60%→90% ethyl acetate in hexanes) affording the desired product (62) as a solid. ESMS: MH+ 550

Example 55

Preparation of 1-[(N-methyl)-2-aminoacetyl]-piperidine-4-carboxylic acid [4-phenyl-1-(3-phenyl-propyl)-butyl]-amide (63)

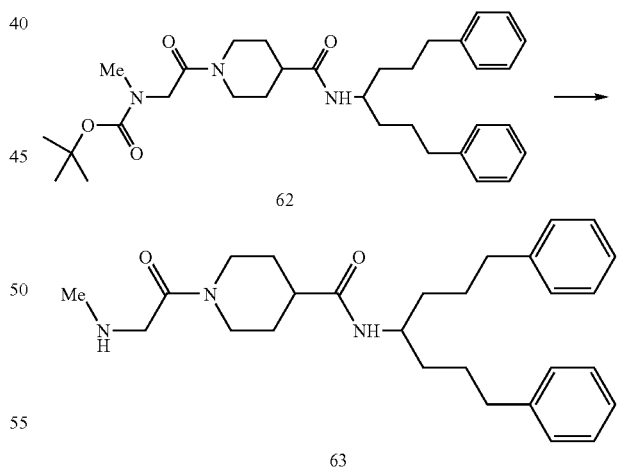

1-[(N-tert-butoxycarbonyl)-(N-methyl)-2-aminoacetyl]-piperidine-4-carboxylic acid [4-phenyl-1-(3-phenyl-propyl)-butyl]-amide (62) (1.60 g; 2.91 mmol) is dissolved in methylene chloride (30 mL) at ambient temperature. Trifluoroacetic acid (15 mL) is added in a slow stream, and the solution is stirred for 4 hours at ambient temperature. The solution is concentrated in vacuo at 40° C. The residue is dissolved in methylene chloride (200 mL) and poured onto saturated sodium bicarbonate solution. The pH is adjusted to

Example 56

Preparation of 1-{N-[2-(R)-hydroxy-3-(quinolin-5-yloxy)-propyl]-(N-methyl)-2-aminoacetyl}-piperidine-4-carboxylic acid [4-phenyl-1-(3-phenyl-propyl)-butyl]-amide (64)

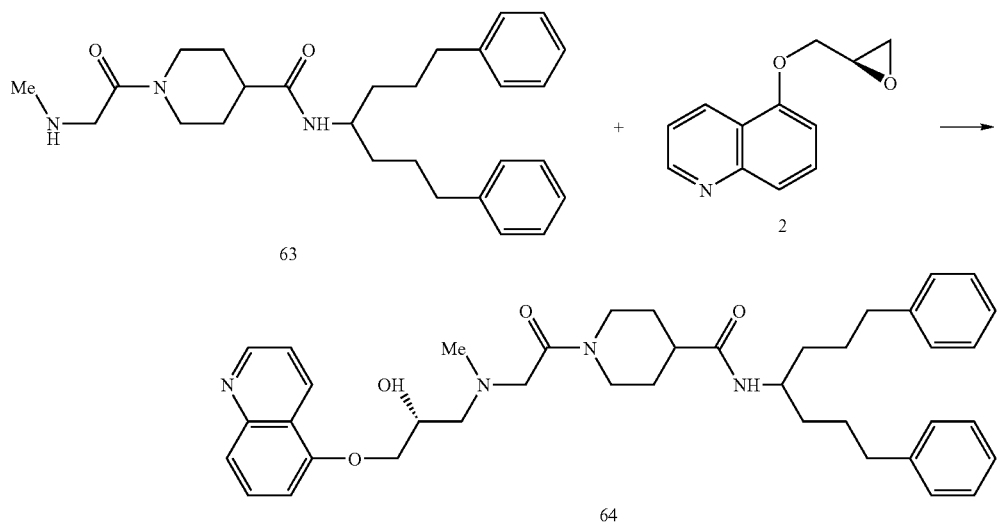

1-[(N-methyl)-2-aminoacetyl]-piperidine-4-carboxylic acid [4-phenyl-1-(3-phenyl-propyl)-butyl]-amide (63) (223.5 mg; 0.497 mmol]) is dissolved in ethanol (10 mL) at ambient temperature. (R)-5-Oxiranylmethoxy-quinoline (2) (100.0 mg; 0.497 mmol) is added, then the mixture is refluxed for 17.5 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (110 mg) as a white solid. ESMS: MH⁺ 651.6.

Example 57

Preparation of N-tert-butoxycarbonyl-N-methyl-2-aminoacetic acid [4-phenyl-1-(3-phenyl-propyl)-butyl]-amide (65)

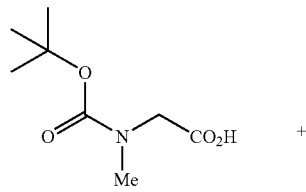

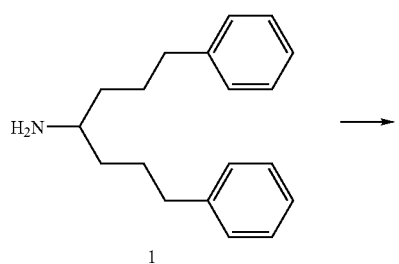

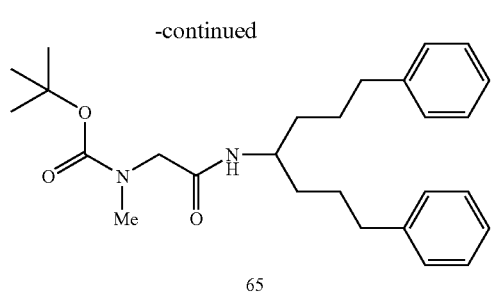

(N-tert-butoxycarbonyl)-(N-methyl)-2-aminoacetic acid (1.00 g; 5.29 mmol) is dissolved in methylene chloride (40 mL) at ambient temperature. 1,7-Diphenyl-4-aminoheptane hydrochloride (1) (1.93 g; 6.34 mmol), N,N-diisopropylethylamine (2.19 g; 16.9 mmol) and PyBOP (3.30 g; 3.30 mmol) are added sequentially. The reaction is stirred for 1 hour at room temperature, then concentrated under reduced pressure. The residue is purified via silica gel chromatography (20%→40% ethyl acetate in hexanes) affording the desired product (65) as a solid. CIMS: MH⁺ 439

Example 58

Preparation of N-methyl-2-aminoacetic acid [4-phenyl-1-(3-phenyl-propyl)-butyl]-amide (66)

Example 59

Preparation of N-(N-tert-butoxycarbonyl-piperidine-4-carbonyl)-(N-methyl)-2-aminoacetic acid [4-phenyl-1-(3-phenyl-propyl)-butyl]-amide (67)

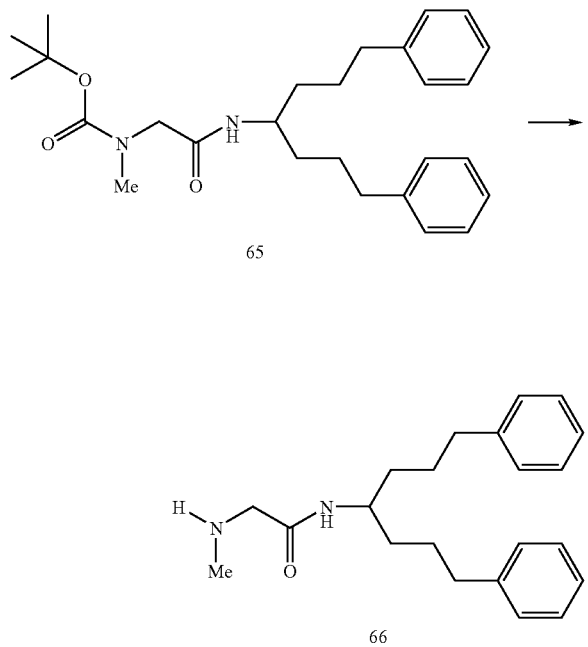

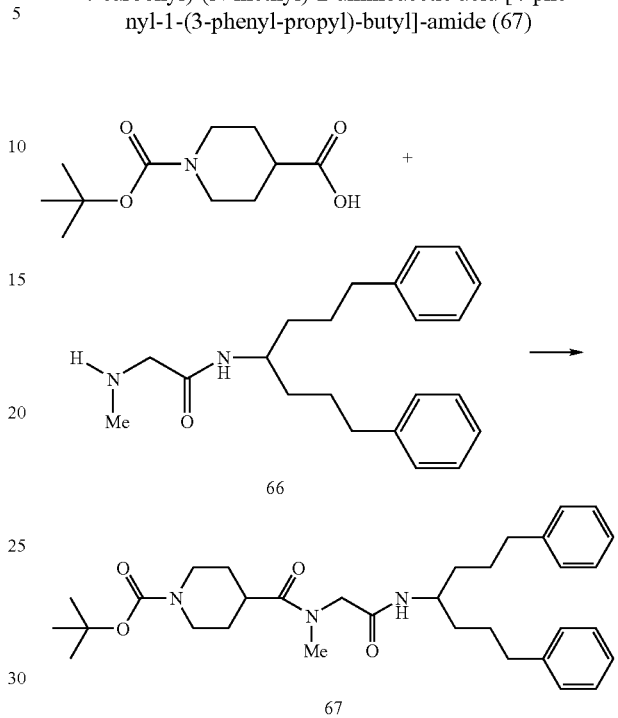

N-tert-Butoxycarbonyl-N-methyl-2-aminoacetic acid [4-phenyl-1-(3-phenyl-propyl)-butyl]-amide (65) (2.19 g; 4.99 mmol) is dissolved in methylene chloride (30 mL) at ambient temperature. Trifluoroacetic acid (20 mL) is added in a slow stream, and the solution is stirred for 2.5 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO$_4$, filtered, and concentrated in vacuo affording the desired product (1.65 g) as a white solid. CIMS: MH$^+$ 339

1-tert-Butoxycarbonyl-piperidine-4-carboxylic acid (0.61 g; 2.66 mmol) is dissolved in methylene chloride (20 mL) at ambient temperature. N-methyl-2-aminoacetic acid [4-phenyl-1-(3-phenyl-propyl)-butyl]-amide (66) (0.75 g; 2.22 mmol), N,N-diisopropylethylamine (0.63 g; 4.87 mmol) and PyBOP (1.38 g; 2.66 mmol) are added sequentially. The reaction is stirred for 14 hours at room temperature, then concentrated under reduced pressure. The residue is purified via silica gel chromatography (60%→80% ethyl acetate in hexanes) affording the desired product (67) as a clear oil. CIMS: MH$^+$ 550

Example 60

Preparation of N-(piperidine-4-carbonyl)-(N-methyl)-2-aminoacetic acid [4-phenyl-1-(3-phenyl-propyl)-butyl]-amide (68)

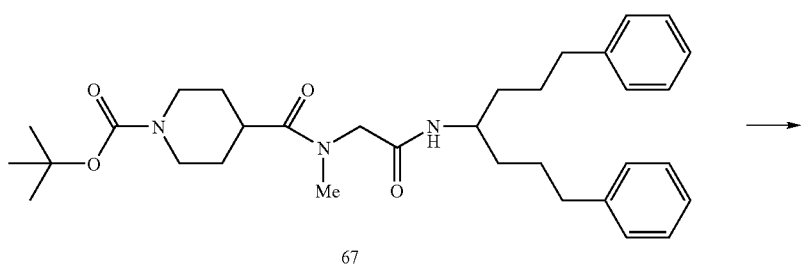

-continued

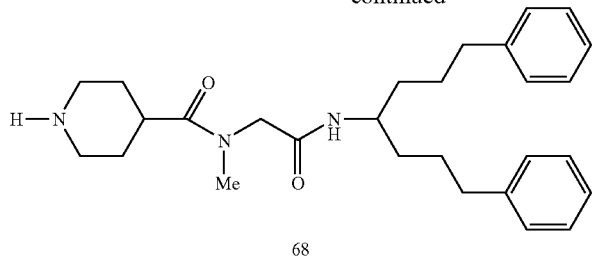
68

N-(N-tert-Butoxycarbonyl-piperidine-4-carbonyl)-(N-methyl)-2-aminoacetic acid [4-phenyl-1-(3-phenyl-propyl)-butyl]-amide (67) (1.46 g; 2.66 mmol) is dissolved in methylene chloride (30 mL) at ambient temperature. Trifluoroacetic acid (15 mL) is added in a slow stream, and the solution is stirred for 2 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO₄, filtered, and concentrated in vacuo affording the desired product (1.65 g) as a clear oil. ESMS: MH⁺ 450.2

Example 61

Preparation of N-{1-[2-(R)-hydroxy-3-(quinolin-5-yloxy)-propyl]-piperidine-4-carbonyl}-(N-methyl)-2-aminoacetic acid [4-phenyl-1-(3-phenyl-propyl)-butyl]-amide (69)

N-(Piperidine-4-carbonyl)-(N-methyl)-2-aminoacetic acid [4-phenyl-1-(3-phenyl-propyl)-butyl]-amide (68) (223.5 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 15.5 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (110 mg) as a white solid. ESMS: MH⁺ 651.6

Example 62

Preparation of 1-(1-tert-butoxycarbonylpiperidine-4-carbonyl)-piperidine-4-carboxylic acid [4-phenyl-1-(3-phenyl-propyl)-butyl]-amide (70)

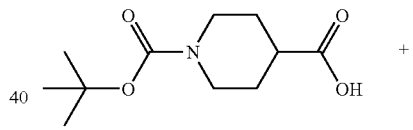

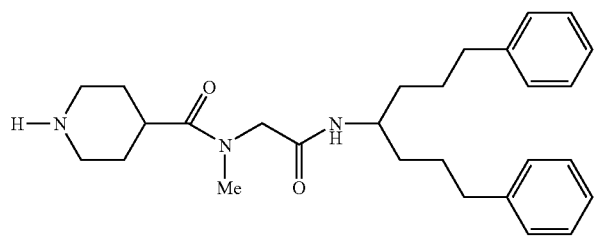
68

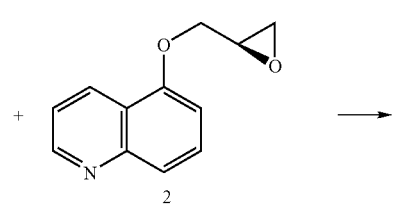
2

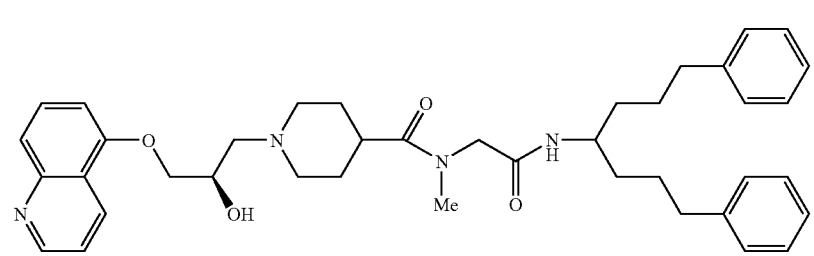
69

-continued

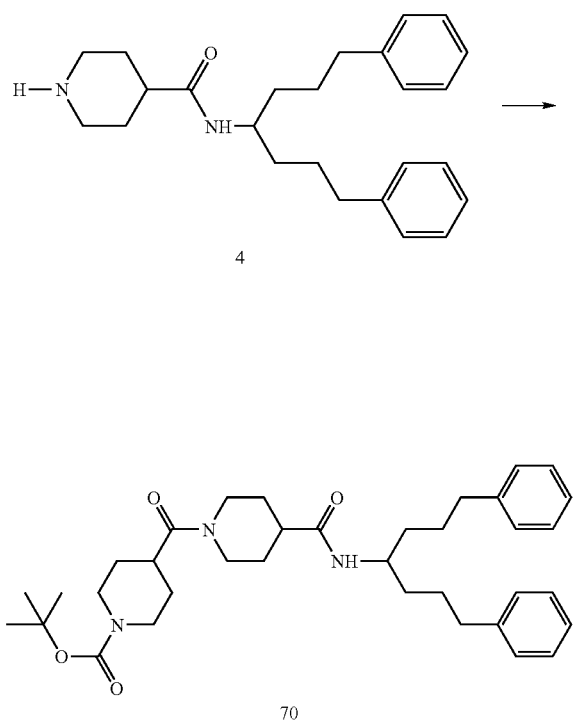

4

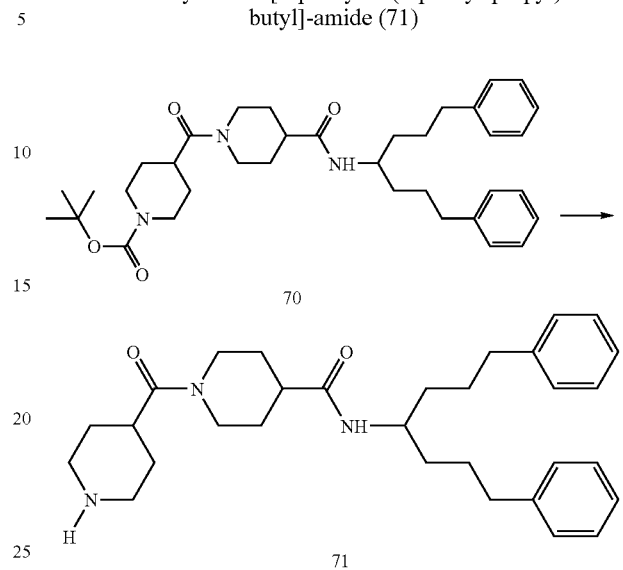

70

Piperidine-4-carboxylic acid [4-phenyl-1-(3-phenyl-propyl)-butyl]-amide (4) (1.00 g; 2.64 mmol) is dissolved in methylene chloride (25 mL) at ambient temperature. 1-tert-Butoxycarbonyl-piperidine-4-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 16 hours at room temperature, then concentrated under reduced pressure. The residue is purified via silica gel chromatography (70%→90% ethyl acetate in hexanes) affording the desired product (70) as a solid. ESMS: MH+ 590.6

Example 63

Preparation of 1-(piperidine-4-carbonyl)-piperidine-4-carboxylic acid [4-phenyl-1-(3-phenyl-propyl)-butyl]-amide (71)

71

1-(1-tert-butoxycarbonylpiperidine-4-carbonyl)-piperidine-4-carboxylic acid [4-phenyl-1-(3-phenyl-propyl)-butyl]-amide (70) (1.84 g; 3.12 mmol) is dissolved in methylene chloride (30 mL) at ambient temperature. Trifluoroacetic acid (15 mL) is added in a slow stream, and the solution is stirred for 1.25 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO₄, filtered, and concentrated in vacuo affording the desired product (1.65 g) as a white solid. ESMS: MH+ 490.4

Example 64

Preparation of N-{1-[2-(R)-hydroxy-3-(quinolin-5-yloxy)-propyl]-piperidine-4-carbonyl}-piperidine-4-carboxylic acid [4-phenyl-1-(3-phenyl-propyl)-butyl]-amide (72)

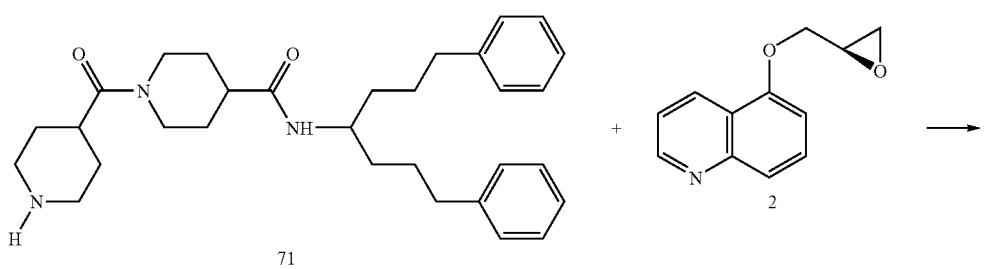

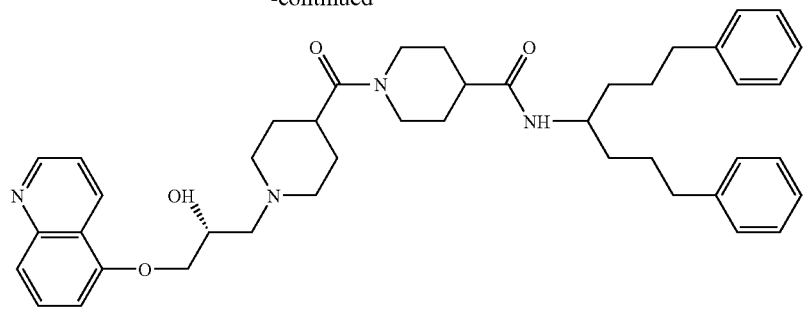

72

1-(Piperidine-4-carbonyl)-piperidine-4-carboxylic acid [4-phenyl-1-(3-phenyl-propyl)-butyl]-amide (71) (243.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 16 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (200 mg) as a white solid. ESMS: MH+ 691.6

Example 65

Preparation of 2-[4-phenyl-1-(3-phenyl-propyl)-butylcarbamoyl]-piperidine-1-carboxylic acid tert-butyl ester (73)

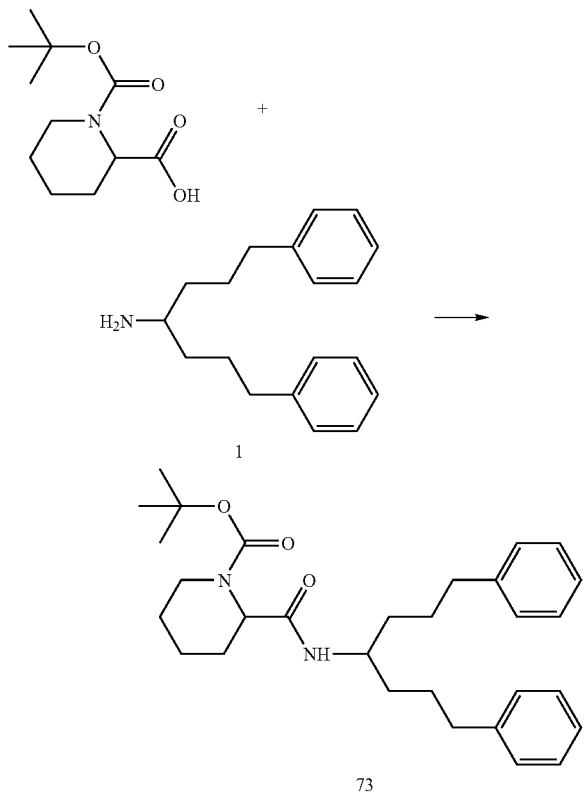

1-tert-Butoxycarbonyl-piperidine-2-carboxylic acid (3 g; 13.1 mmol) is dissolved in methylene chloride (100 mL) at ambient temperature. 1,7-Diphenyl-4-aminoheptane hydrochloride (1) (4.77 g; 15.7 mmol), diisopropylethylamine (7.3 mL; 41.9 mmol), and PyBOP (8.17 g; 15.7 mmol) are added sequentially. The mixture is stirred for 17 hours at ambient temperature then concentrated in vacuo at 40° C. The residue is purified via silica gel chromatography with gradient elution (10%→30% ethyl acetate in hexanes) affording the desired product as an oil. ESMS: MH+ 479.4

Example 66

Preparation of 2-[4-phenyl-1-(3-phenyl-propyl)-butylcarbamoyl]-piperidine (74)

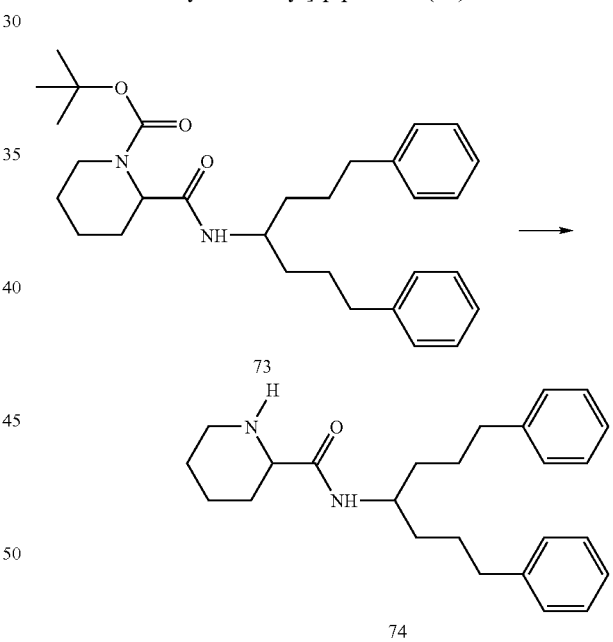

2-[4-Phenyl-1-(3-phenyl-propyl)-butylcarbamoyl]-piperidine-1-carboxylic acid tert-butyl ester (73) (6.77 g; 14.1 mmol) is dissolved in methylene chloride (60 mL) at ambient temperature. Trifluoroacetic acid (40 mL) is added in a slow stream, and the solution is stirred for 1.25 hours at ambient temperature. The solution is concentrated in vacuo at 40° C. The residue is dissolved in methylene chloride (300 mL) and poured onto saturated sodium bicarbonate solution. The pH is adjusted to 9 with saturated potassium carbonate solution. The mixture is shaken the layers separated. The water layer is extracted with methylene chloride (3×100 mL). The combined organic extracts are washed with water, dried over MgSO4, filtered, and concentrated in vacuo affording the desired product (5.34 g) as a white solid. ESMS: MH+ 379.2

Example 67

Preparation of 1-(1-tert-butoxycarbonylpiperidine-4-carbonyl)-piperidine-2 carboxylic acid [4-phenyl-1-(3-phenyl-propyl)-butyl]-amide (75)

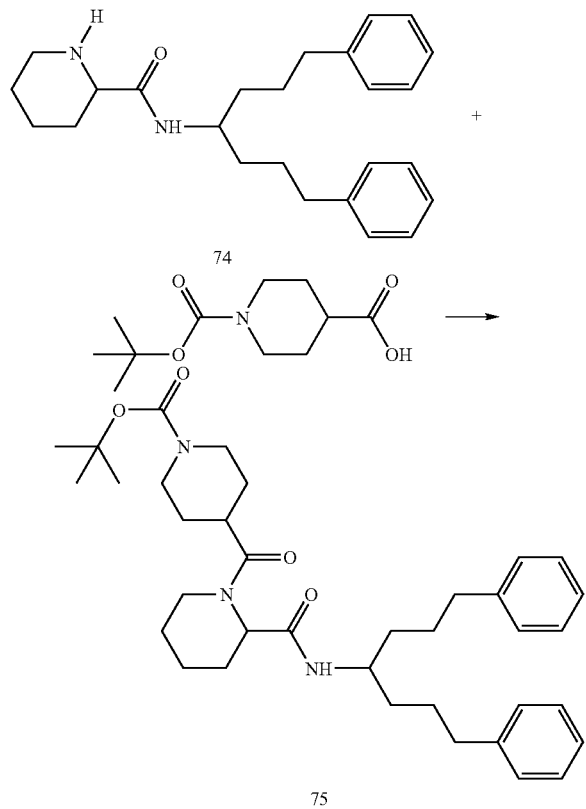

Piperidine-2-carboxylic acid [4-phenyl-1-(3-phenyl-propyl)-butyl]-amide (74) (1.00 g; 2.64 mmol) is dissolved in methylene chloride (25 mL) at ambient temperature. 1-tert-Butoxycarbonyl-piperidine-4-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 16 hours at room temperature, then concentrated under reduced pressure. The residue is purified via silica gel chromatography (30%→50% ethyl acetate in hexanes) affording the desired product (75) as a solid. ESMS: MH+ 590.6

Example 68

Preparation of 1-(piperidine-4-carbonyl)-piperidine-2-carboxylic acid [4-phenyl-1-(3-phenyl-propyl)-butyl]-amide (76)

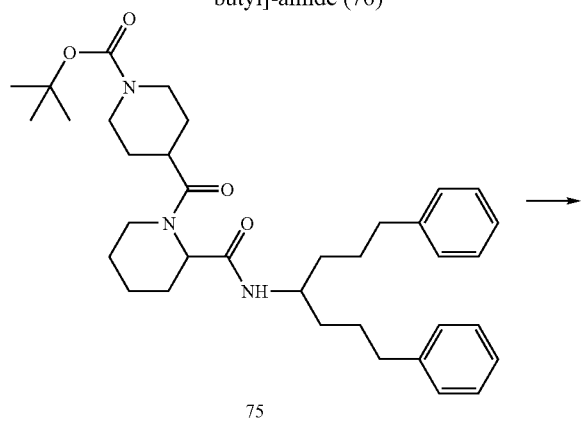

-continued

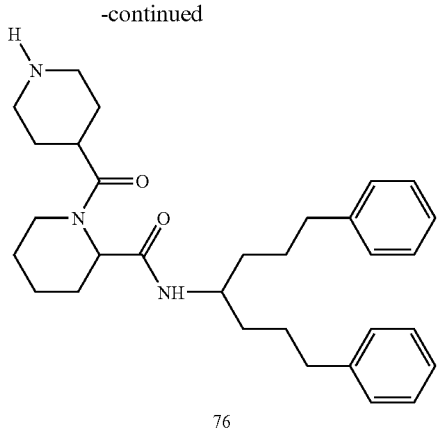

1-(1-tert-butoxycarbonylpiperidine-4-carbonyl)-piperidine-2-carboxylic acid [4-phenyl-1-(3-phenyl-propyl)-butyl]-amide (75) (1.41 g; 2.39 mmol) is dissolved in methylene chloride (30 mL) at ambient temperature. Trifluoroacetic acid (15 mL) is added in a slow stream, and the solution is stirred for 2.25 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO4, filtered, and concentrated in vacuo affording the desired product (1.02 g) as an oil. ESMS: MH+ 490.4

Example 69

Preparation of N-{1-[2-(R)-hydroxy-3-(quinolin-5-yloxy)-propyl]-piperidine-4 carbonyl}-piperidine-2-carboxylic acid [4-phenyl-1-(3-phenyl-propyl)-butyl]-amide (77)

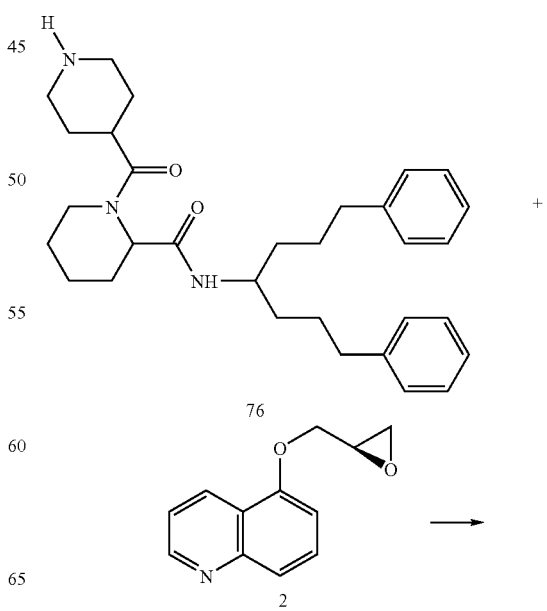

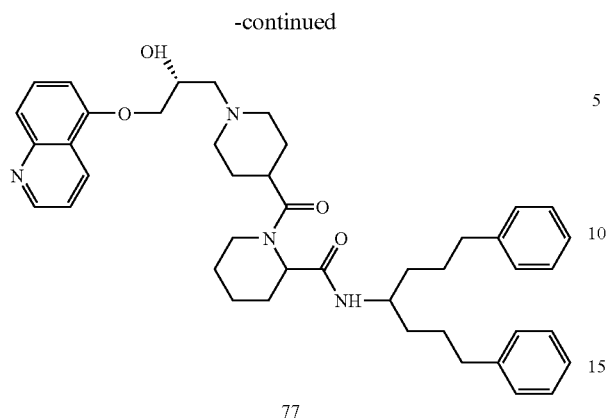

77

1-(Piperidine-4-carbonyl)-piperidine-2-carboxylic acid [4-phenyl-1-(3-phenyl-propyl)-butyl]-amide (76) (243.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 17 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (250 mg) as a white solid. ESMS: MH$^+$ 691.6

Example 70

Preparation of 1-(1-tert-butoxycarbonylpiperidine-3-carbonyl)-piperidine-3-carboxylic acid [4-phenyl-1-(3-phenyl-propyl)-butyl]-amide (78)

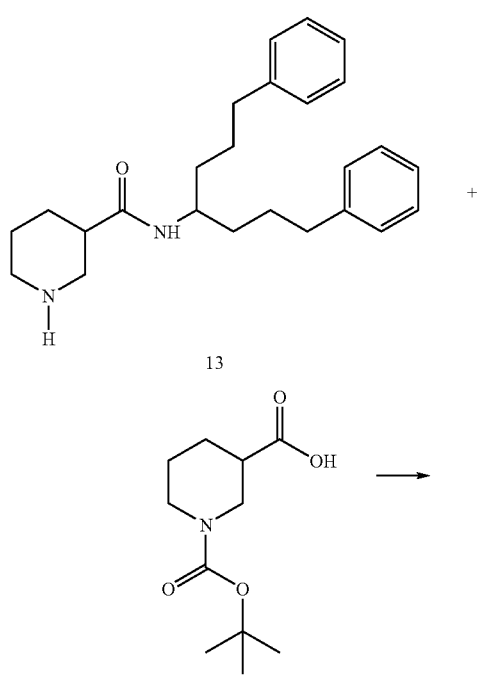

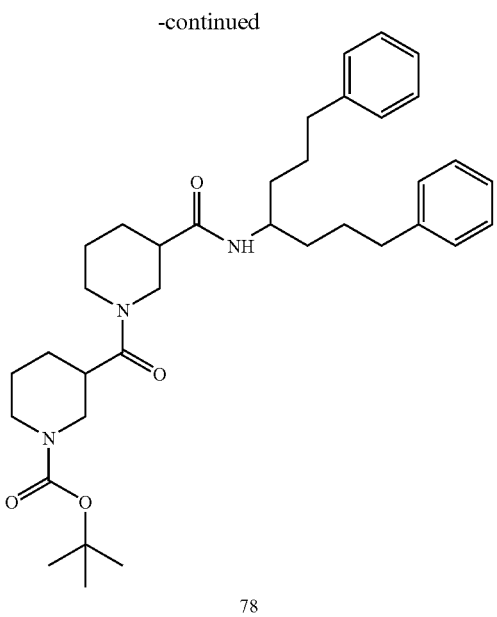

78

Piperidine-3-carboxylic acid [4-phenyl-1-(3-phenyl-propyl)-butyl]-amide (13) (1.00 g; 2.64 mmol) is dissolved in methylene chloride (25 mL) at ambient temperature. 1-tert-Butoxycarbonyl-piperidine-4-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 18 hr. at room temperature, then concentrated under reduced pressure. The residue is purified via silica gel chromatography (50%→70% ethyl acetate in hexanes) affording the desired product (78) as a solid. ESMS: MH$^+$ 590.6

Example 71

Preparation of 1-(piperidine-3-carbonyl)-piperidine-3-carboxylic acid [4-phenyl-1-(3-phenyl-propyl)-butyl]-amide (79)

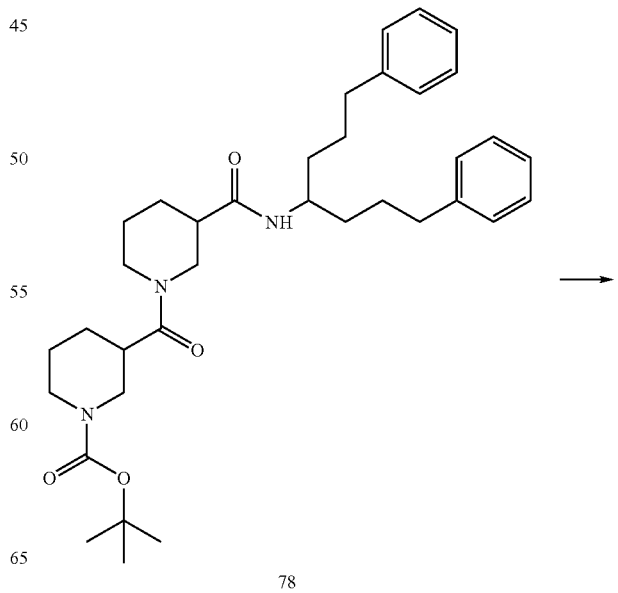

78

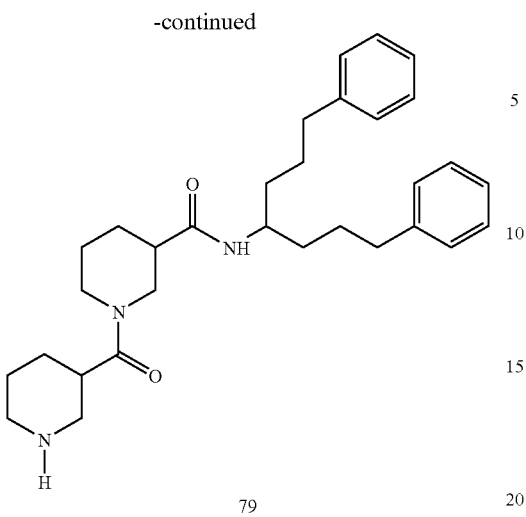

79

1-(1-tert-butoxycarbonylpiperidine-3-carbonyl)-piperidine-3-carboxylic acid [4-phenyl-1-(3-phenyl-propyl)-butyl]-amide (78) (1.41 g; 2.39 mmol) is dissolved in methylene chloride (40 mL) at ambient temperature. Trifluoroacetic acid (20 mL) is added in a slow stream, and the solution is stirred for 5 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO$_4$, filtered, and concentrated in vacuo affording the desired product (0.97 g) as a white solid.

Example 72

Preparation of N-{1-[2-(R)-hydroxy-3-(quinolin-5-yloxy)-propyl]-piperidine-3-carbonyl}-piperidine-3-carboxylic acid [4-phenyl-1-(3-phenyl-propyl)-butyl]-amide (80)

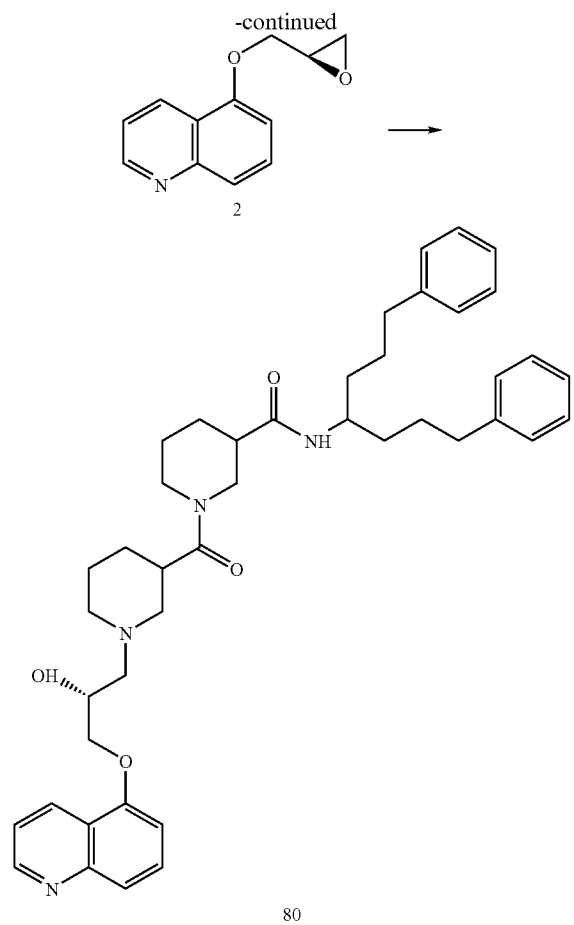

80

1-(Piperidine-3-carbonyl)-piperidine-3-carboxylic acid [4-phenyl-1-(3-phenyl-propyl)-butyl]-amide (79) (243.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 17 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (230 mg) as a white solid. ESMS: MH$^+$ 691.6

Example 73

Preparation of 1-(1-tert-butoxycarbonylpiperidine-3-carbonyl)-piperidine-2-carboxylic acid [4-phenyl-1-(3-phenyl-propyl)-butyl]-amide (81)

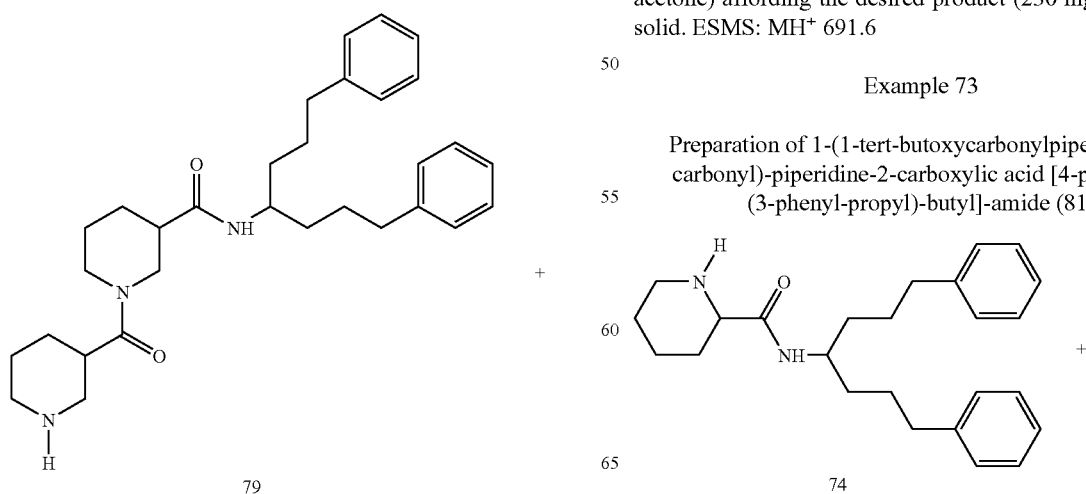

79                                74

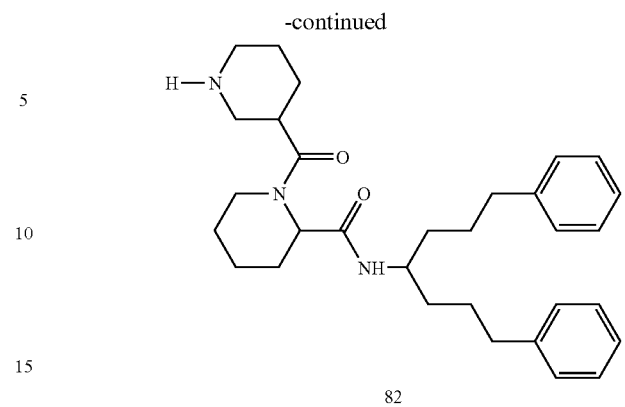

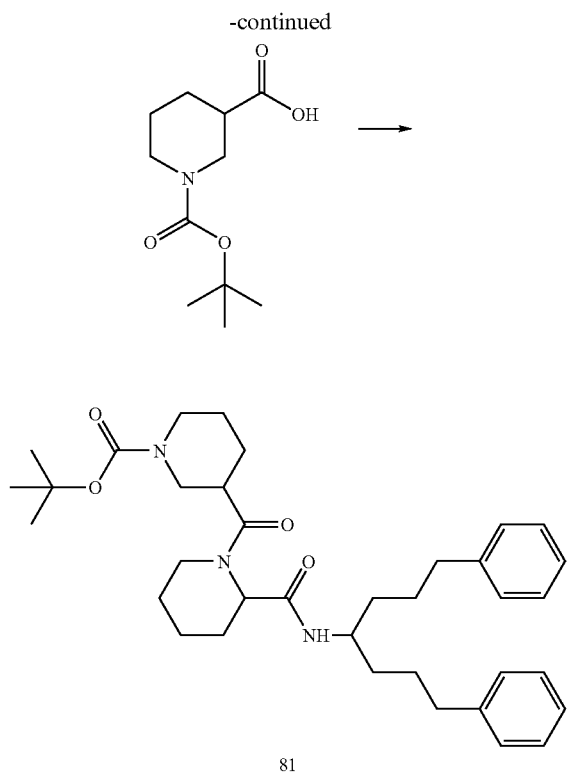

Piperidine-2-carboxylic acid [4-phenyl-1-(3-phenyl-propyl)-butyl]-amide (74) (1.00 g; 2.64 mmol) is dissolved in methylene chloride (25 mL) at ambient temperature. 1-tert-Butoxycarbonyl-piperidine-3-carboxylic acid (0.73 g; 3.17 mmol), N,N-diisopropylethylamine (0.75 g; 5.81 mmol) and PyBOP (1.65 g; 3.17 mmol) are added sequentially. The reaction is stirred for 19 hours at room temperature, then concentrated under reduced pressure. The residue is purified via silica gel chromatography (30%→50% ethyl acetate in hexanes) affording the desired product (81) as a solid. ESMS: MH+ 590.6

Example 74

Preparation of 1-(piperidine-3-carbonyl)-piperidine-2-carboxylic acid [4-phenyl-1-(3-phenyl-propyl)-butyl]-amide (82)

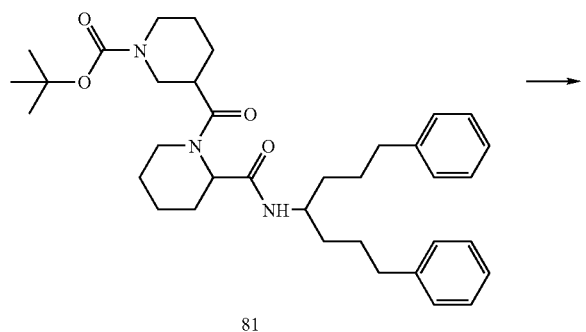

1-(1-tert-butoxycarbonylpiperidine-3-carbonyl)-piperidine-2-carboxylic acid [4-phenyl-1-(3-phenyl-propyl)-butyl]-amide (81) (1.35 g; 2.29 mmol) is dissolved in methylene chloride (40 mL) at ambient temperature. Trifluoroacetic acid (20 mL) is added in a slow stream, and the solution is stirred for 4 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO4, filtered, and concentrated in vacuo affording the desired product (1.09 g) as an oil.

Example 75

Preparation of N-{1-[2-(R)-hydroxy-3-(quinolin-5-yloxy)-propyl]-piperidine-2-carbonyl}-piperidine-3-carboxylic acid [4-phenyl-1-(3-phenyl-propyl)-butyl]-amide (83)

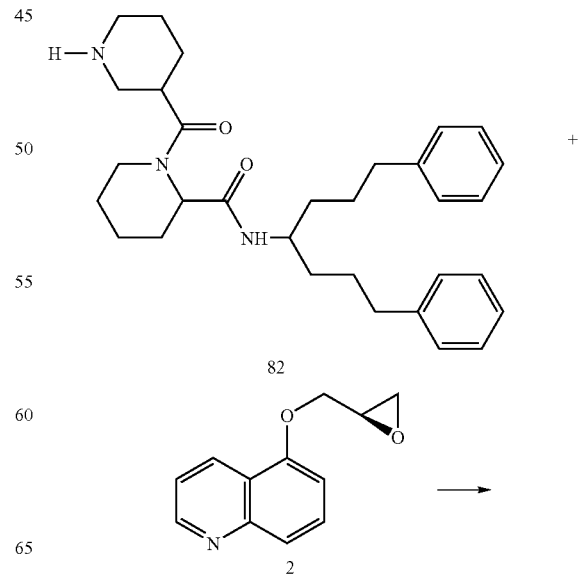

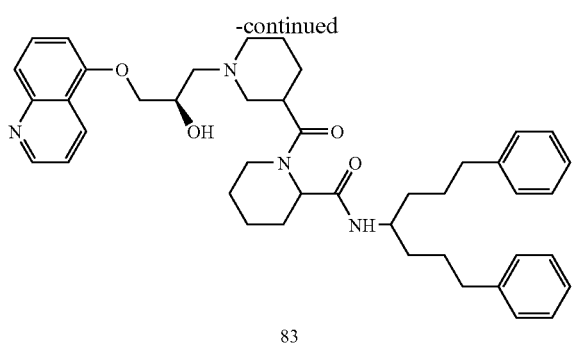

83

1-(Piperidine-3-carbonyl)-piperidine-2-carboxylic acid [4-phenyl-1-(3-phenyl-propyl)-butyl]-amide (82) (243.4 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 21 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (210 mg) as a white solid. ESMS: MH+ 691.2

Example 76

Preparation of N-tert-butoxycarbonyl-3-(3-pyridyl)-alanine [4-phenyl-1-(3-phenyl-propyl)-butyl]-amide (84)

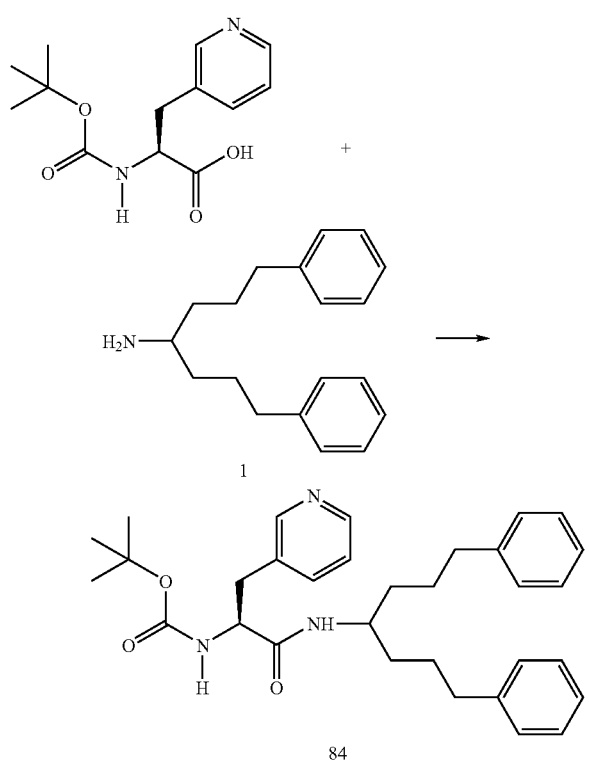

N-tert-Butoxycarbonyl-3-(3-pyridyl)-alanine (1.00 g; 3.76 mmol) is dissolved in methylene chloride (25 mL) at ambient temperature. 1,7-Diphenyl-4-aminoheptane hydrochloride (1) (1.37 g; 4.51 mmol), N,N-diisopropylethylamine (1.55 g; 12.0 mmol) and PyBOP (2.34 g; 4.51 mmol) are added sequentially. The reaction is stirred for 2.5 hours at room temperature, then concentrated under reduced pressure. The residue is purified via silica gel chromatography (60%→80% ethyl acetate in hexanes) affording the desired product (84) as a solid. ESMS: MH+ 516.2

Example 77

Preparation of 3-(3-pyridyl)-alanine [4-phenyl-1-(3-phenyl-propyl)-butyl]-amide (85)

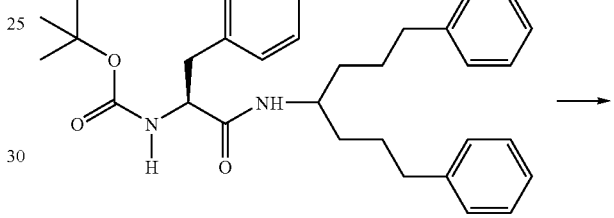

84

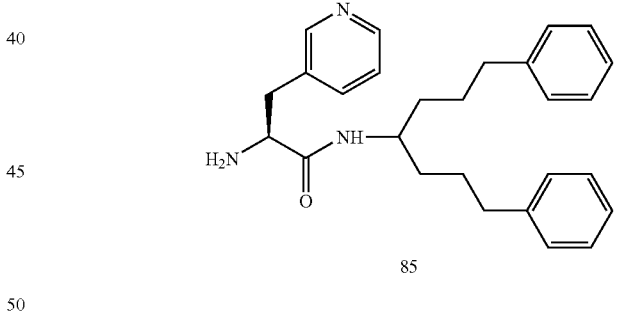

85

N-tert-Butoxycarbonyl-3-(3-pyridyl)-alanine [4-phenyl-1-(3-phenyl-propyl)-butyl]-amide (84) (2.08 g; 4.03 mmol) is dissolved in methylene chloride (40 mL) at ambient temperature. Trifluoroacetic acid (20 mL) is added in a slow stream, and the solution is stirred for 4 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO4, filtered, and concentrated in vacuo affording the desired product (1.59 g) as an oil. ESMS: MH+ 416.2

Example 78

Preparation of N-(N-tert-butoxycarbonyl-piperidine-4-carbonyl)-3-(3-pyridyl)-alanine [4-phenyl-1-(3-phenyl-propyl)-butyl]-amide (86)

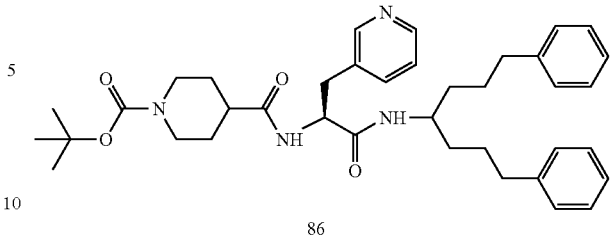

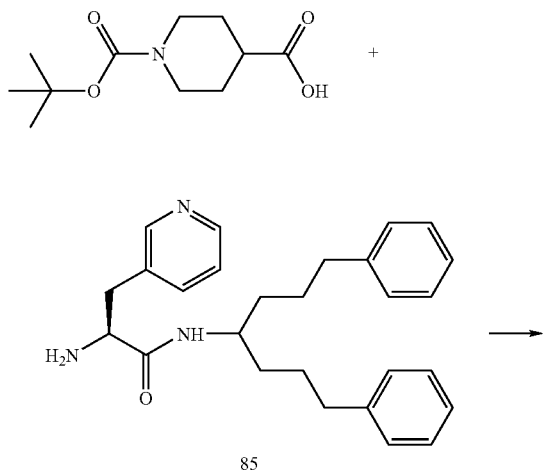

1-tert-Butoxycarbonyl-piperidine-4-carboxylic acid (0.66 g; 2.89 mmol) is dissolved in methylene chloride (25 mL) at ambient temperature. 3-(3-Pyridyl)-alanine [4-phenyl-1-(3-phenyl-propyl)-butyl]-amide (85) (1.00 g; 2.41 mmol), N,N-diisopropylethylamine (0.68 g; 5.29 mmol) and PyBOP (1.50 g; 2.89 mmol) are added sequentially. The reaction is stirred for 5 hours at room temperature, then concentrated under reduced pressure. The residue is purified via silica gel chromatography (80%→100% ethyl acetate in hexanes) affording the desired product (86) as a white solid. ESMS: MH$^+$ 627.6

Example 79

Preparation of N-(piperidine-4-carbonyl)-3-(3-pyridyl)-alanine [4-phenyl-1-(3-phenyl-propyl)-butyl]-amide (87)

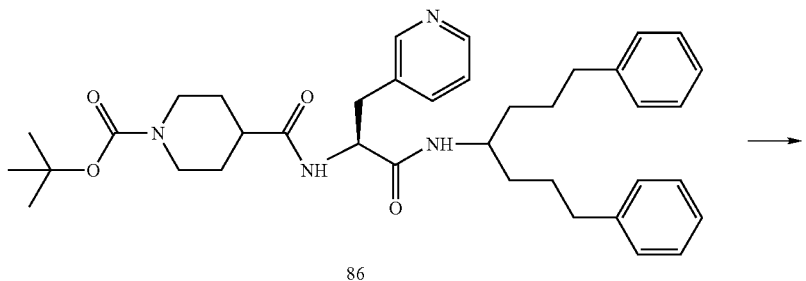

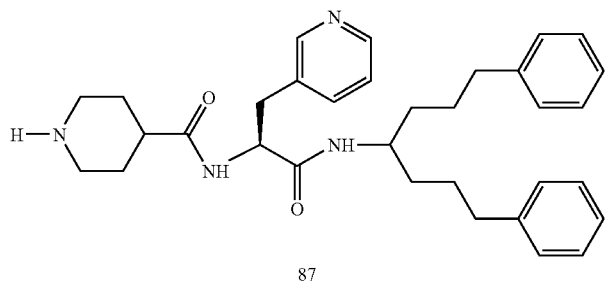

N-(N-tert-Butoxycarbonyl-piperidine-4-carbonyl)-3-(3-pyridyl)-alanine [4-phenyl-1-(3-phenyl-propyl)-butyl]-amide (86) (1.30 g; 2.07 mmol) is dissolved in methylene chloride (40 mL) at ambient temperature. Trifluoroacetic acid (20 mL) is added in a slow stream, and the solution is stirred for 2 hours at ambient temperature. The solution is concentrated in vacuo at 40° C. The residue is dissolved in methylene chloride (200 mL) and poured onto saturated sodium bicarbonate solution. The pH is adjusted to 9 with saturated potassium carbonate solution. The mixture is shaken the layers separated. The water layer is extracted with methylene chloride (3×50 mL). The combined organic extracts are washed with water, dried over MgSO$_4$, filtered, and concentrated in vacuo affording the desired product (0.98 g) as a white solid. ESMS: MH$^+$ 527.2

Example 80

Preparation of N-{1-[2-(R)-hydroxy-3-(quinolin-5-yloxy)-propyl]-piperidine-4-carbonyl}-3-(3-pyridyl)-alanine [4-phenyl-1-(3-phenyl-propyl)-butyl]-amide (88)

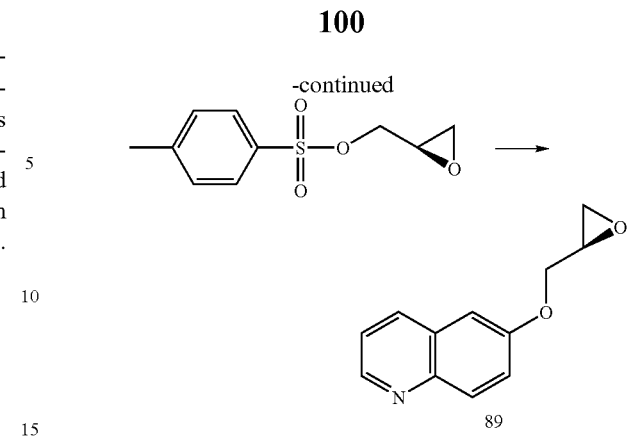

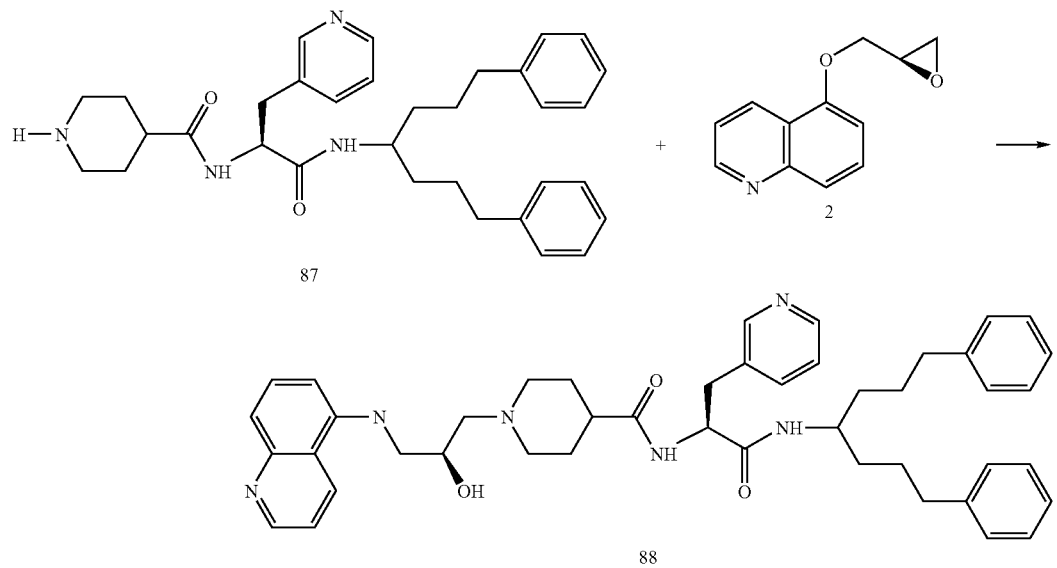

N-(Piperidine-4-carbonyl)-3-(3-pyridyl)-alanine [4-phenyl-1-(3-phenyl-propyl)-butyl]-amide (87) (261.8 mg; 0.497 mmol) is dissolved in ethanol (12 mL) at ambient temperature. (R)-5-Oxiranylmethoxy-quinoline (2) (100.0 mg; 0.497 mmol) is added, then the mixture is refluxed for 25 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (190 mg) as a white solid. ESMS: MH$^+$ 728.6

Example 81

Preparation of (R)-6-oxiranylmethoxy-guinoline (89)

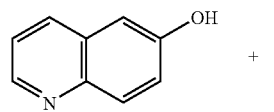

Sodium hydride (60 weight %; 0.36 g; 9.0 mmol) is washed with hexanes (3×5 mL) under an argon blanket. DMF (3 mL) is then added at ambient temperature and the stirred slurry is cooled to 5° C. A solution of 6-hydroxyquinoline (1.00 g; 6.9 mmol) in DMF (13 mL) is added dropwise over 10 minutes. The resulting mixture is allowed to warm to ambient temperature over 30 minutes affording a clear, reddish-brown solution. A solution of (R)-(–)-glycidyl tosylate (2.04 g; 9.0 mmol) in DMF (10 mL) is added dropwise over 10 minutes. The resulting mixture is stirred at ambient temperature for 13 hours, quenched by the addition of saturated aqueous ammonium chloride (5 mL), poured onto water (150 mL), and extracted with ether (3×75 mL). The combined ether layers are washed with saturated aqueous sodium bicarbonate (2×75 mL), then dried over MgSO$_4$, filtered, and concentrated in vacuo. The residue is purified via silica gel chromatography with gradient elution (40%→70% ethyl acetate in hexanes) affording the desired product (0.94 g) as an oil. CIMS: MH$^+$ 202.

Example 82

Preparation of (R)-1-[2-hydroxy-3-(quinolin-6-yloxy)-propyl]-piperidine-4-carboxylic acid [4-phenyl-1-(3-phenyl-propyl)-butyl]-amide (90)

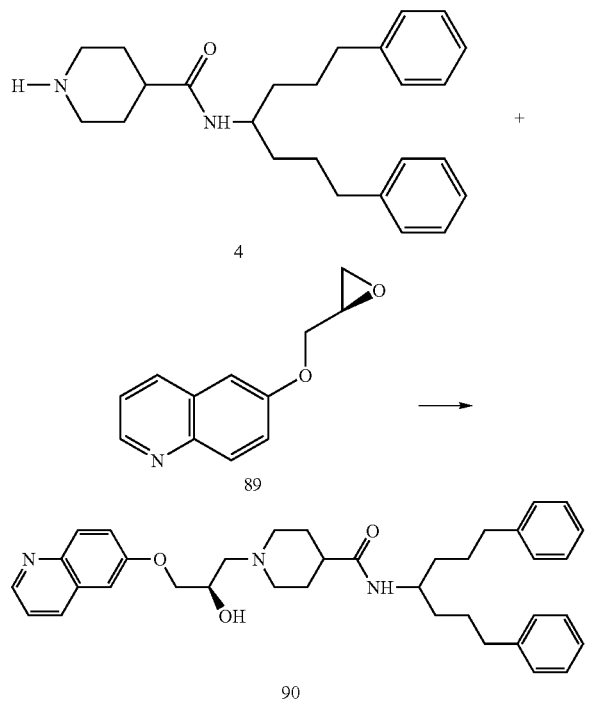

Piperidine-4-carboxylic acid [4-phenyl-1-(3-phenyl-propyl)-butyl]-amide (4) (100.0 mg; 0.264 mmol) is dissolved in ethanol (10 mL) at ambient temperature. (R)-6-Oxiranyl-methoxy-quinoline (89) (53.0 mg; 0.264 mmol) is added, then the mixture is refluxed for 17 hours. After cooling to ambient temperature, the solution is concentrated in vacuo at 40° C. The residue is purified via silica gel chromatography with gradient elution (70%→90% ethyl acetate in hexanes, then 50%→70% acetone in hexanes) affording the desired product (50 mg) as a white solid.

ESMS: MH+ 580.4.

Example 83

Preparation of (R)-4-oxiranylmethoxy-quinoline (91)

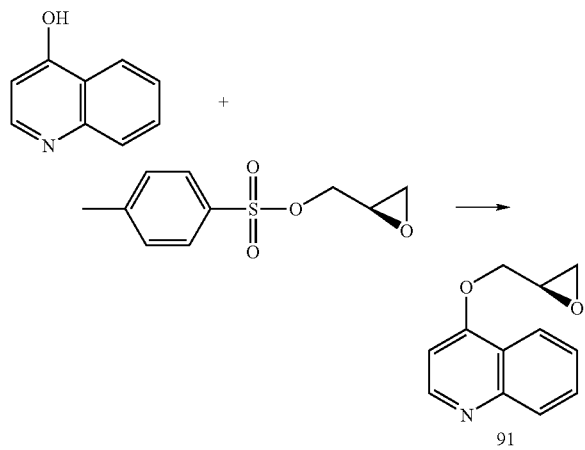

Sodium hydride (60 weight %; 1.79 g; 44.8 mmol) is washed with hexanes (3×10 mL) under an argon blanket. DMF (17 mL) is then added at ambient temperature and the stirred slurry is cooled to 5° C. A solution of 5-hydroxyquinoline (5.00 g; 34.4 mmol) in DMF (65 mL) is added dropwise over 10 minutes. The resulting mixture is allowed to warm to ambient temperature over 1 hour affording a clear, reddish-brown solution. A solution of (R)-(−)-glycidyl tosylate (10.22 g; 44.8 mmol) in DMF (50 mL) is added dropwise over 10 minutes. The resulting mixture is stirred at ambient temperature for 20.5 hours, quenched by the addition of saturated aqueous ammonium chloride (25 mL), poured onto water (750 mL), and extracted with ether (3×375 mL). The combined ether layers are washed with saturated aqueous sodium bicarbonate (2×375 mL), then dried over MgSO$_4$, filtered, and concentrated in vacuo. The residue is purified via silica gel chromatography with gradient elution (50%→60% acetone in hexanes) affording the desired product (1.11 g) as a tan solid. ESMS: MH 202.2.

Example 84

Preparation of (R)-1-[2-hydroxy-3-(quinolin-4-yloxy)-propyl]-piperidine-4-carboxylic acid [4-phenyl-1-(3-phenyl-propyl)-butyl]-amide (92)

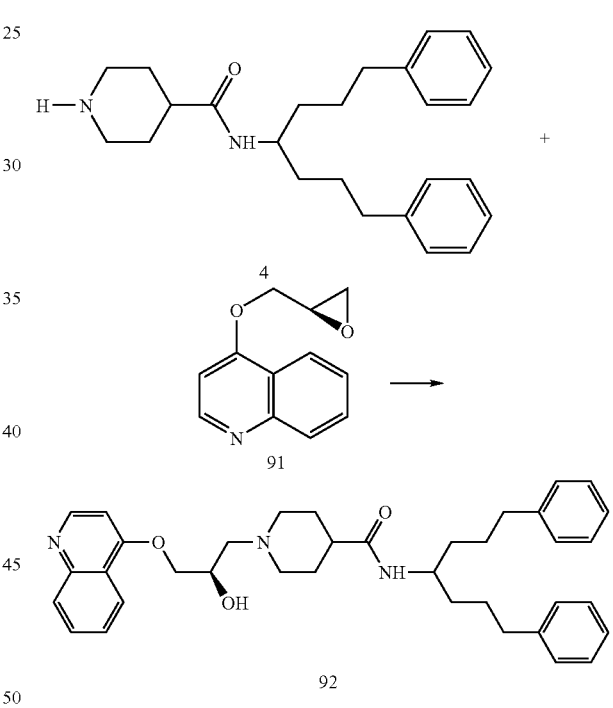

Piperidine-4-carboxylic acid [4-phenyl-1-(3-phenyl-propyl)-butyl]-amide (4) (70.3 mg; 0.186 mmol) is dissolved in ethanol (10 mL) at ambient temperature. (R)-4-Oxiranyl-methoxy-quinoline (91) (37.4 mg; 0.186 mmol) is added, then the mixture is refluxed for 22 hours. After cooling to ambient temperature, the solution is concentrated in vacuo at 40° C. The residue is purified via silica gel chromatography with gradient elution (50%→100% acetone in hexanes, then 5%→20% ethanol in acetone) affording the desired product (50 mg) as a yellow solid. ESMS: MH+ 580.4.

Example 85

Activity of the Compounds

Accumulation Index of various compounds prepared above was tested according to the method in Reference Example 3. The results are in Table 3. Substrate Potential of various compounds prepared above was tested according to the method in Reference Example 4. The results are in Table 3.

TABLE 3

Accumulation Index and Substrate Potential of the Active Compounds

| Compound | Accumulation Index | Substrate Potential $Ka_{(MDR1-ATPase)}$, $Ki_{(MDR1-ATPase+verapamil)}$ |
|---|---|---|
| Example 5 | 10 | no activation, 0.3 micromolar |
| Example 6 | 6 | |
| Example 10 | 11 | |
| Example 11 | 11 | no activation, 0.02 micromolar |
| Example 14 | 8 | no activation, 0.3 micromolar |
| Example 15 | 9 | weak activation, >50 micromolar |
| Example 16 | 8 | |
| Example 18 | 9 | |
| Example 19 | 5 | |
| Example 21 | 8 | |
| Example 25 | 12 | 0.005 micromolar, 0.01 micromolar |
| Example 26 | 5 | no activation, 0.5 micromolar |
| Example 29 | 6 | |
| Example 32 | 9 | 0.01 micromolar, 0.05 micromolar |
| Example 33 | 8 | |
| Example 34 | 6 | |
| Example 35 | 7 | |
| Example 36 | 9 | no activation, 1 micromolar |
| Example 39 | 13 | |
| Example 40 | 12 | |
| Example 41 | 10 | |
| Example 42 | 12 | |
| Example 46 | 8 | |
| Example 50 | 10 | |
| Example 53 | 8 | |
| Example 56 | 9 | |
| Example 61 | 7 | |
| Example 64 | 8 | |
| Example 69 | 9 | |
| Example 72 | 9 | |
| Example 75 | 10 | |
| Example 80 | 9 | |
| Example 82 | 7 | |
| Example 84 | 9 | |

Example 86

Oral Composition for the Active Compound of this Invention

A composition for oral administration is prepared by reducing an active compound according to this invention to a No. 60 powder. Starch and magnesium stearate are passed through a No. 60 bolting cloth onto the powder. The combined ingredients are mixed for 10 minutes and filled into a hard shell capsule of a suitable size at a fill weight of 100 mg per capsule. The capsule contains the following composition:

| Active Compound | 5 mg |
|---|---|
| Starch | 88 mg |
| Magnesium Stearate | 7 mg |

Example 87

Oral Composition for the Active Compound of this Invention with a Chemotherapeutic Agent A mixture of vinblastine and an active compound according to this invention is reduced to a No. 60 powder. Lactose and magnesium stearate are passed through a No. 60 bolting cloth onto the powder. The combined ingredients are mixed for 10 minutes, and then filled into a No. 1 dry gelatin capsule. Each capsule contains the following composition:

| Active Compound | 5 mg |
|---|---|
| Vinblastine | 5 mg |
| Lactose | 580 mg |
| Magnesium Stearate | 10 mg |

Example 88

Parenteral Composition for the Active Compound of this Invention

An active compound according to this invention (1 mg) is dissolved in 1 mL of a solution of 10% cremaphor, 10% ethanol, and 80% water. The solution is sterilized by filtration.

Example 89

Parenteral Composition for the Active Compound of this Invention

A sufficient amount of an active compound according to this invention and TAXOL® are dissolved in a 0.9% sodium chloride solution such that the resulting mixture contains 0.9 mg/mL of the active compound of this invention and 1.2 mg/mL TAXOL®.

A sufficient amount of the solution to deliver 135 mg/sq m TAXOL® is administered intravenously over 24 hours to a patient suffering from ovarian cancer.

What is claimed is:
1. A compound having the structure:

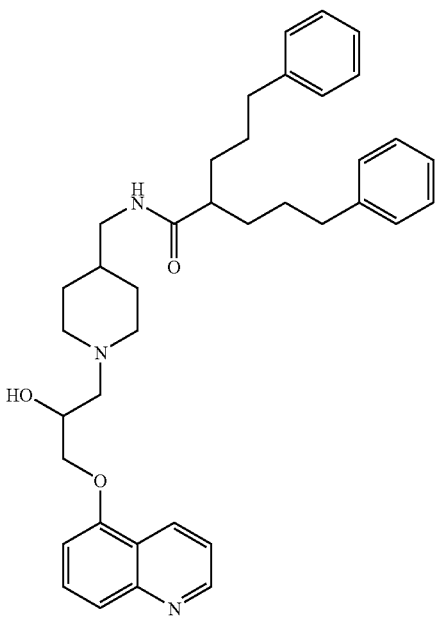

or an optical isomer, diastereomer, enantiomer or pharmaceutically acceptable salt thereof.

2. A composition comprising a compound according to claim 1 and a pharmaceutically acceptable carrier.

3. A pharmaceutical combination comprising a compound according to claim 1 and a therapeutic agent.

4. A method of inhibiting or relieving MRP1- or Pgp-mediated multidrug resistance comprising administering a compound according to claim 1 to a mammal in need of such treatment.

5. The method of claim 4, further comprising administering a therapeutic agent to the mammal before, during or after administering the compound.

6. The method of claim 5, wherein the therapeutic agent is selected from the group consisting of (i) cancer therapeutic agents, (ii) antibacterial agents, (iii) antiviral agents, (iv) antifungal agents, and (v) combinations thereof.

7. A method of inhibiting MRP1 or Pgp transport activity in a cell comprising contacting a cell with a compound according to claim 1.

8. The method of claim 7, further comprising contacting the cell with a therapeutic agent before, during or after contacting the cell with the compound.

9. The method of claim 8, wherein the therapeutic agent is selected from the group consisting of (i) cancer therapeutic agents, (ii) antibacterial agents, (iii) antiviral agents, (iv) antifungal agents, and (v) combinations thereof.

* * * * *